US012600955B1

(12) United States Patent　　(10) Patent No.:　US 12,600,955 B1
Choi et al.　　(45) Date of Patent:　Apr. 14, 2026

(54) REPLICATION-COMPETENT RECOMBINANT HERPES SIMPLEX VIRUS TYPE 1 (HSV-1) COMPRISING DELETIONS IN THE ICP6 AND IR REGIONS

(71) Applicant: SUNGKWANG MEDICAL FOUNDATION, Seoul (KR)

(72) Inventors: Kyung Ju Choi, Seongnam-si (KR); Joo Hang Kim, Seongnam-si (KR)

(73) Assignee: SUNGKWANG MEDICAL FOUNDATION, Seoul (KR)

( * ) Notice: Subject to any disclaimer, the term of this patent is extended or adjusted under 35 U.S.C. 154(b) by 1121 days.

(21) Appl. No.: 17/267,392

(22) PCT Filed: Aug. 9, 2019

(86) PCT No.: PCT/KR2019/010068
　§ 371 (c)(1),
　(2) Date: Feb. 9, 2021

(87) PCT Pub. No.: WO2020/032680
　PCT Pub. Date: Feb. 13, 2020

(30) Foreign Application Priority Data

Aug. 10, 2018　(KR) ........................ 10-2018-0094006

(51) Int. Cl.
　*A61K 35/763*　　(2015.01)
　*A61P 35/00*　　(2006.01)
　　(Continued)

(52) U.S. Cl.
　CPC .............. *C12N 7/00* (2013.01); *A61K 35/763* (2013.01); *A61P 35/00* (2018.01); *C12N 15/86* (2013.01);
　　(Continued)

(58) Field of Classification Search
　CPC ........ A61K 35/763; C12N 2710/16622; C12N 2710/16633; C12N 2710/16643; C12N 2710/16651
　See application file for complete search history.

(56) References Cited

U.S. PATENT DOCUMENTS 6,040,169　A　　3/2000　Brown et al.
8,318,691　B2　11/2012　Weichselbaum et al.
　　(Continued)

FOREIGN PATENT DOCUMENTS

CN　　101338302　A　　1/2009
CN　　104004786　A　　8/2014
　　(Continued)

OTHER PUBLICATIONS

Fukuhara, H., et al., Dec. 1, 2005, Triple Gene-Deleted Oncolytic Herpes Simplex Virus Vector Double-Armed with Interleukin 18 and Soluble B7-1 Constructed by Bacterial Artificial Chromosome-Mediated System, Cancer Res. 65(23):10663-10668.*
　　(Continued)

*Primary Examiner* — Jeffrey S Parkin

(74) *Attorney, Agent, or Firm* — Oblon, McClelland, Maier & Neustadt, L.L.P.

(57)　　　ABSTRACT

A recombinant herpes simplex virus type 1 (HSV-1), a recombinant HSV-1 vector, and a method of preparing the recombinant HSV-1, may enable easy genetic modification, as a relatively large foreign gene may be inserted or various foreign genes may be inserted simultaneously, as ICP6 and IR regions are simultaneously deleted. These may be used in cancer treatment as an oncolytic virus that is safe, while having an excellent effect in killing cancer cells.

15 Claims, 6 Drawing Sheets

Specification includes a Sequence Listing.

(51) Int. Cl.
   *C12N 7/00* (2006.01)
   *C12N 15/86* (2006.01)

(52) U.S. Cl.
   CPC .............. *C12N 2710/16622* (2013.01); *C12N 2710/16633* (2013.01); *C12N 2710/16643* (2013.01); *C12N 2710/16651* (2013.01)

(56) References Cited

U.S. PATENT DOCUMENTS

| | | |
|---|---|---|
| 8,772,261 B2 | 7/2014 | Weichselbaum et al. |
| 10,806,761 B2 | 10/2020 | Nakashima et al. |
| 2002/0019362 A1 | 2/2002 | Weichselbaum et al. |
| 2003/0207829 A9 | 11/2003 | Weichselbaum et al. |
| 2004/0228876 A1 | 11/2004 | Nishiyama |
| 2011/0002890 A1 | 1/2011 | Weichselbaum et al. |
| 2013/0039890 A1 | 2/2013 | Weichselbaum et al. |

FOREIGN PATENT DOCUMENTS

| | | |
|---|---|---|
| EP | 1 150 696 B1 | 5/2006 |
| KR | 10-0237144 B1 | 3/2000 |
| KR | 10-2016-0048759 A | 5/2016 |
| KR | 10-2018-0037140 A | 4/2018 |
| KR | 10-1974169 B1 | 4/2019 |
| WO | WO 2011/101912 A1 | 8/2011 |
| WO | WO 2020/032680 A1 | 2/2020 |

OTHER PUBLICATIONS

GenBank JQ673480, May 10, 2012, Human herpesvirus 1 strain KOS, complete genome.*

Miyagawa, Y., et al., Mar. 16, 2015, Herpes simplex viral-vector designs for efficient transduction of nonneuronal cells without cytotoxicity, PNAS E1631-E1641.*

Kehm, R., et al., Restitution of the UL56 gene expression of HSV-1 HFEM led to restoration of virulent phenotype; deletion of the amino acids 217 to 234 of the UL56 protein abrogates the virulent phenotype, Vir. Res. 40:17-31.*

Enow, J. A., et al., 2023, Tumor Tropism of DNA Viruses for Oncolytic Virotherapy, Viruses 15:2262, pp. 1-17.*

Shen, Y., et al., Apr. 2025, HSV-1 as a gene delivery platform for cancer gene therapy, Trends Pharmacol. Sci. 46(4):324-336.*

Aldrak, N., et al., 2021, Oncolytic Herpes Simplex Virus-Based Therapies for Cancer, Cells 10, 1541, pp. 1-17.*

International Search Report issued Nov. 21, 2019 in PCT/KR2019/010068 filed Aug. 9, 2019, citing documents, AA-AG, AI-AK, AT-AU and AW therein, 4 pages.

Korean Office Action issued Nov. 8, 2018 in Korean Application No. 10-2018-0094006 filed Aug. 10, 2018, citing documents AT-AV therein, 7 pages.

Korean Notice of Allowance issued Apr. 7, 2019 in Korean Application No. 10-2018-0094006 filed Aug. 10, 2018, citing documents AM and AT-AV therein, 2 pages.

Wakimoto, H., et al., "Human Glioblastoma-Derived Cancer Stem Cells: Establishment of Invasive Glioma Models and Treatment with Oncolytic Herpes Simplex Virus Vectors", Cancer Research, vol. 69, No. 8, 2009, pp. 3472-3481, 12 total pages.

Maclean, A., et al., "Deletion and Duplication Variants around the Long Repeats of Herpes Simplex Virus Type 1 Strain 17", Journal of general virology, vol. 68, 1987, pp. 3019-3031, 14 total pages.

Kehm, R., et al., "Restitution of the UL56 gene expression of HSV-1 Hfem led to restoration of virulent phenotype: deletion of the amino acids 217 to 234 of the UL56 protein abrogates the virulent phenotype", Virus Research, vol. 40, 1996, pp. 17-31.

Kehm, R., et al., "Identification of the UL56 Protein of Herpes Simplex Virus Type 1 within the Virion by Immuno Electron Microscopy", Virus Genes, vol. 17. No. 1, 1998, pp. 49-53, 6 total pages.

GenBank: JQ673480.1, "Human herpesvirus 1 strain KOS, complete genome", Nucleotide—NCBI, 2012, 53 total pages.

GenBank: AFE62867.1, "ribonucleotide reductase subunit 1 [Human alphaherpesvirus 1]", Protein—NCBI, 2012, 2 total pages.

Capecchi, M., et al., "High efficiency transformation by direct microinjection of DNA into cultured mammalian cells", PlumX Metrics, vol. 22, No. 2, 1980, 13 total pages.

Harland, R., et al., "Translation of mRNA Injected into Xenopus Oocytes Is Specifically Inhibited by Antisense RNA", the Journal of Cell Biology, vol. 101, 1985, pp. 1094-1099.

Graham, F., et al., "A New Technique for the Assay of Infectivity of Human Adenovirus 5 Dna", Virology, vol. 52, 1973, pp. 456-467, 13 total pages.

Chen, C., et al., "High-Efficiency Transformation of Mammalian Cells by Plasmid DNA", Molecular and Cellular Biology, vol. 7, No. 8, 1987, pp. 2745-2752.

Neumann, E., et al., "Gene transfer into mouse lyoma cells by electroporation in high electric fields", The EMBO Journal, vol. 1, No. 7, 1982, pp. 841-845.

Tur-Kaspa, R., et al., "Use of Electroporation to Introduce Biologically Active Foreign Genes into Primary Rat Hepatocyptes", Molecular and Cellular Biology, vol. 6, No. 2, 1986, pp. 716-718.

Wong, T., et al., "Appearance of β-lactamase activity in animal cells upon liposome-mediated gene transfer", Gene, vol. 10, No. 2, 1980, 2 total pages.

Nicolau, C., et al., "Liposome-mediated DNA transfer in eukaryotic cells: Dependence of the transfer efficiency upon the type of liposomes used and the host cell cycle stage", Biochimica et Biplhysica Acta (BBA)—Molecular Cell Research, vol. 721, No. 2, 1982, 2 total pages.

Nicolau, C., et al., "Liposomes as carriers for in vivo gene transfer and expression", Methods in Enzymology, vol. 149, 1987, 2 total pages.

Gopal, T., "Gene Transfer Method for Transient Gene Expression, Stable Transformation, and Cotransformation of Suspension Cell Cultures", Molecular and Cellular Biology, vol. 5, No. 5, 1985, pp. 1188-1190.

Yang, N-S., et al., "In vivo and in vitro gene transfer to mammalian somatic cells by particle bombardment", Proc. Natl. Acad. Sci, USA, bol, 87, 1990, pp. 9568-9572.

NCBI Blast:seq.No. 1, "Sequences producing significant alignments", 2018, 38 total pages.

Japanese Office Action issued Mar. 15, 2022. in Japanese Patent Application No. 2021-506935 (with English translation), citing documents AX therein, 6 pages.

Frank J. Jenkins, et al., "Role of the Herpes Simplex Virus 1 Internal Repeat Sequences in Pathogenicity", Intervirology vol. 31, (1990), 12 pages.

Combined Chinese Office Action and Search Report issued Aug. 31, 2023 in Chinese Application 201980051993.6, citing documents 1 and 15 therein, 10 pages.

\* cited by examiner

UL56-rpsL-neo

| promoter | rpsL-neo | NeoR/KanR |
|----------|----------|-----------|

UsIR-rpsL-neo

ΔICP6ΔIR-rpsL-neo

1: HSV-1 wt
2: ΔICP6-rpsL-neo
3-4: ΔICP6-ΔIR-rpsL-neo

1: HSV-1 wt
2: ΔICP6-rpsL-neo
3-4: ΔICP6-ΔIR-rpsL-neo

1: HSV-1 wt
2: ΔICP6-rpsL-neo
3-4: ΔICP6-ΔIR-rpsL-neo

1: ΔIR
2-3: ΔICP6-ΔIR

1: ΔICP6-ΔIR-rpsL-neo
2-3: ΔICP6-ΔIR

1: ΔICP6-ΔIR-rpsL-neo
2-3: ΔICP6-ΔIR

REPLICATION-COMPETENT RECOMBINANT HERPES SIMPLEX VIRUS TYPE 1 (HSV-1) COMPRISING DELETIONS IN THE ICP6 AND IR REGIONS

SEQUENCE LISTING

The instant application contains a Sequence Listing which has been submitted electronically in ASCII format and is hereby incorporated by reference in its entirety. Said ASCII copy, created on Sep. 8, 2021, is named 535141USSL.txt and is 201,054 bytes in size.

TECHNICAL FIELD

The present disclosure relates to a recombinant herpes simplex virus type 1 (HSV-1), a recombinant HSV-1 vector, and a method of preparing the same.

BACKGROUND ART

Herpes simplex virus (Herpes Simplex Virus: HSV) is one type of virus that belongs to the herpes virus family and is categorized into HSV-type 1 and HSV-type 2, which are also known as human herpes virus type 1 and type 2, respectively. Nucleic acids are double stranded, linear DNA having a molecular weight of $96\times10^6$ Daltons.

As talimogene laherparepvec (T-VEC) was approved by the U.S. Food and Drug Administration (FDA) in 2015 and has been clinically used for the treatment of malignant melanoma, development of an oncolytic/anticancer virus based on the herpes virus is in progress. However, the use of most of the currently developed anticancer HSV-1 is limited by its low therapeutic efficacy because viral replication is limited due to the absence of genes required for viral replication. Also, HSV-1 is a DNA virus having a large genome size of 152 kb, which makes genetic modification of HSV-1 not easy.

Thus, a recombinant HSV-1 vector capable of facilitating genetic modification and having excellent cancer treatment effects needs to be developed.

DESCRIPTION OF EMBODIMENTS

Technical Problem

Provided is a recombinant herpes simplex virus type 1 (HSV-1) having an HSV-1 genome, in which an infected-cell protein 6 (ICP6) region and an internal repeat (IR) region are deleted among HSV-1 genomic regions.

Provided is a recombinant HSV-1 vector including a genomic nucleotide sequence of the recombinant HSV-1.

Provided is a method of preparing the recombinant HSV-1.

Provided is a pharmaceutical composition for preventing or treating cancer, the composition including the recombinant HSV-1 or recombinant HSV-1 vector.

Provided is a method of preventing or treating cancer, the method including administering an effective amount of the recombinant HSV-1 or recombinant HSV-1 vector to a subject in need thereof.

Provided is a use of the recombinant HSV-1 or recombinant HSV-1 vector in preparing an agent for preventing or treating cancer.

Solution to Problem

According to an aspect of the present disclosure, provided is a recombinant herpes simplex virus type 1 (HSV-1).

The recombinant HSV-1 according to an aspect of the present disclosure has an HSV-1 genome, in which an infected-cell protein 6 (ICP6) region and an internal repeat (IR) region between a unique long (UL) region and a unique short (US) region are deleted among HSV-1 genomic regions. A vector structure in which both the ICP6 and IR regions are simultaneously deleted among HSV genomic regions has not been reported yet, and thus the recombinant HSV-1 according to an embodiment of the present disclosure is a recombinant virus having a novel structure. Since about 20 kb of genes are missing due to the deletion of the ICP6 and IR regions, a relatively large foreign gene may be inserted or more than one various foreign genes may be simultaneously inserted to the recombinant HSV-1. ICP6, a ribonucleotide reductase, is an enzyme that is involved in the DNA biosynthesis of HSV-1 and is necessary for DNA replication of the virus when normal cells are infected with the virus. In recent years, a ribonucleotide reductase is known to be overexpressed in various cancer cells. Thus, when the ICP6 gene is removed, replication of a virus in normal cells is restricted, whereas a virus actively replicated in cancer cells may be prepared. Also, two copies of ICPO, ICP34.5, and ICP4 exist in HSV-1, and a virus may be replicated only with one copy thereof. Therefore, removing one copy of ICPO, ICP34.5, and ICP4 in the IR region allows insertion of therapeutic genes of various sizes and types without any influence on the viral replication. In addition, HSV-1 has an IR region, which makes a total of four isotype viruses, but when the IR region is removed, a relatively more stable virus, which is only one HSV-1 isotype, may be prepared. That is, cancer cell selectivity may be imparted by removing the ICP6 gene in the HSV-1 genomic region, and a space to insert the therapeutic gene as well as the structural stability of the HSV-1 oncolytic/anticancer virus may be secured by removing the IR region in the HSV-1 genomic region.

As used herein, the term "deletion" refers to removing of genes on the viral genome. For example, genes may be removed using a restriction enzyme. The entire gene or a part of the gene nucleotide sequence may be removed using a gene cloning method using a restriction enzyme Expression of the functional protein of the gene may not occur or may be inhibited by the gene deletion. Deletion of the ICP6 and IR regions corresponding to a size of about 20 kb may allow insertion of a foreign gene having a long nucleotide sequence.

The term "herpes simplex virus (HSV)" used herein refers to a virus that belongs to a herpesviridae family and is categorized into herpes simplex virus type 1 (HSV-1) and herpes simplex virus type 2 (HSV-2). HSV-1 is also referred to as a human herpes virus type 1 (HHV-1). A nucleic acid of HSV-1 is a double-stranded, linear DNA. Thus, the genome of HSV-1 may be composed of double-stranded, linear DNAs. The genome sequences of HSV-1 may include any genome sequence of an HSV-1 strain available in the art. Examples of the sequences of an HSV-1 genome are disclosed in NCBI GenBank Accession No. JQ673480.1. Unless otherwise indicated herein, "HSV-1" is used interchangeably with "wild-type HSV-1" and is distinguished from "recombinant HSV-1" according to the above aspect. An HSV-1 genomic region may include a terminal repeat of long (TRL) region, a unique long (UL) region, an internal repeat of long (IRL) region, an internal repeat of short (IRS) region, a unique short (US) region, and a terminal repeat of short (TRS) region. The UL region may include nucleotide sequences of UL1 to UL56 genes. The US region may include nucleotide sequences of US1 to US12 genes. Also, the HSV-1 genomic region may not include a TRL region and a TRS region. For example, the HSV-1 genomic region may include a UL region, an IRL region, an IRS region, and a US region.

In one embodiment, a recombinant HSV-1 may include at least one HSV-1 genomic region selected from the group consisting of a TRL region; a UL region including nucleotide sequences of at least one gene selected from UL1 to UL38 and UL40 to UL56; a US region including nucleotide sequences of at least one gene selected from US1 to US12; and a TRS region. In some embodiments, the recombinant HSV-1 may include a combination of HSV-1 genomic regions selected from the group consisting of a TRL region; a UL region including nucleotide sequences of at least one gene selected from UL1 to UL38 and UL40 to UL56; a US region including nucleotide sequences of at least one gene selected from US1 to US12; and a TRS region. In some embodiments, the recombinant HSV-1 may include a TRL region; a UL region including nucleotide sequences of at least one gene selected from UL1 to UL38 and UL40 to UL56; a US region including nucleotide sequences of at least one gene selected from US1 to US12; and a TRS region.

The "terminal repeat of long (TRL) region" may have a size of about 9.2 kb.

The "unique long (UL) region" may have a size of about 108 kb. The UL region of HSV-1 may include nucleotide sequences of UL1 to UL56 genes. The recombinant HSV-1 according to an embodiment of the present disclosure may include a UL region, and the UL region may include nucleotide sequences of at least one gene selected from UL1 to UL38 and UL40 to UL56.

The "infected-cell protein 6 (ICP6)" may be UL39 gene. A nucleotide sequence of the ICP6 may have a size of about 4.8 kb. Examples of the nucleotide sequences of the ICP6 gene may be nucleotide sequences 86,364 to 89,777 among the HSV-1 genomic sequences disclosed in NCBI GenBank Accession No. JQ673480.1. In one embodiment, a genome of the recombinant HSV-1 may be obtained by deleting the whole or a part of the ICP6 gene. In some embodiments, a genome of the recombinant HSV-1 may be obtained by deleting nucleotides 86,901 to 89,578 from the wild-type HSV-1 genomic sequence. For example, the genome of the recombinant HSV-1 may be obtained by deleting a nucleotide sequence of SEQ ID NO: 1 among nucleotide sequences of the ICP6 gene. Examples of amino acid sequences of the ICP6 protein are disclosed in NCBI GenBank Accession No. AFE62867.1.

In one embodiment, the deleted IR region may include at least one region selected from an internal repeat of long (IRL) region and an internal repeat of short (IRS) region. In some embodiments, the deleted IR region may include both an IRL region and an IRS region. The "IRL region" may have a size of about 9.2 kb. The "IRS region" may have a size of about 6.6 kb. Examples of nucleotide sequences of the IRL region may be nucleotide sequences 117,080 to 125,845 among the HSV-1 genomic sequences disclosed in NCBI GenBank Accession No. JQ673480.1. Examples of nucleotide sequences of the IRS region may be nucleotide sequences 126,241 to 132,463 among the HSV-1 genomic sequences disclosed in NCBI GenBank Accession No. JQ673480.1. In one embodiment, the genome of the recombinant HSV-1 may be obtained by deleting the whole or a part of the IR region. In some embodiments, the genome of the recombinant HSV-1 may be obtained by deleting nucleotides 117,080 to 131,261 from the wild-type HSV-1 genomic sequence. For example, the genome of the recombinant HSV-1 may be obtained by deleting a nucleotide sequence of SEQ ID NO: 2 nucleotide sequences of the IR region of HSV-1.

In one embodiment, the recombinant HSV-1 may be obtained by additionally deleting a part of the nucleotide sequence of the UL56 gene together with the deletion of the whole or a part of the IR region. Examples of nucleotide sequences of the UL56 gene may be nucleotide sequences 116,142 to 116,846 among the HSV-1 genomic sequences disclosed in NCBI GenBank Accession No. JQ673480.1. In some embodiments, the genome of the recombinant HSV-1 may be obtained by deleting nucleotides 116,200 to 116,846 from the wild-type HSV-1 genomic sequence. For example, the deleted part of nucleotide sequence of the UL56 gene may be a nucleotide sequence of SEQ ID NO: 3. In some embodiments, the genome of the recombinant HSV-1 may be obtained by deleting nucleotides 116,200 to 131,261 from the wild-type HSV-1 genomic sequence.

The "US region" may have a size of about 13 kb. The US region of HSV-1 may include nucleotide sequences of US1 to US12 genes. According to an aspect of an embodiment, the recombinant HSV-1 may include a US region, and the US region may include nucleotide sequences of at least one gene selected from US1 to US12.

The "TRS region" may have a size of about 4 kb.

A genome of the recombinant HSV-1 may include a nucleotide sequence of SEQ ID NO: 4.

The recombinant HSV-1 may be an oncolytic virus. As used herein, the term "oncolytic virus" is interchangeably used with "oncolytic/anticancer virus". An oncolytic virus may activate immune cells by exposing antigens of cancer cells by specifically killing cancer cells or tumor cells. In this regard, an oncolytic virus may be used by itself for anticancer purpose and may be used in combination with other anticancer agents to enhance the anticancer effects. Also, various therapeutic genes may be inserted into the oncolytic virus to enhance the anticancer effects.

The gene sequences are construed to include gene sequences that exhibit substantial identity or substantial similarity. The substantial identity refers to at least 80% homology, more preferably 90% homology, and most preferably 95% homology, when the sequence of the present invention is aligned with a sequence that is different from the sequence of the present invention to correspond each other as much as possible, and the aligned sequences are analyzed by algorithms commonly used in the art. The substantial similarity refers to all changes including a change in gene sequences such as deletion or insertion of one or more bases that do not affect the purpose of the present invention to minimize homologous recombination with recombinant viral vectors.

According to another aspect of an embodiment, provided is a recombinant HSV-1 vector including a genome nucleotide sequence of the recombinant HSV-1 according to an embodiment.

In particular, regarding a recombinant HSV-1 vector including a genome nucleotide sequence of HSV-1, the genome nucleotide sequence of HSV-1 provides a recombinant HSV-1 vector, in which ICP6 is deleted, and nucleotide sequences between a UL region and a US region are deleted.

The term "virus vector" refers to a virus-derived vector capable of delivering foreign or heterologous genetic information to a host.

The HSV-1, recombinant HSV-1, ICP6, IR region, and deletion may be defined the same as described above.

In one embodiment, the vector may include nucleotide sequences of at least one genome region of HSV-1 selected from the group consisting of a TRL region; a UL region including nucleotide sequences of at least one gene selected from UL1 to UL38 and UL40 to UL56; a US region including nucleotide sequences of at least one gene selected from US1 to US12; and a TRS region. In some embodiments, the vector may include a TRL region; a UL region including nucleotide sequences of at least one gene selected from UL1 to UL38 and UL40 to UL56; a US region including nucleotide sequences of at least one gene selected from US1 to US12; and a TRS region.

The recombinant HSV-1 vector may further include nucleotide sequences of a foreign gene. In one embodiment, a nucleotide sequence of the foreign gene may be inserted into the deleted ICP6 or IR regions. In some embodiments, when there are more than one foreign gene to be inserted, the nucleotide sequence of each foreign gene may be inserted into the ICP6 and IR regions, but embodiments are not limited thereto. The nucleotide sequence may be any nucleotide sequence of a foreign gene that may be carried by the vector. For example, the foreign gene that may be carried by the vector may be a gene having anticancer effects, but embodiments are not limited thereto.

The recombinant HSV-1 vector may sequentially include nucleotide sequences of a TRL region, a UL region, a US region, and a TRS region and may be characterized by deleted ICP6 and IR regions. In one embodiment, the recombinant HSV-1 vector may have a genetic map shown in FIG. 1C. The recombinant HSV-1 vector according to an embodiment including the genomic nucleotide sequence of HSV-1, in which the nucleotide sequences of the ICP6 and IR regions are deleted, is named "ΔICP6ΔIR HSV-1 vector".

The recombinant HSV-1 vector may further include components that are generally included in a viral vector. For example, the recombinant HSV-1 vector may include a promoter that is operably linked to a foreign gene. The promoter may be of any type available in the art, and the type is not limited.

According to another aspect of an embodiment, provided is a method of preparing the recombinant HSV-1 according to the aspect above.

In particular, the method may include preparing a recombinant HSV-1 vector including genomic nucleotide sequences of HSV-1 having deleted ICP6 and IR regions; and transfecting cells with the vector to obtain a recombinant HSV-1.

The recombinant HSV-1 vector is defined the same as described above.

A method of transfecting cells with the vector may be performed using various methods available in the art. For example, cells may be transfected with the vector using methods such as microinjection (Capecchi, M. R., Cell, 22: 479 (1980); and Harland and Weintraub, J. Cell Biol. 101: 1094-1099 (1985)), calcium phosphate precipitation (Graham, F. L. et al., Virology, 52: 456 (1973); and Chen and Okayama, Mol. Cell. Biol. 7:2745-2752 (1987)), electroporation (Neumann, E. et al., EMBO J., 1: 841 (1982); and Tur-Kaspa et al., Mol. Cell Biol., 6:716-718 (1986)), liposome-mediated transfection (Wong, T. K. et al., Gene, 10: 87 (1980); Nicolau and Sene, Biochim. Biophys. Acta, 721: 185-190 (1982); and Nicolau et al., Methods Enzymol., 149:157-176 (1987)), DEAE-dextran treatment (Gopal, Mol. Cell Biol., 5:1188-1190 (1985)), and gene bombardment (Yang et al., Proc. Natl. Acad. Sci., 87:9568-9572 (1990)).

According to another aspect of an embodiment, provided is a pharmaceutical composition including the recombinant HSV-1 or recombinant HSV-1 vector.

According to another aspect of an embodiment, provided is a method of preventing or treating cancer, the method including administering an effective amount of the recombinant HSV-1 or recombinant HSV-1 vector to a subject in need thereof.

According to another aspect of an embodiment, provided is a use of the recombinant HSV-1 or recombinant HSV-1 vector in preparing an agent for preventing or treating cancer.

The recombinant HSV-1 and recombinant HSV-1 vector are defined the same as described above.

The pharmaceutical composition may be a pharmaceutical composition for anticancer.

A disease may be cancer or tumor.

The term "cancer" refers to diseases caused by cells having aggressive characteristics in which cells divide and grow ignoring normal cell growth limit, invasive characteristics in which cells penetrate the surrounding tissues, and metastatic characteristics in which cells spread to other areas inside and outside the body. The cancer may be used in the same meaning as a malignant tumor or a tumor and may include a solid tumor and a blood born tumor. A type of the cancer is not limited.

The pharmaceutical composition may be used in combination with an existing cancer treatment substance (e.g., anticancer agent) to improve the cancer treatment efficacy. Examples of the anticancer agent may include a metabolic antagonist, an alkylating agent, a topoisomerase antagonist, a microtubule antagonist, an anticancer antibiotic, a plant-derived alkaloid, or an antibody anticancer or a molecular target anticancer agent, and, more specifically, taxol, nitrogen mustard, imatinib, oxaliplatin, rituximab, erlotinib, trastuzumab, gefitinib, bortezomib, sunitinib, carboplatin, sorafenib, bevacizumab, cisplatin, cetuximab, viscum album, asparaginase, tretinoin, hydroxycarbamide, dasatinib, estramastine, gemtuzumab ozogamycin, ibritumomab tucetan, heptaplatin, methylaminolevulinic acid, amsacrine, alemtuzumab, procarbazine, alprostadil, holmium nitrate chitosan, gemcitabine, doxyfluridine, pemetrexed, tegapur, capecitabine, gimeracil, oteracil, azacitidine, methotrexate, uracil, cytarabine, fluorouracil, fludarabine, enocitabine, decitabine, mercaptopurine, thioguanine, cladribine, carmophor, raltitrexed, docetaxel, paclitaxel, irinotecan, velotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pyrarubicin, aclarubicin, peflomycin, temozolomide, busulfan, ifosfamide, cyclophosphamide, melphalan, altretamine, dacarbazine, thiotepa, nimustine, chlorambucil, mitoractol, lomustine and carmustine, imatinib, gefitinib, ertotinib, tristuzumab, rosiletinib, necitumumab, everolimus, ramucirumab, dacomitinib, foretinib, pembrolizumab, ipilimumab, nivolumab, dabrafenib, veliparib, seritinib, carmustine, cyclophosphamide, ifosfamide, ixabepilone, melphalan, mercaptopurine, mitoxantrone, or TS1, but embodiments are not limited thereto.

The composition may be administered simultaneously, separately, or sequentially in combination with an immune checkpoint inhibitor. The "immune checkpoint" refers to proteins involved in inducing stimulation or suppression signals of an immune response on the surface of immune cells, where cancer cells control the system through the immune checkpoint so that stimulus of the immune response and inhibition of the cancer cells according to the stimulus may not normally function and thus evade the surveillance network of the immune system, that is, neutralize the anti-tumor immune response. The immune checkpoint inhibitor may include at least one selected from PD-1 (programmed cell death-1), PD-L1 (programmed cell death-ligand 1), PD-L2 (programmed cell death-ligand 2), CD27 (cluster of differentiation 27), CD28 (cluster of differentiation 28), CD70 (cluster of differentiation 70), CD80 (cluster of differentiation 80; also known as B7-1), CD86 (cluster of differentiation 86; also known as B7-2), CD137 (cluster of differentiation 137), CD276 (cluster of differentiation 276), killer-cell immunoglobulin-like receptors (KIRs), lymphocyte-activation gene 3 (LAG3), tumor necrosis factor receptor superfamily, member 4 (TNFRSF4; also known as CD134), glucocorticoid-induced TNFR-related protein (GITR), glucocorticoid-induced TNFR-related protein ligand (GITRL), 4-1BB ligand (4-1BBL), and cytolytic T lymphocyte associated antign-4 (CTLA-4) antagonists, but embodiments are not limited thereto.

The pharmaceutical composition may further include a pharmaceutically acceptable carrier or diluent. The pharmaceutically acceptable carrier or diluent may be known in the art. Examples of the carrier or diluent may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water (e.g. saline and sterile water), syrup, methyl cellulose, methylhydroxybenzoate, propylhydroxybenzoate, talc, magnesium stearate, mineral oil, Ringer's solution, buffer, maltodextrin solution, glycerol, ethanol, dextran, albumin, and a combination thereof. The pharmaceutical composition may further include a lubricant, a wetting agent, a sweetener, a flavoring agent, an emulsifier, a suspending agent, or a preservative.

According to methods that are known in the art, the pharmaceutical composition may be formulated and prepared in the form of a unit dose using the pharmaceutically acceptable carrier and/or diluents, or may be introduced and prepared in a multi-dose container. Here, the pharmaceutical composition may be formulated as a solution, suspension, syrup, or an emulsion of an oil or aqueous solvent. In some embodiments, the pharmaceutical composition may be formulated as extracts, powders, powdered drugs, granules, tablets, or capsules. The pharmaceutical composition may further include a dispersant or a stabilizer. The aqueous solvent may include physiological saline or a phosphate buffer solution (PBS). The pharmaceutical composition according to an embodiment may be formulated into in the form of an oral or parenteral administration, preferably, in the form of a parenteral administration. In general, a sterile solution of an active ingredient is prepared and a buffer for adjusting the pH is added to the solution for intramuscular, intraperitoneal, transdermal, and intravenous administration. For the intravenous administration, an isotonic agent may further be added to a preparation for isotonicity.

A prescribed dosage (effective amount) of the pharmaceutical composition may vary according to various factors such as formulation method, administration route, age, weight, and gender of a patient, pathological conditions, diet, duration of administration, route of administration, excretion rate, and susceptibility to reaction, and the dosage may be appropriately adjusted by those or ordinary skill in the art in consideration of these factors. Available administration routes may include parenteral administration (e.g., subcutaneous, intramuscular, intra-arterial, intraperitoneal, transdermal, or intravenous administration), topical administration (including transdermal administration), and injection, or insertion of or a transplantable device or a substance. As a target animal for therapy according to an embodiment, a human and a mammal of interest may be exemplified. For example, the target may be a human being, a monkey, a mouse, a rat, a rabbit, sheep, a cow, a dog, a horse, or a pig.

According to another aspect of an embodiment, provided is a method of inhibiting viability of cancer cells or tumor cells, the method including administering an effective amount of the recombinant HSV-1 or recombinant HSV-1 vector or a pharmaceutical composition including the recombinant HSV-1 or recombinant HSV-1 vector to a subject. The method may be a cancer treatment method.

The term "treatment" refers to or includes alleviating, inhibiting the progress of, or preventing a disease, disorder, or condition, or at least one symptom thereof, and the term "active ingredient" or "pharmaceutically effective amount" refers to an amount of a composition used while performing a process according to the present disclosure sufficient to alleviate, inhibit the progress of, or prevent the disease, disorder, or condition, or at least one symptom thereof.

The terms "administering", "introducing", and "transplanting" are interchangeably used and may refer to placement of a composition according to an embodiment into an individual by a method or route which results in at least partial localization of the composition at a desired site. The composition according to an embodiment may be administered by any appropriate route that delivers an active ingredient of the composition to a desired position in a living individual. The cells may survive for a short time, e.g., several hours to 24 hours or for a long time, e.g., several days to several years after administration into the individual.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, and the manner of administration, which may readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

Advantageous Effects of Disclosure

Since a recombinant HSV-1 according to an embodiment is prepared by simultaneously deleting ICP6 and IR regions, a relatively large foreign gene may be inserted or various foreign genes may be simultaneously inserted into the virus and thus may facilitate the genetic modification. Also, the recombinant HSV-1 is an oncolytic/anticancer virus having safe and excellent effects for killing cancer cells and thus may be widely used in the cancer treatment field.

BRIEF DESCRIPTION OF DRAWINGS

FIG. 10 shows graphs confirming anticancer effects and safety of the ΔICP6ΔIR virus, wherein FIG. 10A shows results confirmed from A549 cells; FIG. 10B shows results confirmed from U251N cells; FIG. 10C shows results confirmed from VERO cells; and FIG. 10D shows results confirmed from HswC cells.

MODE OF DISCLOSURE

Hereinafter, the present invention will be described in more detail with reference to Examples. However, these examples are for illustrative purposes only and the scope of the present invention is not limited to these examples.

Figure 1:
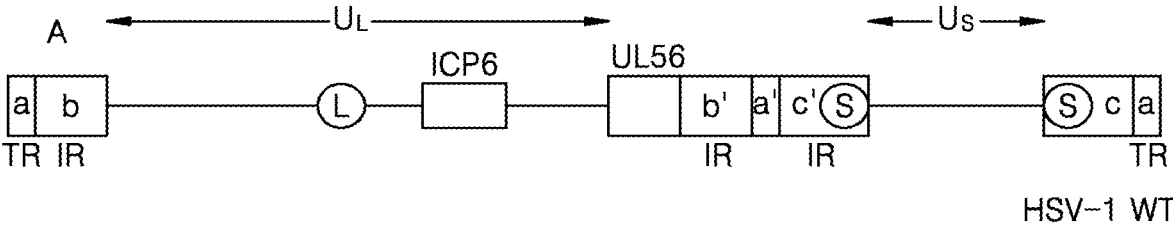
FIG. 1A is a schematic diagram of the genome of a wild-type human simplex virus type 1 (HSV-1 WT)
FIG. 1B is a schematic diagram of an infected-cell protein 6 (ICP6)-deleted (ΔICP6) HSV-1 genome.
FIG. 1C is a schematic diagram of an ICP6 and internal repeat (IR) regions-deleted (ΔICP6ΔIR) HSV-1 genome.
Figure 1:
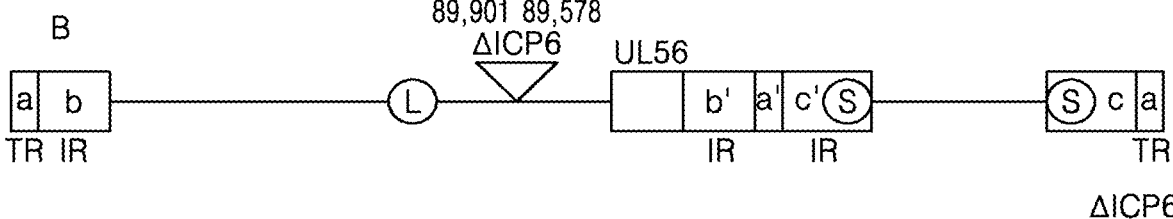
Figure 1:
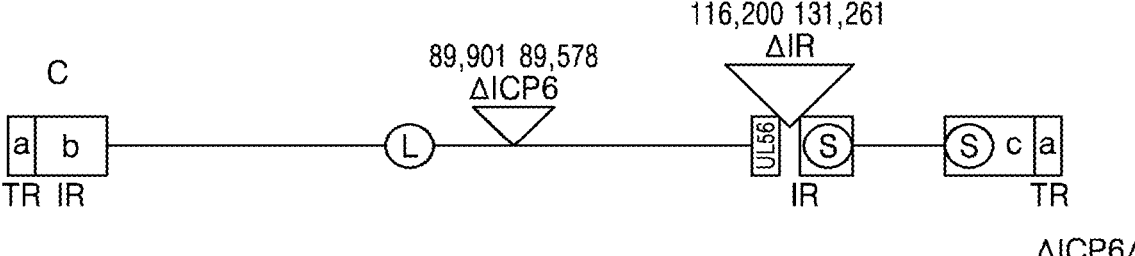

Example 1: Construction of Recombinant HSV-1 (ΔICP6ΔIR HSV-1) in which ICP6 and IR Regions are Deleted FIG. 1A is a schematic diagram of a genome of wild-type HSV-1. The HSV-1 genome is broadly categorized into a unique long (UL) region and a unique short (US) region. The UL region has a single replication origin; a and b composed of a terminal repeat (TP) and an internal repeat (IR) at the 5' end; and a and b in the reverse direction at the 3' end. The US region has two replication origins; a c sequence in the reverse direction at the 5' end; forwarding c is repeated at the 3' end; and a sequence is repeated once more at the 3' end.

First, ΔICP6 HSV-1 in which a part of the ICP6 region is deleted is prepared from a genomic sequence of the HSV-1 WT. The nucleotides 86,364 to 89,777 in the wild-type HSV-1 genome sequence constitute a sequence encoding the ICP6 gene. The nucleotides 86,901 to 89,578, which are a part of the ICP6 gene, were deleted using a method known in the art, and this was names as "ΔICP6 HSV-1 virus."

FIG. 1B is a schematic diagram of an ICP6-deleted (ΔICP6) HSV-1 genome.

Next, ΔICP6ΔIR virus from which the ICP6 and IR regions are deleted was constructed using the ΔICP6 HSV-1 virus as a template. In the wild-type HSV-1 genome sequence, the nucleotides 116,141 to 116,846 constituted a UL56 sequence, and the IR region was broadly composed of b'(117,080 to 125,845), a'(125,846 to 126,240), and c'(126, 241 to 132,463). In this region, the nucleotides 116,200 to 131,261 corresponding to a partial region of UL56 gene to a partial region of IR region were deleted using a method known in the art. This was named "ΔICP6ΔIR HSV-1 virus." FIG. 1C is a schematic diagram of an ICP6 and IR regions-deleted (ΔICP6ΔIR) HSV-1 genome.

Example 2: Construction of ΔICP6-ΔIR-rpsL-Neo to which Foreign Gene rpsL-Neo is Inserted A foreign gene, 1319 bp, which is an rpsL-neo gene, was inserted to the ΔICP6ΔIR HSV-1 of Example 1, from which the ICP6 gene and the IR gene were simultaneously deleted, to construct a virus, and the insertion of the foreign gene of the virus was evaluated.

In particular, as shown in Table 1, a UL56-rpsL-neo primer having a sequence complementary to UL56 and rpsL-neo and a UsIR-rpsL-neo primer having a sequence complementary to UsIR and rpsL-neo were prepared. After adding a 2× green master mix (thermo scientific) reaction enzyme to 10 pmol of the UL56-rpsL-neo primer and the UsIR-rpsL-neo primer, PCR was performed with 200 ng of the rpsL-neo gene as a template. The PCR product was transformed into DH10b *Escherichia coli* together with the ΔICP6 total vector of Example 1 to induce homologous recombination to prepare ΔICP6-ΔIR-rpsL-neo expressing rpsL-neo.

Figures 2, 3:
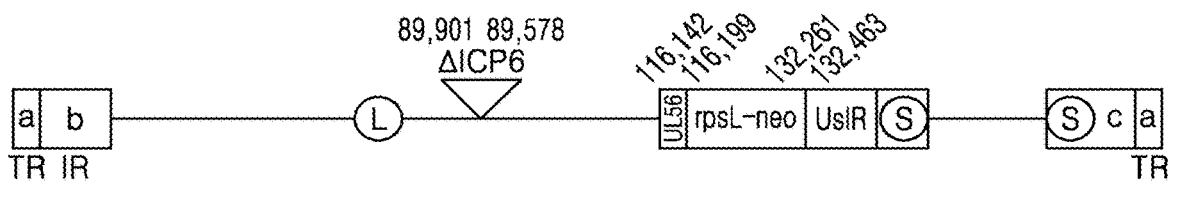
FIG. 2 is a schematic diagram illustrating an rpsL-neo gene and positions of a UL56-rpsL-neo primer and a UsIR-rpsL-neo primer.
FIG. 3 is a schematic diagram of ΔICP6-ΔIR-rpsL-neo.

FIG. 2 is a schematic diagram that shows positions of the rpsL-neo gene, the UL56-rpsL-neo primer, and the UsIR-rpsL-neo primer.

FIG. 3 is a schematic diagram of ΔICP6-ΔIR-rpsL-neo.

TABLE 1

| Primer name | SEQ ID NO. | Sequence |
|---|---|---|
| UL56-rpsL-neo | 5 | 5'-acaggaataccagaataatgaccaccacaatcgcgaccaccccaaatacaGGCCTGGTGATGATGGGGGATCG-3' (underline: sequence complementary to UL56, bold: sequence complementary to rpsL-neo) |
| UsIR-rpsL-neo | 6 | 5'-cccgaggacgccccgatcgtccacacggagcgcggctgccgacacggatcTCAGAAGAACTCGTCAAGAAGGCG-3' (bold: sequence complementary to rpsL-neo, underline: sequence complementary to UsIR) |

PCRs were performed using the PCR primers in Table 2 to evaluate production of the homologous recombination. Conditions of each of the PCRs were as follows. After adding a 2× green master mix (thermo scientific) reaction enzyme to 10 pmol of the UL55 S primer and the UsIR-rpsL-neo AS primer, each of the PCRs was performed with 200 ng of the rpsL-neo gene as a template; and denaturing the resultant at 95° C. for 30 seconds, annealing at 58° C. for 30 seconds, and extending at 72° C. for 2 minutes in the PCR machine (Bio-rad). To confirm rpsL-neo and glycoprotein C, PCR was performed under conditions denaturing the resultant at 95° C. for 30 seconds, annealing at 58° C. for 30 seconds, and extending at 72° C. for 30 seconds at the same mixture ratio.

TABLE 2

| Primer name | SEQ ID NO. | Sequence (5' → 3') |
|---|---|---|
| UL55 S | 7 | ACGCGTCGACtaaaaacaaaacatttcaa acaaatcgcccca |
| UsIR-rpsL neo AS | 8 | cccgaggacgccccgatcgtccacacgga gcgcggctgccgacacggatcTCAGAAGA ACTCGTCAAGAAGGCG |
| rpsL neo S | 9 | CGGCATCGCCCTAAAATTCGGCGTCCTC |
| rpsL neo AS | 10 | AAGAACCGGGCGCCCCTGCGCTGACAGC |
| gC S | 11 | CAGATCCGATGCCGGTTTCGGAATTCCAC CCG |
| gC AS | 12 | CGGGTTAAACACCTGGCGGTCGTCCTCGA AC |
| ICP6 R-rpsL-neo S | 13 | GTTCCTGTCGCGACACACGGCGCCGCTCT GCGGTATTCGGGGGGGAGGGGGGCCTGGT GATGATGGCGGGATCG |
| ICP6 R-rpsL-neo AS | 14 | AGGGTCCCGTCCGCCTTCTCCGTGACATA CAGGGTCATGGATTGGCTATGTCAGAAGA ACTCGTCAAGAAGGCG |

Figure 4:
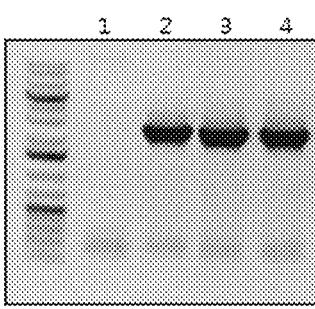
FIG. 4 shows results of performing polymerase chain reaction (PCR) performed using a UL55 S primer and a UsIR-rpsL neo AS primer to confirm insertion of rpsL-neo, wherein HSV-1 WT was used as a negative control, and ΔICP6-rpsL-neo was used as a positive control.
Figure 5:
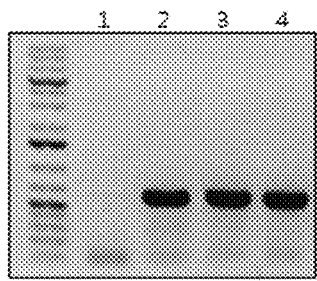
FIG. 5 shows results of PCR performed using an rpsL neo S primer and an rpsL neo AS primer to confirm insertion of rpsL-neo, wherein HSV-1 WT was used as a negative control, and ΔICP6-rpsL-neo was used as a positive control.

FIG. 4 shows the results of PCR performed using a UL55 S primer and a UsIR-rpsL neo AS primer to confirm insertion of rpsL-neo. HSV-1 WT was used as a negative control, and ΔICP6-rpsL-neo was used as a positive control. After adding a 2× green master mix (thermo scientific) reaction enzyme to 10 pmol of an ICP6 R-rpsL-neo S primer and an ICP6 R-rpsL-neo AS primer, PCR was performed with 200 ng of ΔICP6-rpsL-neo as a template in the PCR machine (Bio-rad) under the conditions of denaturing the resultant at 95° C. for 30 seconds, annealing at 58° C. for 30 seconds, and extending at 72° C. for 1 minute and 30 seconds. The PCR products of rpsL-neo was transformed into DH10b *E. coli* together with the wild-type HSV-1 total vector to induce homologous recombinant to prepare ΔICP6-rpsL-neo. As a result, it was confirmed that the homologous recombinant was successfully achieved since a band of 2300 bp of the prepared ΔICP6-ΔIR-rpsL-neo was confirmed the same with that of the positive control. FIG. 5 shows the results of PCR performed using an rpsL neo S primer and an rpsL neo AS primer to confirm insertion of rpsL-neo. HSV-1 WT was used as a negative control, and ΔICP6-rpsL-neo was used as a positive control. As a result, it was confirmed that the homologous recombinant was successfully achieved since a band of 534 bp of the prepared ΔICP6-ΔIR-rpsL-neo was confirmed the same with that of the positive control.

Figure 6:
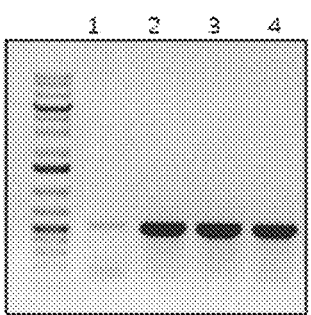
FIG. 6 shows results of PCR performed using a gC S primer and a gC AS primer that are used for detecting glycoprotein C to confirm insertion of rpsL-neo, wherein HSV-1 WT was used as a negative control, and ΔICP6-rpsL-neo was used as a positive control.

FIG. 6 shows the results of PCR performed using a gC S primer and a gC AS primer for detecting glycoprotein C to confirm insertion of rpsL-neo. HSV-1 WT was used as a negative control, and ΔICP6-rpsL-neo was used as a positive control. As a result, it was confirmed that homologous recombination was successfully achieved since a band of 512 bp of the prepared ΔICP6-ΔIR-rpsL-neo was confirmed the same with that of the positive control.

Therefore, it was confirmed that the rpsL-neo gene, a foreign gene, was successfully inserted to the ΔICP6ΔIR virus.

Example 3: Construction of ΔICP6ΔIR Virus

The rpsL-neo gene, a foreign gene, was deleted from the ΔICP6-ΔIR-rpsL-neo prepared in Example 2 to prepare ΔICP6ΔIR virus.

In particular, after preparing the primers in Table 3, a primer annealing method was performed to prepare a two-stranded oligomer having a complementary sequence bound thereto. The prepared oligomer was transformed into DH10b *E. coli* together with the ΔICP6-ΔIR-rpsL-neo total vector of Example 2 to induce homologous recombination to prepare dICP6-dIR.

TABLE 3

| Primer name | SEQ ID NO. | Sequence (5' -> 3') |
|---|---|---|
| ΔIR S | 15 | ACAGGAATACCAGAATAATGACCACCACAATCGCG ACCACCCCAAATACAGATCCGTGTCGGCAGCCGCG CTCCGTGTGGACGATCGGGGCGTCCTCG |
| ΔIR AS | 16 | CGAGGACGCCCCGATCGTCCACACGGAGCGCGGCT GCCGACACGGATCTGTATTTGGGGTGGTCGCGATT GTGGTGGTCATTATTCTGGTATTCCTGT |

Figure 7:
FIG. 7 shows results of PCR performed using a UL55 S primer and a AIR AS primer to confirm whether the IR region was well deleted from the ΔICP6ΔIR virus, wherein a AIR virus was used as a positive control.

To confirm whether the ΔICP6ΔIR virus from which the foreign gene was deleted was successfully constructed or not, PCR was performed using the PCR primers above. After adding a 2× green master mix (thermo scientific) reaction enzyme to 10 pmol of a UL55 S primer and an ΔIR AS primer, PCR was performed with 200 ng of ΔICP6ΔIR as a template in the PCR machine (Bio-rad) under the conditions of denaturing the resultant at 95° C. for 30 seconds, annealing at 58° C. for 30 seconds, and extending at 72° C. for 1 minute. To confirm rpsL-neo, PCR was performed under conditions denaturing the resultant at 95° C. for 30 seconds, annealing at 58° C. for 30 seconds, and extending at 72° C. for 30 seconds at the same mixture ratio. FIG. 7 shows the results of PCR performed using a UL55 S primer and a ΔIR AS primer to confirm whether IR was well removed from the ΔICP6ΔIR virus. A ΔIR virus was used as a positive control. After adding a 2X green master mix (thermo scientific) reaction enzyme to 10 pmol of a UL56-rpsL-neo primer and a UsIR-rpsL-neo primer, PCR was performed with 200 ng of the ΔIR virus as a template in the PCR machine (Bio-rad) under the conditions of denaturing the resultant at 95° C. for 30 seconds, annealing at 58° C. for 30 seconds, and extending at 72° C. for 1 minute. The PCR products of rpsL-neo was transformed into DH10b *E. coli* together with a wild-type HSV-1 total vector to induce homologous recombination to prepare a ΔIR-rpsL-neo virus. Then, after performing primer annealing on the ΔIR S and ΔIR AS primers, the primers were transformed into DH10b *E. coli* together with a ΔIR-rpsL-neo total vector to induce homologous recombination to prepare a ΔIR virus.

As a result, it was confirmed that IR was successfully removed since a band of a size of 1 kb of the prepared ΔICP6ΔIR virus was confirmed the same with that of the positive control.

Figure 8:
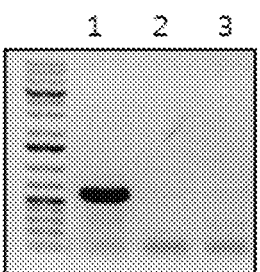
FIG. 8 shows results of PCR performed using a rpsL-neo S primer and an rpsL-neo AS primer to confirm whether foreign gene rpsL-neo was well deleted from the ΔICP6ΔIR virus, wherein ΔICP6-ΔIR-rpsL-neo was used as a control.

FIG. 8 shows the results of PCR to confirm whether a foreign gene, rpsL-neo, was well removed from an ICP6ΔIR virus by performing PCR using an rpsL-neo S primer and an rpsL-neo AS primer. The ΔICP6-ΔIR-rpsL-neo prepared in Example 2 was used as a control. As a result, unlike the control, ΔICP6-ΔIR-rpsL-neo, exhibited a band of about 500 bp, the ΔICP6ΔIR virus did not exhibit a band, and this confirms that the foreign gene, rpsL-neo, was successfully deleted.

Figure 9:
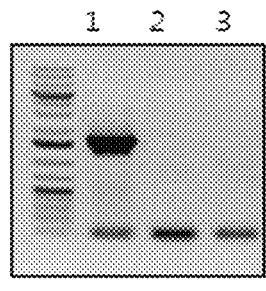
FIG. 9 shows results of PCR performed using a UL55 S primer and an rpsL-neo S AS primer to confirm whether IR and rpsL-neo were well deleted from the ΔICP6ΔIR virus, wherein ΔICP6-ΔIR-rpsL-neo was used as a control.
Figure 10:
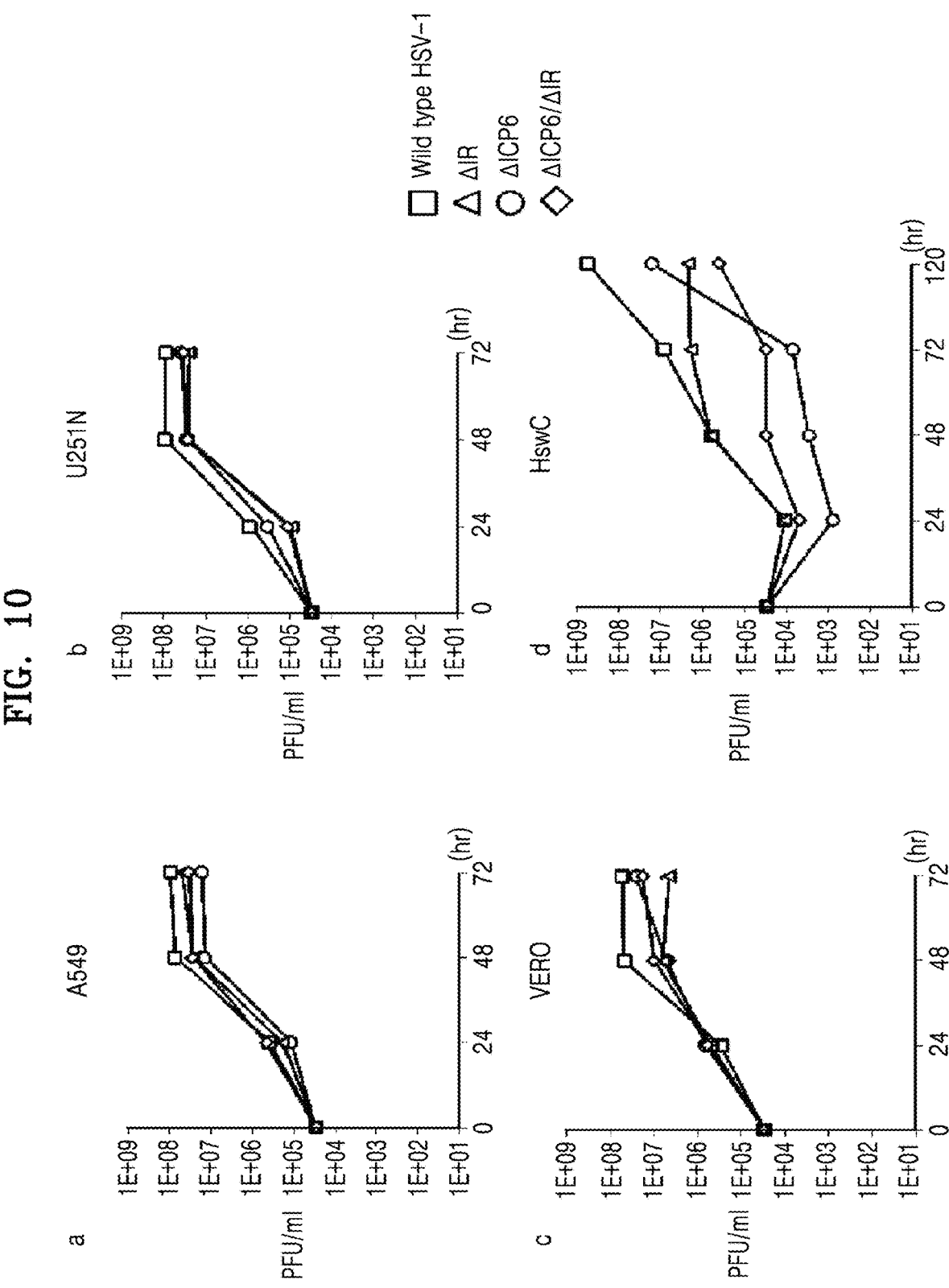

FIG. 9 shows the results of PCR performed using a UL55 S primer and an rpsL-neo S AS primer to confirm whether IR and rpsL-neo were well removed from the ICP6ΔIR virus. The ΔICP6-ΔIR-rpsL-neo prepared in Example 2 was used as a control. As a result, unlike the control, ΔICP6-ΔIR-rpsL-neo, generated a band of about 1700 bp, the ΔICP6ΔIR virus did not generate a band, and this confirms that the IR and foreign gene were successfully deleted.

Thus, it confirms that the ΔICP6ΔIR virus with the foreign gene removed therefrom was successfully prepared.

Experimental Example 1: Confirmation of anticancer effects and safety of ΔICP6ΔIR virus of Example 3

A549 (human lung cancer, ATCC® CRM-CCL-185TM), U251N (human glioma, ATCC®), and VERO (monkey normal kidney, ATCC® CCL-81™) cells were divided into a 6-well plate at a density of $3.5 \times 10^5$ cells/well, and HswC (iXcells, 10HU-188) cells were divided at a density of $3 \times 10^5$ cells/well. After 24 hours, each of a wild-type HSV-1, a ΔICP6 virus from which only ICP6 is deleted, a AIR virus from which only IR is deleted, and a ΔICP6ΔIR virus from which both ICP6 and IR are deleted was infected with 0.1 MOI.

After 24 hours, 48 hours, 72 hours, and 120 hours, the cells and the supernatants were all collected and centrifuged at 4° C. for 10 minutes at 3000 rpm. Thus obtained pellets and the supernatants were separated, and the supernatants were remained at 4° C., and after freezing/thawing the pellets three times, the supernatants were added with the pellets, and the resultants were centrifuged once again at 4° C. for 10 minutes at 3000 rpm. Thereafter, only the supernatants were separated and a plaque assay was performed as follows.

VERO cells divided into a 12-well plate at a density of $1.5 \times 10^5$ were infected with the supernatants obtained as described above. After 8 hours, 1 ml of 1% methylcellulose was added to the cells. 3 days after the infection, the cells were dyed with 1% crystal violet staining solution to count the number of plaques.

As a result, it was confirmed that ΔICP6ΔIR showed cancer cell killing ability similar to that of wild-type virus HSV-1 and cancer cell killing ability higher than that of ΔICP6 or AIR. Also, progeny virus of low titer was produced in HswC cells, showing the characteristics of a vector that is safe for humans.

The invention claimed is:

1. A recombinant herpes simplex virus type 1 (HSV-1) strain KOS, comprising:

an HSV-1 genome, in which an infected-cell protein 6 (ICP6) region among genomic regions of HSV-1 is deleted, and the nucleotide sequence of SEQ ID NO:2 among nucleotide sequences of the internal repeat (IR) region between a unique long (UL) region and a unique short (US) region is deleted, wherein the recombinant HSV-1 is replication-competent and is an oncolytic virus that activates immune cells by exposing antigens of cancer cells by specifically killing cancer cells, wherein the simultaneous deletion of ICP6 and a nucleotide sequence of SEQ ID NO:2 enhances the ability to selectively kill cancer cells, and wherein the cancer is lung cancer or glioma.

2. The recombinant HSV-1 of claim 1, comprising:

a terminal repeat of a long (TRL) region;

a UL region comprising a nucleotide sequence of at least one gene selected from the group consisting of UL1 to UL38 and UL40 to UL56;

a US region comprising a nucleotide sequence of at least one gene selected from the group consisting of US1 to US12;

a terminal repeat of a short (TRS) region, or a combination thereof, as a genomic region.

3. The recombinant HSV-1 of claim 1, wherein the ICP6 region is a UL39 gene.

4. The recombinant HSV-1 of claim 1, having a genome in which the nucleotide sequence of SEQ ID NO: 1 among nucleotide sequences of HSV-1 and ICP6 genes is deleted.

5. The recombinant HSV-1 of claim 1, wherein the IR region comprises an internal repeat of a long (IRL) region and an internal repeat of a short (IRS) region.

6. The recombinant HSV-1 of claim 1, wherein a part of a nucleotide sequence of a UL56 gene is additionally deleted, as a deleted part of the nucleotide sequence of the UL56 gene.

7. The recombinant HSV-1 of claim 6, wherein the deleted part of the nucleotide sequence of the UL56 gene is the nucleotide sequence of SEQ ID NO: 3.

8. The recombinant HSV-1 of claim 1, comprising:

the nucleotide sequence of SEQ ID NO: 4.

9. The recombinant HSV-1 of claim 1, exhibiting cancer cell or tumor cell specificity.

10. A recombinant HSV-1 vector, comprising:

a genome nucleotide sequence of the recombinant HSV-1 of claim 1.

11. The 1 vector of claim 10, further comprising:

a nucleotide sequence of a foreign gene.

12. A method of preparing a recombinant HSV-1 strain KOS, wherein the recombinant HSV-1 is replication-competent and is an oncolytic virus that activates immune cells by exposing antigens of cancer cells by specifically killing cancer cell, the method comprising:

preparing a recombinant HSV-1 vector comprising a genome nucleotide sequence of HSV-1 strain KOS, in which an ICP6 region and the nucleotide sequence of SEQ ID NO:2 among nucleotide sequences of the IR region are deleted; and transfecting cells with the vector to obtain a recombinant HSV-1, wherein the simultaneous deletion of ICP6 and a nucleotide sequence of SEQ ID NO:2 enhances the ability to selectively kill cancer cells, and wherein the cancer is lung cancer or glioma.

13. The method of claim 12, wherein the recombinant HSV-1 vector comprises:

a TRL region;

a UL region comprising a nucleotide sequence of at least one gene selected from the group consisting of UL1 to UL38 and UL40 to UL56;

a US region comprising a nucleotide sequence of at least one gene selected from the group consisting of US1 to US12;

a TRS region, or a combination thereof.

14. A method of treating lung cancer or glioma, the method comprising:

administering an effective amount of the recombinant HSV-1 of claim 1 to a subject in need thereof, thereby treating the lung cancer or glioma.

15. A method of treating lung cancer or glioma, the method comprising:

administering an effective amount of the vector of claim 10 to a subject in need thereof, thereby treating the lung cancer or glioma.

* * * * *

SEQUENCE LISTING

```
<160> NUMBER OF SEQ ID NOS: 16

<210> SEQ ID NO 1
<211> LENGTH: 2678
<212> TYPE: DNA
<213> ORGANISM: Artificial Sequence
<220> FEATURE:
<223> OTHER INFORMATION: deleted ICP6

<400> SEQUENCE: 1
gatcccgtcg gccccgcgga gttcgtctcg gacgaccggt cgtccgattc cgactcggat       60
gactcggagg acaccgactc ggagacgctg tcacacgcct cctcggacgt gtccggcggg      120
gccacgtacg acgacgccct tgactccgat tcgtcatcgg atgactccct gcagatagat      180
ggccccgtgt gtcgcccgtg gagcaatgac accgcgcccc tggatgtttg ccccgggacc      240
cccggcccgg gcgccgacgc cggtggtccc tcagcggtag acccacacgc accgacgcca      300
ggggccggcg ctggtcttgc ggccgatccc gccgtggccc gggacgacgc ggaggggctt      360
tcggaccccc ggccacgtct gggaacgggc acggcctacc ccgtccccct ggaactcacg      420
cccgagaacg cggaggccgt ggcgcgcttt ctgggagatg ccgtgaaccg cgaacccgcg      480
ctcatgctgg agtacttttg ccggtgcgcc cgcgaggaaa ccaagcgtgt ccccccagg      540 acattctgca gccccctcg cctcacggag gacgactttg ggcttctcaa ctacgcgctc      600
gtggagatgc agcgcctgtg tctggacgtt cctccggtcc tgccgaacgc atacatgccc      660
tattatctca gggagtatgt gacgcggctg gtcaacgggt tcaagccgct ggtgagccgg      720
tccgctcgcc tttaccgcat cctgggggtt ctggtgcacc tgcggatccg gacccgggag      780
gcctcctttg aggagtggct gcgatccaag gaagtggccc tggactttgg cctgacggaa      840
aggcttcgcg agcacgaagc ccagctggtg atcctggccc aggctctgga ccattacgac      900
tgtctgatcc acagcacacc gcacacgctg gtcgagcggg ggctgcaatc ggccctgaag      960
tatgaggagt tttacctaaa gcgctttggc gggcactaca tggagtccgt cttccagatg     1020
tacacccgca tcgccggctt tttggcctgc cgggccacgc gcggcatgcg ccacatcgcc     1080
```

```
ctggggcgag aggggtcgtg gtgggaaatg ttcaagttct ttttccaccg cctctacgac      1140
caccagatcg taccgtcgac ccccgccatg ctgaacctgg ggacccgcaa ctactacacc      1200
tccagctgct acctggtaaa cccccaggcc accacaaaca aggcgaccct gcgggccatc      1260
accagcaacg tcagcgccat cctcgcccgc aacgggggca tcgggctatg cgtgcaggcg      1320
tttaacgact ccggccccgg gaccgctagc gtcatacccg ccctcaaggt cctcgactcg      1380
ctggtggcgg cgcacaacaa agagagcgcg cgtccaaccg gcgcgtgcgt gtacctggag      1440
ccgtggcaca ccgacgtgcg ggccgtgctc cggatgaagg gggtcctcgc cggcgaagag      1500
gcccagcgct gcgacaatat cttcagcgcc ctctggatgc cagacctgtt tttcaagcgc      1560
ctgattcgcc acctggacgg cgagaagaac gtcacatgga ccctgttcga ccgggacacc      1620
agcatgtcgc tcgccgactt tcacggggag gagttcgaga agctctacca gcacctcgag      1680
gtcatggggt tcggcgagca gatacccatc caggagctgg cctatggcat tgtgcgcagt      1740
gcggccacga ccgggagccc cttcgtcatg ttcaaagacg cggtgaaccg ccactacatc      1800
tacgacaccc aggggggcggc catcgccggc tccaacctct gcaccgagat cgtccatccg      1860
gcctccaagc gatccagtgg ggtctgcaat ctgggaagcg tgaatctggc ccgatgcgtc      1920
tccaggcaga cgtttgactt tgggcggctc cgcgacgccg tgcaggcgtg cgtgctgatg      1980
gtgaacatca tgatcgacag cacgctacaa cccacgcccc agtgcacccg cggcaacgac      2040
aacctgcggt ccatgggaat cggcatgcag ggcctgcaca cggcctgcct gaagctgggg      2100
ctggatctgg agtctgtcga atttcaggac ctgaacaaac acatcgccga ggtgatgctg      2160
ctgtcggcga tgaagaccag caacgcgctg tgcgttcgcg gggcccgtcc cttcaaccac      2220
tttaagcgca gcatgtatcg cgccggccgc tttcactggg agcgctttcc ggacgcccgg      2280
ccgcggtacg agggcgagtg ggagatgcta cgccagagca tgatgaaaca cggcctgcgc      2340
aacagccagt ttgtcgcgct gatgcccacc gccgcctcgg cgcagatctc ggacgtcagc      2400
gagggctttg ccccctgtt caccaacctg ttcagcaagg tgacccggga cggcgagacg      2460
ctgcgcccca acacgctcct gctaaaggaa ctggaacgca cgtttagcgg gaagcgcctc      2520
ctggaggtga tggacagtct cgacgccaag cagtggtccg tggcgcaggc gctcccgtgc      2580
ctggagccca cccacccct ccggcgattc aagaccgcgt ttgactacga ccagaagttg      2640
ctgatcgacc tgtgtgcgga ccgcgccccc tacgtcga                             2678
```

<210> SEQ ID NO 2
<211> LENGTH: 14182
<212> TYPE: DNA
<213> ORGANISM: Artificial Sequence
<220> FEATURE:
<223> OTHER INFORMATION: deleted IR

<400> SEQUENCE: 2

```
cccctctccc cccctctccc ctctcccccc ctctcccctc tcccccctc tccctctcc          60 ccccctctcc cctctccccc cctctcccct ctcccccct ctccctctc cccccctctc        120 ccctctcccc ccctctcccc tctcccccc tctcccctct cccccctct ccctgctct        180 ttccccgtga cacccgacgc tggggggcgt ggctgccggg aggggccgcg tatgggcggg       240
cctactcggt ctcccgcccc cccgaaccgc cccgccggct ttgccccct ttgatccct        300 gctaccccca ccccgtgctc gtggtgcggg gtgggggat gtgggcgggg gtgcgcggga       360
ggtgtcggtg gtgggggtgg tggtggtggt ggtagtagga atggtggtgg gggggagggc       420
```

```
gctggttggt caaaaaaggg agggacgggg gccggcagac cgacggcgac aacgctcccc    480
ggcggccggg tcgcggctct tacgagcggc ccggcccgcg ctcccacccc ccgggccgtg    540
tccttgcttt cccccccgtct cccccccccgc cttctcctcc tcctcctcgt ttttccaaac   600
cccgcccacc cggcccggcc cggccggcc cggccaccgc cgcccaccca cccacctcgg      660
gatacccagc cccggtcccc cgttccccgg gggccgttat ctccagcgcc ccgtccggcg    720
cgccgccccc cgccgctaaa ccccatcccg cccccgggac cccacatata agcccccagc    780
cacacgcaag aacagacacg cagaacggct gtgtttattt taaataaacc gatgtcggaa    840
taaacaaaca caaacacccg cgacggggggg acggagggga cggagggagg ggggtgacgg    900
gggacggaaa cagacacaaa aaacaaccac aaaaaacaac cacccaccga caccccacc     960 ccagtctcct cgccttctcc cacccacccc acgcccccac tgagcccggt cgatcgacga   1020 gcaccccgc ccacgcccc gccctgccc cggcgacccc cggcccgcac gatcccgaca     1080
acaataacaa ccccaacgga aagcggcggg gtgttggggg aggcgaggaa caaccgaggg   1140 gaacgggga tggaaggacg ggaagtggaa gtcctgatac ccatcctaca cccccctgcc    1200
ttccaccctc cggccccccg cgagtccacc cgccggccgg ctaccgagac cgaacacggc   1260
ggccaccgcc gccgccgccg ccgacaccgc agagccggcg cgcgcacaca caagcggcag   1320
aggcagaaag gcccccgagtc attgtttatg tggccgcggg ccagcagacg gcccgcgaca   1380 ccccccccg cccgtgtggg tatccggccc cccgccccgc gccggtccat taagggcgcg    1440
cgtgcccgcg agatatcaat ccgttaagtg ctctgcagac aggggcaccg cgcccggaaa    1500
tccattaggc cgcagacgag gaaaataaaa ttacatcacc tacccatgtg gtgctgtggc   1560 ctgttttttgc tgcgtcatct gagcctttat aaaagcgggg gcgcggccgt gccgatcgcc   1620
ggtggtgcga aagactttcc gggcgcgtcc gggtgccgcg gctctccggg cccccctgca   1680
gccggggcgg ccaaggggcg tcggcgacat cctcccccta agcgccggcc ggccgctggt   1740
ctgttttttc gttttccccg tttcggggggt ggtgggggtt gcggtttctg tttctttaac   1800 ccgtctggggg tgttttttcgt tccgtcgccg gaatgtttcg ttcgtctgtc ccctcacggg   1860
gcgaaggccg cgtacggccc gggacgaggg gcccccgacc gcggcggtcc gggccccgtc   1920
cggacccgct cgccggcacg cgacgcgaaa aaggccccccc ggaggctttt ccgggttccc   1980
ggcccggggc ctgagatgaa cactcggggt taccgccaac ggccggcccc cgtggcggcc   2040 cggcccggggg ccccggcgga cccaaggggc cccggcccgg ggccccacaa cggcccggcg    2100
catgcgctgt ggttttttttt tcctcggtgt tctgccgggc tccgtcgcct ttcctgttct    2160
cgcttctccc cccccccctt cacccccagt accctcctcc ctcccttcct ccccgttat     2220 cccactcgtc gagggcgccc cggtgtcgtt caacaaagac gccgcgtttc caggtaggtt    2280
agacacctgc ttctccccaa tagaggggggg gggacccaaa cgacaggggg cgccccagag   2340
gctaaggtcg gccacgccac tcgcgggtgg gctcgtgtta cagcacacca gcccgttatt    2400 ttcccccccct cccaccctta gttagactct gttacttacc cgtccgacca ccaactgccc   2460
ccttatctaa gggccggctg gaagaccgcc aggggtcgg ccggtgtcgc tgtaaccccc     2520
cacgccaatg acccacgtac tccaagaagg catgtgtccc acccgcctg tgttttttgtg    2580 cctggctctc tatgcttggg tcttactgcc tggggggggg gagtgcgggg gaggggggggg   2640 gtgtggaagg aaatgcacgg cgcgtgtgta ccccccccta aagttgttcc taaagcgagg   2700
atatggagga gtggcgggtg ccggggggacc ggggtgatct ctggcacgcg ggggtgggaa   2760
gggtcggggg aggggggggat ggggtaccgg cccacctggc cggcgcgggt gcgcgtgcct   2820
```

```
ttgcacacca accccacgtc ccccggcggt ctctaagaaa caccgccccc cctccttcat    2880
accaccgagc atgcctgggt gtgggttggt aaccaacacg cccatccct cgtctcctgt    2940 gattctctgg ctgcaccgca ttcttgtttt ctaactatgt tcctgtttct gtctcccccc    3000 ccaccccctcc gccccacccc ccaacaccca cgtctgtggt gtggccgacc cccttttggg    3060
cgccccgtcc cgccccgcta cccctcccat cctttgttgc cctatagtgt agttaacccc    3120
cccccccgcc ctttgtggcg gccagaggcc aggtcagtcc gggcgggcag gcgctcgcgg    3180
aaacttaaca cccacaccca acccactgtg gttctggctc catgccagtg gcaggatgct    3240
ttcggggatc ggtggtcagg cagcccgggc cgcggctctg tggttaacac cagagcctgc    3300
ccaacatggc accccactc ccacgcaccc ccactcccac gcacccccac tcccacgcac    3360
ccccactccc acgcaccccc actcccacgc accccactc ccacgcaccc ccactcccac    3420 gcaccccac tcccacgcac ccccactccc acgcaccccc gcgatacatc caacacagac    3480
agggaaaaga tacaaaagta aacctttatt tcccaacaga cagcaaaaat cccctgagtt    3540 tttttttatta gggccaacac aaaagacccg ctggtgtgtg gtgcccgtgt ctttcacttt    3600
ccacctcccc gacacggatt ggctggtgta gtgggcgcgg ccagagacca cccagcgccc    3660
gacccccccc tccccacaaa cacgggggcg tcccttattg ttttccctcg tcccgggtcg    3720 acgcccctg ctccccggac cacgggtgcc gagaccgcag gctgcggaag tccagggcgc    3780
ccactagggt gccctggtcg aacagcatgt tccccacggg ggtcatccag aggctgttcc    3840
actccgacgc gggggccgtc gggtactcgg ggggcgtcac gtggttaccc gcggtctcgg    3900
ggagcagggt gcggcggctc cagccgggga ccgcggcccg cagccgggtc gccatgtttc    3960
ccgtctggtc caccaggacc acgtacgccc cgatgttccc cgtctccatg tccaggatgg    4020
gcaggcagtc ccccgtgatc gtcttgttca cgtaaggcga cagggcgacc acgctagaga    4080
cccccgagat gggcaggtag cgcgtgaggc cgcccgcggg gacggccccg gaagtctccg    4140
cgtggcgcgt cttccgggca cacttcctcg gccccgcgg cccagaagca gcgcgggggc    4200
cgagggaggt ttcctcttgt ctccctccca gggcaccgac ggccccgccc gaggaggcgg    4260
aagcggagga ggacgcggcc ccggtggcgg aagaggtggc ccccgcggga gtcggggccg    4320
aggaggaaga ggcggaggag gaagaggcgg aggccgccga ggacgtcagg ggggtcccgg    4380
gccctccctg gccgcgcccc cccggccctg agtcggaggg ggggtgcgtc gccgccctct    4440
tggcccctgc cggcgcgagg gggggacgcg tggactgggg ggaggggttt tcctggcccg    4500
acccgcgcct cttcctcgga cgcaccgcg cctcctgctc gacagaggcg gcggagggga    4560 gcggggggc gccggagggg gcggcgccgg aggggcggc gccgcgggag ggcccgtgtc    4620
caccctccac gcccggcccc cccgagccgc gcgccaccgt cgcacgcgcc cggcacagac    4680
tctgttcttg gttcgcggcc tgagccaggg acgagtgcga ctggggcaca cggcgcgcgt    4740
ccgcggggcg ggcggccggc tccgccccgg gggccgggc gcggggccg ggccccggag    4800 gcggcgcccg cacacacggg gccacggccg cgcggggcg cgcggggccc gacgcggccg    4860
cggacgcggg gggaccgggg cggggggcgg agcctggcat gggcgccgcg gggggcctgt    4920
ggggagaggc cggggggggag tcgctgatca ctatgggtc tctgttgttt gcaagggggg    4980
cgggtctgtt gacaaggggg cccgtccggc ccctcggccg ccccgcctcc gcttcaacaa    5040
ccccaacccc cccggagggg ccagacgccc cccgcggcac cgcggctcgc gactggcggg    5100
agccgccgcc gccgctgctg ttggtggtgg tgttagtgtt actgctgccg tgtggcccga    5160
```

-continued

```
tgggcgccga gggggcgct  gtccgagccg  cggccggctg  gggggctgcg  tgagacgccc      5220
cgcccgtcac ggggggcgcg  gcggcgcctc  tgcgtggggg  ggcgcggggc  gtccggcggg      5280
gggcgggcgg tacgtagtct  gctgcaagag  acaacggggg  gcgcgatcag  gttacgcccc      5340
ctccccggcc cgcccttttcc  tcgcccgccc  gcccgcctat  tcctccctcc  cccccccctc      5400
ctcctcctcc cccagggtcc  tcgccgcccc  cccgcctcac  cgtcgtccag  gtcgtcgtca      5460
tcctcgtccg tggtgggctc  agggtgggtg  ggcgacaggg  ccctcaccgt  gtgccccccc      5520
agggtcaggt accgcggggc  gaaccgctga  ttgcccgtcc  agataaagtc  cacggccgtg      5580
cccgccctga cggcctcctc  ggcctccatg  cgggtctggg  ggtcgttcac  gatcgggatg      5640
gtgctgaacg accccgctggg  cgtcacgccc  actatcaggt  acaccagctt  ggcgttgcac      5700
agcgggcagg tgttgcgcaa  ttgcatccag  gtttttcatgc  acgggatgca  gaagcggtgc      5760
atgcacggga aggtgtcgca  gcgcaggtgg  ggcgcgatct  catccgtgca  cacggcgcac      5820
acgtcgccct cgtcgctccc  cccgtcctct  cgagggggg   cgccccgca   actgccgggg      5880 tcttcctcgc ggggggggct  cccccccgag  accgccccc   catccacgcc   ctgcggcccc      5940
agcagccccg tctcgaacag  ttccgtgtcc  gtgctgtccg  cctcggaggc  ggagtcgtcg      6000
tcatggtggt cggcgtcccc  ccgccccccc  acttcggtct  ccgcctccga  gtcgctgctg      6060
tccggcaggt ctcggtcgca  gggaaacacc  cagacatccg  gggcgggctg  aggggaaaaa      6120
agggggggcg ggtaagaatg  gggggatttc  ccgcgtcaat  cagcgcccac  gagttccccc      6180
tccccccccg cctcacaaag  tcctgccccc  ctgctggcct  cggaagaggg  gggagaaagg      6240
ggtctgcaac caaaggtggt  ctgggtccgt  cctttggatc  ccgacccctc  ttcttccctc      6300
ttctcccgcc ctccagacgc  accggagtcg  ggggtcccac  ggcgtccccc  aaatatggcg      6360
ggcggctcct ccccacccccc  ctagatgcgt  gtgagtaagg  gggccctgcg  tatgagtcag      6420
tggggaccac gcccccctaac  acggcgaccc  cggtccctgt  gtgtttgttg  tggggggcgtg      6480 tctctgtgta tgagtcaggg  gggtcccacg  gcgacccccgg  gccctgcgtc  tgagtcaaag      6540
gggccatgtg taggtgttgg  gggtctgtat  atataaagtc  aggggggtcac  atggcgaccc      6600 ctaacagggc gaccccggtc  cctgtatata  tagggtcagg  gggttccgcg  cccccctaaca      6660 tggcgccccc ggtccctgta  tatatagtgt  cacggggttc  cacgcccccct  aacatggcgc      6720 cccaacatgg cgcccggctc  ccgtgtatga  gtgggggtcc  cccaacatgg  cggccggttc      6780
cagtgtaagg gtcggggggtc  ccccaacatg  gcgcccccca  acatggcgcc  ccccaacatg      6840
gcgccccaga catggcgccc  ggcccctcac  ctcgcgctgg  gggcggccct  caggccggcg      6900
ggtactcgct ccggggcggg  gctccatggg  ggtcgtatgc  ggctggaggg  tcgctgacgg      6960
agggtccctg ggggtcgcaa  cgtaggcggg  gcttctgtgg  tgatgcggag  aggggggcggc      7020 ccgagtctgc ctggctgctg  cgtctcgctc  cgagtgccga  ggtgcaaatg  cgaccagacc      7080
gtcgggccag ggctaactta  taccccacgc  ctttcccctc  cccaaagggg  cggcagtgac      7140 gattcccccca atggccgcgc  gtcccagggg  aggcaggccc  accgcggggc  ggccccgtcc      7200
ccggggacca accggcgcc   cccaaagaat  atcattagca  tgcacggccc  ggcccccgat      7260
ttgggggacc aacccggtgt  cccccaaaga  acccccattag  catgcccctc  ccgccgacgc      7320
aacaggggct tggcctgcgt  cggtgccccg  gggcttcccg  ccttcccgaa  gaaactcatt      7380
accatacccg gaaccccagg  ggaccaatgc  gggttcattg  agcgaccccgc  gggccaatgc      7440 gcgaggggcc gtgtgttccg  ccaaaaaagc  aattaacata  acccgaacc   ccaggggagt      7500 ggttacgcgc ggcgcgggag  gcggggaata  ccggggttgc  ccattaaggg  ccgcgggaat      7560
```

```
tgccggaagc gggaagggcg gccggggccg cccattaatg agtttctaat taccataccg    7620
ggaagcggaa caaggcctct gcaagttttt aattaccata ccgggaagtg ggcggcccgg    7680
cccactgggc gggagttacc gcccagtggg ccgggccccg acgactcggc ggacgctggt    7740
tggccgggcc ccgccgcgct ggcggccgcc gattggccag tcccgccctc cgagggcggg    7800
cccgcctcgg gggcgggccg gctccaagcg tatatatgcg cggctcctgc catcgtctct    7860
ccggagagcg gcttggtgcg gagctcccgg gagctccgcg gaagacccag gccgcctcgg    7920
gtgtaacgtt agaccgagtt cgccgggccg gctccgcggg ccagggcccg ggcacgggcc    7980
tcgggcccca ggcacggccc gatgaccgcc tcggcctccg ccacccggcg ccggaaccga    8040
gcccggtcgg cccgctcgcg ggcccacgag ccgcggcgcg ccaggcgggc ggccgaggcc    8100
cagaccacca ggtggcgcac ccggacgtgg ggcgagaagc gcaccgcgt ggggtcgcg      8160 ggggtcgcgg gggtcgcggg gggcttcggc gcccctccc cgcccgcgcg tcgcaggcgc      8220
aggcgcgcca ggtgctctgc ggtgacgcgc aggcggaggg cgaggcgcgg cggaaggcgg    8280
aaggggcgtg aggggggtg ggaggggtta gccccgcccc ccgggcccgc gccgggcggt      8340
ggggaccggg ggcggggggc ggcggcggtg ggccgggcct ctggcgccgg ctcgggcggg    8400
gggctgtccg gccagtcgtc gtcgtcgtcg tcggacgcgg actcgggaac gtggagccac    8460
tggcgcagca gcagcgaaca agaaggcggg ggcccactgg cggggggcgg cggcggggcg    8520
gccgcgggcg cgctcctgac cacgggttcc gagttgggcg tggaggttac ctgggactgt    8580
gcggttggga ccgcgcccgt gggcccgggc ggccggggc ggcgggggcc gcgatggcgg      8640
cggcgggcca tggagacaga gagcgtgccg gggtggtaga gtttgacagg caagcatgtg    8700
cgtgcagagg cgagtagtgc ttgcctgtct aactcgctag tctcggccgc ggggggcccg    8760
ggctgcccgc cgcccgcctt taaagggccg cgcgcgaccc ccggggggtg tgtttggggg    8820
ggggcccgtt ccgggggtct ggccgctcct ccccgctcc tccccccgct cctcccccg      8880 ctcctccccc cgctcctccc cccgctcctc ccccgctcc tcccccgct cctccccccg      8940 ctcctccccc cgctcctccc cccgctcctc ccccgctcc tcccccgct cctccccccg      9000 ctcctccccc cgctcctccc cccgctcctc ccccgctcc tcccccgctc ctccccgct      9060 cccgcggccc cgccccccac gcccgccgcg cgcgcgcacg ccgcccggac cgccgcccgc    9120
cttttttgcg cgcgcgcgcg cccgcggggg gcccgggctg ccacaggtaa aacaacacca    9180
acaaagcacg gcgcaatccg cacgtcacac gtcacgtcat ccaccacacc tgcccaacaa    9240
cacaactcac agcgacaact caccgcgcaa caactcctgt tcctcatcca cacgtcaccg    9300
cgcacctccc gctcctccag acgtaccccg gcgcaacaca ccgctcctgc tacacaccac    9360
cgcccctccc cagcccagc cctccccagc cccagccctc cccggcccca gccctccccg      9420
gccccagccc tccccggccc cagccctccc cggccccagc cctccccggc ccagccctc      9480 cccagcccca gccctcccca gccgcgtccc gcgctccctc gggggggttc gggcatctct    9540
acctcagtgc cgccaatctc aggtcagaga tccaaaccct ccggggcgc ccgcgcacca      9600 ccaccgcccc tcgcccctc ccgccctcg ccccctccg ccctcgccc cctcccgcc        9660 ctcgcccct ccccgcccctc gccctccc gcccctcgcc cctcccgcc cctcgcccc        9720 tcccgcccct cgcccctcc gcccctcgc ccctcccgc cctcgcccc ctccgccc        9780 tcgcccctc ccgcccctcg ccccctcccg ccctcgccc cctcccgccc ctcgcccct      9840 cccgcccctc gccccctccc gcccctcgcc ccctcccgcc cctcgccccc tcccgcccct    9900
```

-continued

```
cgccccctcc cgccctcgc ccctcccgc ccctcgaata aacaacgcta ctgcaaaact      9960
taatcaggtc gttgccgttt attgcgtctt cgggtttcac aagcgccccg ccccgtcccg    10020
gcccgttaca gcacccgtc cccctcgaac gcgccgccgt cgtcttcgtc ccaggcgcct     10080
tcccagtcca caacgtcccg tcgcgggggc gtggccaagc ccgcctccgc ccccagcacc    10140
tccacggccc ccgccgccgc cagcacggtg ccgctgcggc ccgtggccga ggcccagcga    10200
atcccgggcg gcgccggcgg cagggccccc gggccgtcgt cgtcgtcgcc gcgcagcacc    10260 agcgggggggg cgtcgtcgtc gggctccagc agggcgcggg cgcaaaagtc cctccgcggc   10320
ccgcgccacc gggccgggcc ggcgcgcacc gcctcgcgcc ccagcgccac gtacacgggc    10380
cgcagcggcg cgcccaggcc ccagcgcgcg caggcgcggt gcgagtgggc ctcctcctcg    10440
cagaagtccg gcgcgccggg cgccatggcg tcggtggtcc ccgaggccgc cgcccggccg    10500
tccagcgccg gcagcacggc ccggcggtac tcgcgcgggg acatgggcac cggcgtgtcc    10560
gggccgaagc gcgtgcgcac gcggtagcgc acgttgccgc cgcggcacag gcgcagcggc    10620
ggcgcgtcgg ggtacaggcg cgcgtgcgcg gcctccacgc gcgcgaagac ccccgggccg    10680
aacacgcggc ccgaggccag caccgtgcgg cgcaggtccc gcgccgccgg ccagcgcacg    10740
gcgcactgca cggcgggcag caggtcgcac gccaggtagg cgtgctgccg cgacaccgcg    10800
ggcccgtcgg cgggccagtc gcaggcgcgc acggtgttga ccacgatgag ccgccggtcg    10860
ccggcgctgg cgagcagccc cagaaactcc acggcccccgg cgaaggccag gtcccgcgtg   10920
gacagcagca gcacgccctg cgcgcccagc gccgacacgt cgggggcgcc ggtccagttg    10980
cccgcccagg cggccgtgtc cggccccgcac agccggttgg ccaggccgc cagcaggcag    11040 gacagcccgc cgcgctcggc ggaccactcc ggcggccccc ccgaggcccc gccgccggcc    11100
aggtcctcgc ccggcagcgg cgagtacagc accaccacgc gcacgtcctc ggggtcgggg    11160
atctggcgca tccaggccgc catgcggcgc agcgggcccg aggcgcgcag ggggccaaag    11220
aggcggcccc cggcggcccc gtgggggtgg gggttctcgt cgtcgtcgcc gccgcacgcg    11280
gcctgggcgg cggggggcggg cccggcgcac cgcgcggcga tcgaggccag ggcccgcggg    11340
tcaaacatga gggccggtcg ccaggggacg gggaacagcg ggtggtccgt gagctcggcc    11400
acggcgcgcg gggagcagta ggcctccagg gcggcggccg cgggcgccgc cgtgtggctg    11460
ggcccccggg gctgccgccg ccagccgccc aggggggtcgg ggccctcggc gggcggcgc    11520 gacagcgcca cggggcgcgg gcgggcctgc gccgcggcgc cccgggccgc cgcgggctgg    11580
gcgggggtgg gctcgggccc cggggggcgtg gaggggggcg cggggagggg ggcgcgggcg   11640
tccgagccgg gggcgtccgc gccgctcttc ttcgtcttcg ggggtcgcgg gccgccgcct    11700
ccggcggccc gggccgggcc gggactcttg cgcttgcgcc cctccgcggg cgcggcggag    11760
gcggcggcgg ccgccagcgc gtcggcggcg tccggtgcgc tggccgccgc cgccagcagg    11820
gggcggaggc tctggttctc aaacagcagg tccgcggcgg cggcggccgc ggagctcggc    11880
aggcgcgggt cccgcggcag cgcgggggccc agggccccgg cgaccaggct cacgcgcgcg    11940
acggcggcca cggcggcctc gctgccgccg gccacgcgca ggtccccgcg caggcgcatg    12000
agcaccagcg cgtcgcgcac gaaccgcagc tcgcgcagcc acgcgcgcag gcgggggcgcg   12060 tcggcgtgcg gcggcggcgg ggaagcgggg cccgcgggtc cctccggccg cggggggctg    12120
gcgggcgggg ccccggccag ccccgggacg gccgccaggt cgccgtcgaa gccctcggcc    12180
agcgcctcca ggatcccgcg gcaggcggcc aggcactcga cggccacgcg gccggcctgg    12240
gcgcggcgcc cggcgtcggc gtcggcgtgg cgggcgggcgt cggggtcgtc gccccccacg    12300
```

```
ggggaggcgg gcgcggcgga cagccgcccc agggcggcga ggatccccgc ggcgccgtac   12360
ccggcgggca ccgcgcgctc gcccggtgcg gcggcggcga cggcggcgac cccctcgtca   12420
tctgcgccgg cgccggggct ccccgcggcc cccgtcagcg ccgcgttctc gcgcgccaac   12480
aggggcgcgt aggcgcggcg caggctggtc agcaggaagc ccttctgcgc gcggtcgtat   12540
cggcggctca tggccacggc ggccgccgcg tgcgccaggc cccagccgaa gcggccggcc   12600
gccatggcgt agcccaggtg gggcacggcc cgcgccacgc tgccggtgat gaaggagctg   12660
ctgttgcgcg cggcgcccga gatccggaag caggcctggt ccagcgccac gtccccgggg   12720
accacgcgcg ggttctggag ccaccccatg gcctccgcgt ccggggtgta cagcagccgc   12780
gtgatcaggg cgtactgctg cgcggcgtcg cccagctcgg gcgcccacac ggccgccggg   12840
gcgcccgagg cctcgaaccg gcgtcgcgcc tcctccgcct cgggcgcccc ccagaggccc   12900
gggcggctgt cgcccaggcc gccgtacagc acccgccccg ggggcggggg cccggcgccg   12960
ggccacggct ccccgctgac gtacccgtcg cgatagcgcg cgtagaaggc gccggaggcc   13020
gcgtcggcgt ccagctcgac ccgccggggc tgcccggccg tgaagcggcc cgtggcgtcg   13080
cggcggccca ccgccgcgcg ggcccggcgg cgctcgatgc ggcccgcgga ggccgcgggg   13140
gtcctcgccg ccgcccgggg cttgggcgcg gcctcggaga ggggggggtgg cccgggcggg   13200 ggcggcgtcc gcccgggggc ttccggcgcc gcgctcgacg gaccccgccc gacggcccgc   13260
gcctcgcgtg cgtggtcggc cgcgtcgttg ccgtcgtcgt cctcgtcctc gtcggacgac   13320
gaggacgaag aggatgcgga cgacgaggac gaggacccgg agtccgacga ggtcgatgac   13380
gccgatggcc gccgccggcc gtgacgacgt ctccgcggcg gctgggccgg cgggcgcggc   13440
gacaggcggt ccgtggggtc cggatacgcg ccgcgtagcg gggcctcccg ttcgcggccc   13500
cgggccgggg cccggtcgcc ggcggcgtcg gctgcgtcgt cgtactcgtc cccgtcatcg   13560
tcgtcggcta gaaaggcggg ggtccggggc ggcgaggccg cggggtcggg cgtcgggatc   13620
gtccggacgg cctcctctac catggaggcc agcagagcca gctgtcgcga cgagacggcg   13680 tccccgcgcgt cctcgccggc gtcggtgccc gccgcggggg ccctcccgtc ccgccgggcg   13740
tcgtcgaggt cgtgggggtg gtcggggtcg tggtcgtggg cgtccccgcc ctcctccgtc   13800
tccgcgcccc acccgagggc cccccgctcg tcgcggtctg ggctcggggt gggcggcggc   13860
ccgtcggtgg ggcccgggga gccggggcgc tgcttgttct ccgacgccat cgccgatgcg   13920
gggcgatcct ccggggatac ggctgcgacg gcggacgtag cacggtaggt cacctacgga   13980
ctctcgatgg ggggaggggg cgagacccac ggaccccgac gaccccgcc gtcgacgcgg   14040 aactagcgcg gaccggtcga tgcttgggtg gggaaaaagg acagggacgg ccgatccccc   14100
tcccgcgctt cgtccgcgta tcggcgtccc ggcgcggcga cgtctgacg gtctgtctct   14160 ggcggtcccg cgtcgggtcg tg                                            14182
```

```
<210> SEQ ID NO 3
<211> LENGTH: 647
<212> TYPE: DNA
<213> ORGANISM: Artificial Sequence
<220> FEATURE:
<223> OTHER INFORMATION: deleted UL56

<400> SEQUENCE: 3
gcatggcgcc acaccacgcc acaacagccc tgtcgccggt atggggcatg atcagacgag     60
ccgcgcgccg cgcgttgggc cctgtacagc tcgcgcgaat tgaccctagg aggccgccac    120
```

-continued

```
gcgcccgagt tttgcgttcg tcgctggtcg tcgggcgcca aagccccgga cggctgttcg        180
gtcgaacgaa cggccacgac agtggcatag gttgggggt ggtccgacat agcctcggcg        240
tacgtcggga ggcccgacaa gaggtccctt gtgatgtcgg gtggggccac aagcctggtt        300
tccggaagaa acaggggggt tgccaataac ccgccagggc caaaactccg cgctgcgca         360 cgtcgttcgg cgcggcgccg ggcgcgccga gcggctcgct gggcggcttg gcgtgagcgg        420
ccccgctccg acgcctcgcc ctctccggag gaggttggcg gaattggcac ggacgacagg        480
ggcccagcag agtacggtgg aggtgggtcc gtgggggtgt ccagatcaat aacgacaaac        540
ggcccctcgt tcctaccaga caagctatcg tagggggcg ggggatcagc aaacgcgttc         600
cccgcgctcc atagacccgc gtcgggttgc gccgcctccg aagccat                      647
```

<210> SEQ ID NO 4
<211> LENGTH: 134271
<212> TYPE: DNA
<213> ORGANISM: Artificial Sequence
<220> FEATURE:
<223> OTHER INFORMATION: dIR-dICP6 recombinant HSV-1

<400> SEQUENCE: 4

```
gcagcccggg cccccgcgg gcgcgcgcgc gcgcaaaaaa ggcgggcggc ggtccgggcg          60
gcgtgcgcgc gcgcggcggg cgtggggggc ggggccgcgg gagcggggga ggagcggggg        120
aggagcgggg ggaggagcgg gggggaggagc ggggggagga gcggggggag gagcggggggg      180 aggagcgggg ggaggagcgg gggggaggagc ggggggagga gcggggggag gagcggggggg      240 aggagcgggg ggaggagcgg gggggaggagc ggggggagga gcggggggag gagcggggggg      300 aggagcgggg gaggagcggc cagaccccgg aaacgggccc ccccaaaac acacccccg          360 ggggtcgcgc gcggcccttt aaaggcgggc ggcgggcagc ccgggccccc cgcggccgag        420
actagcgagt tagacaggca agcactactc gcctctgcac gcacatgctt gcctgtcaaa        480
ctctaccacc ccggcacgct ctctgtctcc atggcccgcc gccgccatcg cggccccgc         540 cgcccccggc cgcccgggcc cacgggcgcg gtcccaaccg cacagtccca ggtaacctcc        600
acgcccaact cggaacccgt ggtcaggagc gcgcccgcgg ccgcccgccc gccgccccc         660 gccagtgggc ccccgccttc ttgttcgctg ctgctgcgcc agtggctcca cgttcccgag        720
tccgcgtccg acgacgacga cgacgactgg ccggacagcc ccccgcccga gccggcgcca        780
gaggcccggc ccaccgccgc cgcccccgc ccccggtccc caccgcccgg cgcgggcccg         840 ggggcgggg ctaacccctc ccaccccccc tcacgcccct tccgccttcc gccgcgcctc         900
gccctccgcc tgcgcgtcac cgcagagcac ctggcgcgcc tgcgcctgcg acgcgcgggc        960
ggggaggggg cgccgaagcc ccccgcgacc cccgcgaccc ccgcgacccc cacgcgggtg       1020
cgcttctcgc cccacgtccg ggtgcgccac ctggtggtct gggcctcggc cgcccgcctg      1080
gcgcgccgcg gctcgtgggc ccgcgagcgg gccgaccggg ctcggttccg cgcgccgggtg     1140 gcggaggccg aggcggtcat cgggccgtgc ctggggcccg aggcccgtgc ccgggccctg      1200
gcccgcggag ccggccggc gaactcggtc taacgttaca cccgaggcgg cctgggtctt       1260
ccgcggagct cccgggagct ccgcaccaag ccgctctccg agagacgat ggcaggagcc        1320 gcgcatatat acgcttggag ccggcccgcc cccgaggcgg gcccgccctc ggagggcggg      1380
actggccaat cggcggccgc cagcgcggcg gggcccggcc aaccagcgtc gccgagtcg        1440 tcgggggcccg gcccactggg cggtaactcc cgccagtgg gccgggccgc ccacttcccg       1500
gtatggtaat taaaaacttg cagaggcctt gttccgcttc ccggtatggt aattagaaac      1560
```

```
tcattaatgg gcggccccgg ccgcccttcc cgcttccggc aattcccgcg gcccttaatg   1620
ggcaaccccg gtattccccg cctcccgcgc cgcgcgtaac cactcccctg gggttccggg   1680
ttatgttaat tgcttttttg gcggaacaca cggcccctcg cgcattggcc cgcgggtcgc   1740
tcaatgaacc cgcattggtc ccctgggggtt ccgggtatgg taatgagttt cttcgggaag   1800
gcgggaagcc ccggggcacc gacgcaggcc aagcccctgt tgcgtcggcg ggaggggcat   1860
gctaatgggg ttctttgggg gacaccgggt tggtccccca aatcgggggc cgggccgtgc   1920
atgctaatga tattctttgg gggcgccggg ttggtccccg gggacggggc cgccccgcgg   1980
tgggcctgcc tcccctggga cgcgcggcca ttggggggaat cgtcactgcc gcccctttgg   2040
ggaggggaaa ggcgtggggt ataagttagc cctggcccga cggtctggtc gcatttgcac   2100
ctcggcactc ggagcgagac gcagcagcca ggcagactcg ggccgccccc tctccgcatc   2160
accacagaag ccccgcctac gttgcgaccc ccagggaccc tccgtcagcg accctccagc   2220
cgcatacgac ccccatggag ccccgccccg gagcgagtac ccgccggcct gagggccgcc   2280
cccagcgcga ggtgaggggc cgggcgccat gtctggggcg ccatgttggg gggcgccatg   2340
ttggggggcg ccatgttggg ggaccccccga cccttacact ggaaccggcc gccatgttgg   2400
gggaccccca ctcatacacg ggagccgggc gccatgttgg ggcgccatgt taggggggcgt   2460 ggaaccccgt gacactatat atacaggggac cgggggcgcc atgttagggg gcgcggaacc   2520
ccctgaccct atatatacag ggaccggggt cgccctgtta ggggtcgcca tgtgaccccc   2580
tgactttata tatacagacc cccaacacct acacatggcc cctttgactc agacgcaggg   2640
cccggggtcg ccgtgggacc cccctgactc atacacagag acacgccccc acaacaaaca   2700
cacagggacc ggggtcgccg tgttaggggg cgtggtcccc actgactcat acgcagggcc   2760
cccttactca cacgcatcta ggggggtggg gaggagccgc ccgccatatt tgggggacgc   2820
cgtgggaccc ccgactccgg tgcgtctgga gggcgggaga agagggaaga agaggggtcg   2880
ggatccaaag gacggaccca gaccaccttt ggttgcagac cccttttctcc ccctcttcc   2940 gaggccagca gggggggcagg actttgtgag gcggggggggg aggggggaact cgtgggcgct   3000 gattgacgcg ggaaatcccc ccattcttac ccgcccccccc ttttttcccc tcagcccgcc   3060
ccggatgtct gggtgtttcc ctgcgaccga gacctgccgg acagcagcga ctcggaggcg   3120
gagaccgaag tgggggggggcg gggggacgcc gaccaccatg acgacgactc cgcctccgag   3180
gcggacagca cggacacgga actgttcgag acggggctgc tggggccgca gggcgtggat   3240 gggggggggcg tctcgggggg gagcccccccc cgcgaggaag accccggcag ttgcgggggggc   3300 gccccccctc gagaggacgg ggggagcgac gagggcgacg tgtgcgccgt gtgcacggat   3360
gagatcgcgc cccacctgcg ctgcgacacc ttcccgtgca tgcaccgctt ctgcatcccg   3420
tgcatgaaaa cctggatgca attgcgcaac acctgcccgc tgtgcaacgc caagctggtg   3480
tacctgatag tgggcgtgac gcccagcggg tcgttcagca ccatcccgat cgtgaacgac   3540
ccccagaccc gcatggaggc cgaggaggcc gtcagggcgg gcacggccgt ggactttatc   3600
tggacgggca atcagcggtt cgccccgcgg tacctgaccc tgggggggggca cacggtgagg   3660 gccctgtcgc ccacccaccc tgagcccacc acggacgagg atgacgacga cctgacgac   3720 ggtgaggcgg gggggcggcg aggaccctgg gggaggagga ggaggggggg gggaggggagg   3780 aataggcggg cgggcgggcg aggaaagggc gggccgggga gggggcgtaa cctgatcgcg   3840 cccccccgttg tctcttgcag cagactacgt accgcccgcc ccccgccgga cgccccgcgc   3900
```

-continued

```
cccccacgc agaggcgccg ccgcgccccc cgtgacgggc ggggcgtctc acgcagcccc    3960
ccagccggcc gcggctcgga cagcgccccc ctcggcgccc atcgggccac acggcagcag    4020
taacactaac accaccacca acagcagcgg cggcggcggc tcccgccagt cgcgagccgc    4080
ggtgccgcgg ggggcgtctg gcccctccgg gggggttggg gttgttgaag cggaggcggg    4140
gcggccgagg ggccggacgg gcccccttgt caacagaccc gccccccttg caaacaacag    4200 agacccata gtgatcagcg actccccccc ggcctctccc cacaggcccc ccgcggcgcc    4260
catgccaggc tccgcccccc gccccggtcc ccccgcgtcc gcggccgcgt cgggccccgc    4320 gcgccccgc gcggccgtgg ccccgtgtgt gcgggcgccg cctccggggc ccggcccccg    4380
cgccccggcc cccggggcgg agccggccgc ccgccccgcg gacgcgcgcc gtgtgcccca    4440
gtcgcactcg tccctggctc aggccgcgaa ccaagaacag agtctgtgcc gggcgcgtgc    4500
gacggtggcg cgcggctcgg ggggggccggg cgtggagggt ggacacgggc cctcccgcgg    4560
cgccgccccc tccggcgccg ccccctccgg cgcccccccg ctccctccg ccgcctctgt     4620 cgagcaggag gcggcggtgc gtccgaggaa gaggcgcggg tcgggccagg aaaacccctc    4680
cccccagtcc acgcgtcccc ccctcgcgcc ggcaggggcc aagagggcgg cgacgcaccc    4740
cccctccgac tcagggccgg ggggggcgcgg ccagggaggg cccgggaccc ccctgacgtc    4800
ctcggcggcc tccgcctctt cctcctccgc ctcttcctcc tcggccccga ctcccgcggg    4860
ggccacctct tccgccaccg gggccgcgtc ctcctccgct tccgcctcct cgggcgggc    4920 cgtcggtgcc ctgggaggga gacaagagga aacctccctc ggcccccgcg ctgcttctgg    4980
gccgcggggg ccgaggaagt gtgcccggaa gacgcgccac gcggagactt ccggggccgt    5040
ccccgcgggc ggcctcacgc gctacctgcc catctcgggg gtctctagcg tggtcgccct    5100
gtcgccttac gtgaacaaga cgatcacggg ggactgcctg cccatcctgg acatggagac    5160
ggggaacatc ggggcgtacg tggtcctggt ggaccagacg ggaaacatgg cgacccggct    5220
gcgggccgcg gtccccggct ggagccgccg caccctgctc cccgagaccg cgggtaacca    5280
cgtgacgccc cccgagtacc cgacggcccc cgcgtcggag tggaacagcc tctggatgac    5340
ccccgtgggg aacatgctgt tcgaccaggg caccctagtg ggcgccctgg acttccgcag    5400
cctgcggtct cggcacccgt ggtccgggga gcaggggcg tcgacccggg acgagggaaa    5460
acaataaggg acgcccccgt gtttgtgggg aggggggggt cgggcgctgg gtggtctctg    5520
gccgcgccca ctacaccagc caatccgtgt cggggaggtg gaaagtgaaa gacacgggca    5580
ccacacacca gcgggtcttt tgtgttggcc ctaataaaaa aaactcaggg gatttttgct    5640
gtctgttggg aaataaaggt ttactttgt atctttccc tgtctgtgtt ggatgtatcg     5700 cggggtgcg tgggagtggg ggtgcgtggg agtgggggtg cgtgggagtg ggggtgcgtg    5760
ggagtggggg tgcgtgggag tgggggtgcg tgggagtggg ggtgcgtggg agtggggtg    5820 cgtgggagtg ggggtgcgtg ggagtggggg tgccatgttg gcaggctct ggtgttaacc     5880 acagagccgc ggcccgggct gcctgaccac cgatccccga aagcatcctg ccactggcat    5940
ggagccagaa ccacagtggg ttgggtgtgg gtgttaagtt tccgcgagcg cctgcccgcc    6000
cggactgacc tggcctctgg ccgccacaaa gggcgggggg ggggttaac tacactatag     6060 ggcaacaaag gatgggaggg gtagcggggc gggacggggc gcccaaaagg gggtcggcca    6120
caccacagac gtgggtgttg ggggtgtggg cggagggtg gggggggaga cagaaacagg     6180
aacatagtta gaaaacaaga atgcggtgca gccagagaat cacaggagac gagggatgg     6240 gcgtgttggt taccaaccca cacccaggca tgctcggtgg tatgaaggag ggggggcggt    6300
```

-continued

```
gtttcttaga gaccgccggg ggacgtgggg ttggtgtgca aaggcacgcg caccogcgcc    6360 ggccaggtgg gccggtaccc catccccccc tcccccgacc cttcccaccc ccgcgtgcca    6420
gagatcaccc cggtcccccg gcacccgcca ctcctccata tcctcgcttt aggaacaact    6480
ttaggggggg gtacacacgc gccgtgcatt tccttccaca cccccccccct cccccgcact    6540 ccccccccc aggcagtaag acccaagcat agagagccag gcacaaaaac acaggcgggg    6600
tgggacacat gccttcttgg agtacgtggg tcattggcgt gggggggttac agcgacaccg    6660 gccgacccc tggcggtctt ccagccggcc cttagataag ggggcagttg gtggtcggac    6720
gggtaagtaa cagagtctaa ctaagggtgg gaggggggga aaataacggg ctggtgtgct    6780
gtaacacgag cccacccgcg agtggcgtgg ccgaccttag cctctggggc gcccctgtc    6840 gtttgggtcc ccccccctct attggggaga agcaggtgtc taacctacct ggaaacgcgg    6900
cgtctttgtt gaacgacacc ggggcgccct cgacgagtgg gataacgggg gaggaaggga    6960
gggaggaggg tactggggt gaagggggg ggggagaagc gagaacagga aaggcgacgg    7020
agcccggcag aacaccgagg aaaaaaaaac cacagcgcat gcgccgggcc gttgtggggc    7080
cccgggccgg ggcccttgg gtccgccggg gccccgggcc gggccgccac gggggccggc    7140
cgttggcggt aaccccgagt gttcatctca ggccccgggc cgggaacccg gaaaagcctc    7200
cggggggcct ttttcgcgtc gcgtgccggc gagcgggtcc ggacggggcc cggaccgccg    7260
cggtcggggg cccctcgtcc cgggccgtac gcggccttcg ccccgtgagg ggacagacga    7320
acgaaacatt ccggcgacgg aacgaaaaac accccagacg ggttaaagaa acagaaaccg    7380 caaccccac caccccgaa acggggaaaa cgaaaaaaca gaccagcggc cggccggcgc    7440 ttaggggag gatgtcgccg acgcccttg gccgccccgg ctgcaggggg gcccggagag    7500
ccgcggcacc cggacgcgcc cggaaagtct ttcgcaccac cggcgatcgg cacggccgcg    7560
cccccgcttt tataaaggct cagatgacgc agcaaaaaca ggccacagca ccacatgggt    7620
aggtgatgta atttttatttt cctcgtctgc ggcctaatgg atttccgggc gcggtgcccc    7680
tgtctgcaga gcacttaacg gattgatatc tcgcgggcac gcgcgccctt aatggaccgg    7740
cgcggggcgg ggggccggat acccacacgg gcggggggggg gtgtcgcggg ccgtctgctg    7800
gcccgcggcc acataaacaa tgactcgggg cctttctgcc tctgccgctt gtgtgtgcgc    7860
gcgccggctc tgcggtgtcg gcggcggcgg cggcggtggc cgccgtgttc ggtctcggta    7920
gccggccggc gggtggactc gcggggggcc ggagggtgga aggcagggggg gtgtaggatg    7980 ggtatcagga cttccacttc ccgtccttcc atcccccgtt ccctcggtt gttcctcgcc    8040 tcccccaaca ccccgccgct ttccgttggg gttgttattg ttgtcgggat cgtgcgggcc    8100
gggggtcgcc ggggcagggg cggggcgtg ggcgggggtg ctcgtcgatc gaccgggctc    8160 agtggggggcg tggggtgggt gggagaaggc gaggagactg gggtgggggt gtcggtgggt    8220
ggttgttttt tgtggttgtt ttttgtgtct gtttccgtcc cccgtcaccc ccctccctcc    8280
gtcccctccg tcccccgtc gcgggtgttt gtgtttgttt attccgacat cggtttattt    8340
aaaataaaca cagccgttct gcgtgtctgt tcttgcgtgt ggctgggggc ttatatgtgg    8400
ggtcccgggg gcgggatggg gtttagcggc ggggggcggc gcgccggacg gggcgctgga    8460
gataacggcc cccgggggaac gggggaccgg ggctgggtat cccgaggtgg gtgggtgggc    8520
ggcggtggcc gggccgggcc gggccgggcc gggtgggcgg ggtttggaaa aacgaggagg    8580
aggaggagaa ggcggggggg gagacggggg gaaagcaagg acacggcccg ggggggtggga    8640
```

-continued

```
gcgcgggccg ggccgctcgt aagagccgcg acccggccgc cggggagcgt tgtcgccgtc    8700
ggtctgccgg cccccgtccc tccctttttt gaccaaccag cgccctcccc cccaccacca    8760
ttcctactac caccaccacc accaccccca ccaccgacac ctcccgcgca ccccgccca     8820 catccccca ccccgcacca cgagcacggg gtggggtag cagggatca aaggggggca     8880 aagccggcgg ggcggttcgg ggggcggga gaccgagtag gcccgccat acgcggcccc     8940 tcccggcagc cacgcccccc agcgtcgggt gtcacggga aagagcaggg gagaggggg     9000 gagaggggag agggggggag aggggagagg gggggagagg ggagaggggg ggagagggga    9060 gagggggga gaggggagag gggggagag gggagagggg gggagaggg agaggggggg     9120 agaggggaga ggggggaga ggggagaggg ggggagaggg ggtatataaa ccaacgaaaa    9180
gcgcgggaac ggggatacgg ggcttgtgtg gcacgacgtc gtggttgtgt tactgggcaa    9240
acacttgggg actgtaggtt tctgtgggtg ccgaccctag cgctatggg gattttgggt    9300 tgggtcgggc ttattgccgt tggggttttg tgtgtgcggg ggggcttgtc ttcaaccgaa    9360
tatgttattc ggagtcgggt ggctcgagag gtgggggata tattaaaggt gccttgtgtg    9420
ccgctcccgt ctgacgatct tgattggcgt tacgagaccc cctcggctat aaactatgct    9480
ttgatagacg gtatatttt gcgttatcac tgtcccggat tggacacggt cttgtgggat    9540
aggcatgccc agaaggcata ttgggttaac cccttttat ttgtggcggg ttttctggag    9600
gacttgagtc acccgcgtt tcctgccaac acccaggaaa cagaaacgcg cttggccctt    9660
tataaagaga tacgccaggc gctggacagt cgcaagcagg ccgccagcca cacacctgtg    9720
aaggctgggt gtgtgaactt tgactattcg cgcacccgcc gctgtgtagg gcgacaggat    9780
ttgggaccta ccaacggaac gtctggacgg accccggttc tgccgccgga cgatgaagcg    9840
ggcctgcaac cgaagcccct caccacgccg ccgcccatca tcgccacgtc ggacccccacc   9900 ccgcgacggg acgccgccac aaaaagcaga cgccgacgac cccactcccg gcgcctctaa    9960
cgatgcctcg acggaaaccc gtcccgggttc ggggggcgaa ccggccgcct gtcgctcgtc    10020
agggccggcg ggcgctcctc gccgccctag aggctgtccc gctggtgtga cgttttcctc    10080
gtccgcgccc cccgaccctc ccatggattt aacaaacggg ggggtgtcgc ctgcggcgac    10140
ctcggcgcct ctggactgga ccacgtttcg gcgtgtgttt ctgatcgacg acgcgtggcg    10200
gcccctgatg gagcctgagc tggcgaaccc cttaaccgcc cacctcctgg ccgaatataa    10260
tcgtcggtgc cagaccgaag aggtgctgcc gccgcgggag gatgtgtttt cgtggactcg    10320
ttattgcacc cccgacgagg tgcgcgtggt tatcatcggc caggacccat atcaccaccc    10380
cggccaggcg cacggacttg cgtttagcgt gcgcgcgaac gtgccgcctc ccccgagtct    10440
tcggaatgtc ttggtggccg tcaagaactg ttatcccgag gcacggatga gcggccacgg    10500
ttgcctggaa aagtgggcgc gggacggcgt cctgttacta aacacgaccc tgaccgtcaa    10560
gcgcggggcg gcgcgtccc actctagaat cggttgggac cgcttcgtgg gcggagttat    10620
ccgccggttg gccgcgcgcc gccccggcct ggtgtttatg ctctggggcg cacacgccca    10680
gaatgccatc aggccggacc ctcgggtcca ttgcgtcctc aagttttcgc acccgtcgcc    10740
cctctccaag gttccgttcg gaacctgcca gcatttcctc gtggcgaacc gatacctcga    10800
gacccggtcg atttcaccca tcgactggtc ggtttgaaag gcatcgacgt ccggggtttt    10860
tgtcggtggg ggcttttggg tatttccgat gaataaagac ggttaatggt taaacctctg    10920
gtctcatacg ggtcggtgat gtcggggcgtc ggggagagg gagttccctc tgcgcttgcg    10980
attctagcct cgtggggctg gacgttcgac acgccaaacc acgagtcggg gatatcgcca    11040
```

```
gatacgactc ccgcagattc cattcggggg gccgctgtgg cctcacctaa ccaacctta    11100 cacgggggcc cggaacggga ggccacagcg ccgtctttct ccccaacgcg cgcggatgac    11160
ggcccgccct gtaccgacgg gccctacgtg acgtttgata ccctgtttat ggtgtcgtcg    11220
atcgacgaat tagggcgtcg ccagctcacg dacaccatcc gcaaggacct gcggttgtcg    11280
ctggccaagt ttagcattgc gtgcaccaag acctcctcgt tttcgggaaa cgccccgcgc    11340
caccacagac gcggggcgtt ccagcgcggc acgcgggcgc cgcgcagcaa caaaagcctc    11400
cagatgtttg tgttgtgcaa acgcgcccac gccgctcgag tgcgagagca gcttcgggtc    11460
gttattcagt cccgcaagcc gcgcaagtat tacacgcgat cttcggacgg gcggctctgc    11520
cccgccgtcc ccgtgttcgt ccacgagttc gtctcgtccg agccaatgcg cctccaccga    11580
gataacgtca tgctggcctc gggggccgag taaccgcccc cccccatgc caccctcact    11640 gcccgtcgcg cgtgtttgat gttaataaat aacacataaa tttggctggt tgtttgttgt    11700
ctttaatgga ccgcccgcaa ggggggggg gcgtttcagt gtcgggtgac gagcgcgatc    11760
cggccgggat cctaggaccc caaaagtttg tctgcgtatt ccagggtggg gctcagttga    11820
atctcccgca gcacctctac cagcaggtcc gcggtgggct ggagaaactc ggccgtcccg    11880
gggcaggcgg ttgtcggggg tggaggcgcg gcgcccaccc cgtgtgccgc gcctggcgtc    11940
tcctctgggg gcgacccgta aatggttgca gtgatgtaaa tggtgtccgc ggtccagacc    12000
acggtcaaaa tgccggccgt ggcgctccgg gcgctttcgc cgcgcgagga gctgacccag    12060
gagtcgaacg gatacgcgta catatgggcg tcccacccgc gttcgagctt ctggttgctg    12120
tcccggccta taaagcggta ggcacaaaat tcggcgcgac agtcgataat caccaacagc    12180
ccaatggggg tgtgctggat aacaacgcct ccgcgcggca ggcggtcctg gcgctcccgg    12240
ccccgtacca tgatcgcgcg ggtgccgtac tcaaaaacat gcaccacctg cgcggcgtcg    12300
ggcagtgcgc tggtcagcga ggccctggcg tggcataggc tatacgcgat ggtcgtctgt    12360
ggattggaca tctcgcggtg ggtagtgagt cccccgggcc gggttcggtg gaactgtaag    12420
gggacggcgg gttaatagac aatgaccacg ttcggatcgc gcagagccga tagtatgtgc    12480
tcactaatga cgtcatcgcg ctcgtggcgc tcccggagcg gatttaagtt catgcgaagg    12540
aattcggagg aggtggtgcg ggacatggcc acgtacgcgc tgttgaggcg caggttgccg    12600
ggcgtaaagc agatggcgac cttgtccagg ctaaggccct gggagcgcgt gatggtcatg    12660
gcaagcttgg agctgatgcc gtagtcggcg tttatggcca tggccagctc cgtagagtca    12720
atggactcga caaactcgct gatgttggtg ttgacgacgg acatgaagcc gtgttggtcc    12780
cgcaagacca cgtaaggcag gggggcctct tccagtaact cggccacgtt ggccgtcgcg    12840
tgccgcctcc gcagctcgtc cgcaaaggca aacacccgtg tgtacgtgta tcccatgagc    12900
gtataattgt ccgtctgcag ggcgacggac atcagccccc cgcgcggcga gccggtcagc    12960
atctcgcagc cccggaagat aacgttgtcc acgtacgtgc taaaggggggc gacttcaaat    13020 gcctccccga agagctcttg gaggattcgg aatctcccga ggaaggcccg cttcagcagc    13080
gcaaactggg tgtgaacggc ggcggtggtc tccggttccc cgggggtgta gtggcagtaa    13140
aacacgtcga gctgttgttc gtccagcccc gcgaaaataa cgtcgaggtc gtcgtcggga    13200
aaatcgtccg ggcccccgtc ccgcggcccc agttgcttaa aatcaaacgc acgctcgccg    13260
ggggcgcctg cgtcggccat taccgacgcc tgcgtcggca ccccgaaga tttggggcgc    13320 agagacagaa tctccgccgt tagttctccc atgcgggcgt acgcgagggt cctctgggtc    13380
```

```
gcatccaggc ccgggcgctg cagaaagttg taaaaggaga taagcccgct aaatatgagc   13440
cgcgacagga acctgtaggc aaactccacc gaagtctccc cctgagtctt tacaaagctg   13500
tcgtcacgca acactgcctc gaaggcccgg aacgtccac  taaacccaaa aaccagtttt   13560
cgcaggcgcg cggtcaccgc gatctggctg ttgaggacgt aagtgacgtc gttgcgggcc   13620
acgaccagct gctgtttgct gtgcacctcg cagcgcatgt gccccgcgtc ctggtcctgg   13680
ctctgcgagt agttggtgat gcggctggcg ttggccgtga gccacttttc aatagtcagg   13740
ccgggctggt gtgtcagccg tcggtattcg tcaaactcct tgaccgacac gaacgtaagc   13800
acggggaggt gaacacgac  gaactccccc tcacgggtca ccttcaggta ggcgtggagc   13860
ttggccatgt acgcgctcac ctctttgtgg gaggagaaca gccgcgtcca gccggggagg   13920
ttggcggggt tggtgatgta gttttccggg acgacgaagc gatccacgaa ctgcatgtgc   13980
tcctcggtga tgggcaggcc gtactccagc accttcatga ggttaccgaa ctcgtgctcg   14040
acgcaccgtt tgttgttaat aaaaatggcc cagctatacg agaggcgggc gtactcgcgc   14100
agcgtgcggt tgcagatgag gtacgtgagc acgttctcgc tctggcggac ggaacaccgc   14160
agtttctggt gctcgaaggt cgactccagg gacgccgtct gcgtcggcga gcccacacac   14220
accaacacgg gccgcaggcg ggccgcgtac tgggggggtgt ggtacagggc gttaatcatc   14280
caccagcaat acaccacggc cgtgaggagg tgacgcccaa ggagcccggc ctcgtcgatg   14340
acgatcacgt tgctgcgggt aaaggccggc agcgccccgt gggtggccgg ggccaaccgc   14400
gtcagggcgc cctcggccaa ccccagggtc cgttccaggg cggccagggc gcgaaactcg   14460
ttccgcaact cctcgccccc ggaggcggcc agggcgcgct tcgtgaggtc caaaatcacc   14520
tcccagtagt acgtcagatc tcgtcgctgc aggtcctcca gcgaggcggg gttgctggtc   14580
agggtgtacg ggtactgtcc cagttgggcc tggacgtgat tcccgcgaaa cccaaattca   14640
tgaaagatgg tgttgatggg tcggctgaga aaggcgcccg agagtttggc gtacatgttt   14700
tgggccgcaa tgcgcgtggc gcccgtcacc acacagtcca agacctcgtt gattgtctgc   14760
acgcacgtgc tctttccgga gccagcgttg ccggtgataa gatacaccgc gaacggaaac   14820
tccctgaggg gcaggcctgc gggggactct aaggccgcca cgtcccggaa ccactgcaga   14880
cggggcactt gcgctccgtc gagctgttgt tgcgagagct ctcggatgcg cttaaggatt   14940
ggctgcaccc cgtgcataga cgtaaaattt aaaaaggcct cggccctccc tggaacggct   15000
ggtcggtccc cgggttgctg aaggtgcggc gggccgggtt tctgtccgtc tagctggcgc   15060
tccccgccgg ccgccgccat gaccgcacca cgctcgtggg cccccactac gcgtgcgcgg   15120
ggggacacgg aagcgctgtg ctcccccgag gacggctggg taaaggttca ccccacccc  15180 ggtacgatgc tgttccgtga gattctccac gggcagctgg ggtataccga gggccagggg   15240
gtgtacaacg tcgtccggtc cagcgaggcg accacccggc agctgcaggc ggcgatcttt   15300
cacgcgctcc tcaacgccac cacttaccgg gacctcgagg cggactggct cggccacgtg   15360
gcggcccgcg gtctgcagcc ccaacggctg gttcgccggt acaggaacgc ccgggaggcg   15420
gatatcgccg gggtggccga gcgggtgttc gacacgtggc ggaacacgct taggacgacg   15480
ctgctggact ttgcccacgg gttggtcgcc tgctttgcgc cggcggcccc gagcggcccg   15540
tcaagcttcc ccaaatatat cgactggctg acgtgcctgg ggctggtccc catattacgc   15600
aagcgacaag aagggggtgt gacgcagggt ctgagggcgt ttctcaagca gcacccgctg   15660
acccgccagc tggccacggt cgcggaggcc gcggagcgcg ccggccccgg gtttttttgag   15720 ctggcgctgg ccttcgactc cacgcgcgtg gcggactacg accgcgtgta tatctactac   15780
```

-continued

```
aaccaccgcc ggggcgactg gctcgtgcga gaccccatca gcgggcagcg cggagaatgt   15840
ctggtgctgt ggcccccctt gtggaccggg gaccgtctgg tcttcgattc gcccgtccag   15900
cggctgtttc ccgagatcgt cgcgtgtcac tccctccggg aacacgcgca cgtctgccgg   15960
ctgcgcaata ccgcgtccgt caaggtgctg ctggggcgca agagcgacag cgagcgcggg   16020
gtggccggtg ccgcgcgggt cgttaacaag gtgttggggg aggacgacga gaccaaggcc   16080
gggtcggccg cctcgcgcct cgtgcggctt atcatcaaca tgaagggcat gcgccacgta   16140
ggcgacatta acgacaccgt gcgtgcctac ctcgacgagg ccggggggca cctgatagac   16200
gccccggccg tcgacggtac cctccctgga ttcggcaagg gcggaaacag ccgcgggtct   16260
gcgggccagg accagggggg gcgggcgccg cagcttcgcc aggccttccg cacggccgtg   16320
gttaacaaca tcaacggcgt gttggagggc tatataaata acctgtttgg aaccatcgag   16380
cgcctgcgcg agaccaacgc gggcctggcg acccaattgc aggagcgcga ccgcgagctc   16440
cggcgcgcaa cagcggggc cctggagcgc cagcagcgcg cggccgacct ggcggccgag   16500
tccgtgaccg gtggatgcgg cagccgccct gcggggcgg acctgctccg ggccgactat   16560
gacattatcg acgtcagcaa gtccatggac gacgacacgt acgtcgccaa cagctttcag   16620
cacccgtaca tcccttcgta cgcccaggac ctggagcgcc tgtcgcgcct ctgggagcac   16680
gagctggtgc gctgttttaa aattctgtgt caccgcaaca accagggcca agagacgtcg   16740
atctcgtact ccagcggggc gatcgccgca ttcgtcgccc cctactttga gtcagtgctt   16800
cgggcccccc gggtaggcgc gcccatcacg ggctccgatg tcatcctggg ggaggaggag   16860
ttatgggatg cggtgtttaa gaaaacccgc ctgcaaacgt acctgacaga catcgcggcc   16920
ctgttcgtcg cggacgtcca gcacgcagcg ctgccccgc ccccctcccc ggtcggcgcc   16980
gatttccggc ccggcgcgtc cccgcggggc cggtccagat cgccggtcgcc cggaagaact   17040 gcgccaggcg cgccggacca gggcgggggc atcgggcacc gggatggccg ccgcgacggc   17100
cgacgatgag gggtcggccg ccaccatcct caagcaggcc atcgccgggg accgcagcct   17160
ggtcgaggcg gccgaggcga ttagccagca gacgctgctc cgcctggcct gcgaggtgcg   17220
ccaggtcggc gaccgccagc cgcggtttac cgccaccagc atcgcgcgcg tcgacgtcgc   17280
gcctgggtgc cggttgcggt tcgttctgga cgggagtccc gaggacgcct atgtgacgtc   17340
ggaggattac tttaagcgct gctgcggcca gtccagttat cgcggcttcg cggtggcggt   17400
cctgacggcc aacgaggacc acgtgcacag cctggccgtg cccccctcg ttctgctgca   17460 ccggttctcc ctgttcaacc ccagggacct cctggacttt gagcttgcct gtctgctgat   17520
gtacctggag aactgccccc gaagccacgc caccccgtcg acctttgcca aggttctggc   17580
gtggctcggg gtcgcgggtc gccgcacgtc cccattcgaa cgcgttcgct gccttttcct   17640
ccgcagttgc cactgggtcc taaacacact catgttcatg gtgcacgtaa aaccgttcga   17700
cgacgagttc gtcctgcccc actggtacat ggccggtac ctgctggcca caaacccgcc   17760
ccccgttctc tcggccctgt tctgtgccac cccgacgagc tcctcattcc ggctgccggg   17820 gccgccccc cgctccgact gcgtggccta taacccgcc gggatcatgg ggagctgctg   17880
ggcgtcggag gaggtgcgcg cgcctctggt ctattggtgg ctttcggaga ccccaaaacg   17940
acagacgtcg tcgctgtttt atcagttttg ttgaatttta ggaaataaac ccggttttgt   18000
ttctgtggcc tcccgacgga tgcgcgtgtc cttcctccgt cttggtgggt gggtgtctgt   18060
gtatcgcgtc ccatctgtgc ggagagggg ggcatgtcgg cacgtattcg gacagactca   18120
```

-continued

```
agcacacacg gggagcgct  cttgtctcag ggcaatgttt ttattggtca aactcaggca 18180
aacagaaacg acatcttgtc gtcaaaggga tacacaaact tccccccctc tccccatact 18240
cccgccagca ccccggtaaa caccaactca atctcgcgca ggatttcgcg caggtgatga 18300
gcgcagtcca cggggggggag cacaagggggc cgcgggtata gatcgacggg gacgccgacc 18360
gactccccgc ctccgggaca gacacgcacg acgcgccgcc agtagtgctc tgcgtccagc 18420
aaggcgccgc cgcggaaggc agtgggggggc aaggggtcgc tagcctcaaa gggggacacc 18480
cgaacgctcc agtactccgc gtccaaccgt ttattaaacg cgtccacgat aaggcggtcg 18540
caggcgtcct ccataaggcc ccgggccgtg agtgcgtcct cctccggcac gcctgccgtt 18600
gtcaggccca ggacccgtcg cagcgtgtcg cgtacgaccc cggccgccgt ggtgtacgcg 18660
ggcccgcgga gaggaaatcc cccaagatgg tcagtgttgt cgcgggagtt ccagaaccac 18720
actcccgcct ggttccaggc gactgcgtgg gtgtagacgc cctcgagggc caggcacagt 18780
gggtgccgca gccggaggcc gttggcccta agcacggctc ccacggccgt ctcgatggcc 18840
cgccgggcgt cctcgatcac cccggaagcc gcatccgcgt cttgggggtc cacgttaaag 18900
acaccccaga acgcacccccc atcgcccccg cagaccgcga acttcaccga gctggccgtc 18960
tcctcgatct gcaggcagac ggcggccatt accccaccca ggagctgccg cagcgcaggg 19020
caggcgtcgc acgtgtccgg gaccaggcgc tccaagacgg ccccggccca gggctctgag 19080
ggagcggcca ccaccagcgc gtccagtctt gctaggcccg tccggccgtg ggggtccgcc 19140
agcccgctcc ccccgaggtc ggccagggcc gccaggagct gggcgcgaag tccggggaag 19200
caaaaccgcg ccgtccagac gggcccgacg gccgcgggcg ggtctaacag ttggatgatt 19260
ttagtggcgg gatgccaccg cgccaccgcc tcccgcaccg cgggcaggag gcatccggct 19320
gccgccgagg ccacgccggg ccaggctcgc ggggggggagga cgaccctggc ccccaccgcg 19380
ggccaggccc ccaggagcgc ggcgtaagcg gccgcggccc cgcgcaccag gtcccgtgcc 19440
gactcggccg tggccggcac ggtgaacgtg ggccaacccg gaaaccccag gacggcaaag 19500
tacgggacgg gtccccccccg gacctcaaac tcgggcccca gaaaggcaaa gacggggggcc 19560 agggcccccgg gggcggcgtg gaccgtggta tgccactgcc ggaaaagggc gacgagcgc 19620 ggcgcggaga acttctcgcc ggcgcttaca aagtagtcgt aatcgcgggg cagcagcacc 19680
cgtgccgtga ctcgttgcgg gtgcccgcgt ggccgcaggc ccacctcgca cacctcgacc 19740
aggtccccga acgcgccctc cttcttgatc ggcggaaacg caagagtctg gtattcgcgc 19800
gcaaatagcg cggttccggt ggtgatgtta acggtcagcg aagcggcgga cgcgcactgg 19860
ggggtgtcgc gaatggccgc caggcgcgcc cacgccagcc gcgcgtcggg atgctcggca 19920
acgcgcgccg ccaggccat anggtcgatg tcaatgttgg cctccgcgac caggagagcg 19980
gcgcgagggg cggcgggcgg gccccacgac gctctctcaa cttcaccac cagtcccgtg 20040 cgtgggtccg agccgatacg cagcgggggcg aacaggggcca ccggcccggt ctggcgctcc 20100
agggccgcca ggacgcacgc gtacagcgcc cgccacagag tcgggttctc cagggggctcc 20160 agcgggggagg cggccggcgt cgtcgcggcg cgggcggccg ccacgacggc ctggacggag 20220
acgtccgcga agccgtagaa atcccgcagc tccgtcgcgg tgacggagac ctccgcaaag 20280
cgcgcgcgac cctcccctgc ggcgttgcga catacaaaat acaccagggc gtggaagtac 20340
tcgcgagcgc gggggggggcag ccataccgcg taaagggtaa tggcgctgac gctctcctcc 20400
acccacacga tatctgcggt gtccatcgca cggcccctaa ggatcacggg cggtctgtgg 20460
gtcccatgct gccgtgcctg gccgggcccg gtgggtcgcg gaaaccggtg acggggggggg 20520
```

```
ggcggttttt ggggttgggg tggggtgggg aaacggcccg ggtccggggg ccaacttggc   20580
ccctcggtgc gttccggcaa cagcgccgcc ggtccgcgga cgaccacgta ccgaacgagt   20640
gcggtcccga gacttatagg gtgctaaagt tcaccgcccc ctgcatcatg ggccaggcct   20700
cggtggggag ctccgacagc gccgcctcca ggatgatgtc agcgttgggg ttggcgctgg   20760
atgagtgcgt gcgcaaacag cgcccccacg caggcacgcg tagcttgaag cgcgcgcccg   20820
caaactcccg cttgtgggcc ataagcaggg cgtacagctg cctgtgggtc cggcaggcgc   20880
tgtggtcgat gtggtgggcg tccaacaacc ccacgattgt ctgtttggtg aggtttttaa   20940
cgcgccccgc cccgggaaac gtctgcgtgc ttttggccat ctgcacgcca aacagttcgc   21000
cccagattat cttgaacagc gccaccgcgt ggtccgtctc gctaacggac ccgcgcgggg   21060
gacagccgct tagggcgtcg cgacgcgct tgacggcttc ctccgagagc agaagtccgt   21120
cggttacgtt acagtggccc agttcgaaca ccagctgcat gtagcggtcg tagtggggggg   21180 tcagtaggtc cagcacgtca tcggggccga aggtcctccc agatccccg gccgccgagt   21240 cccaatgcag gcgcgcggcc atggtgctgc acaggcacaa cagctcccag acgggggtta   21300
cgttcagggt gggggggcagg gccacgagct ccagctctcc ggtgacgttg atcgtgggga   21360
tgacgcccgt ggcgtagtgg tcatagatcc gccgaaatat ggcgctgctg cgggtggcca   21420
tgggaacgcg gagacaggcc tccagcaacg ccagtaaat aaaccgcgtg cgtcccatca   21480
ggctgttgag gttgcgcatg agcgcgacaa tttccgccgg cgcgacatcg gaccggaggt   21540
atttttcgac gaaaagaccc acctcctccg tctcggcggc ctgggccggc agcgacgcct   21600
cgggatcccg gcaccgcagc tcccgtagat cgcgctgggc cctgagggcg tcgaaatgta   21660
cgccccgcaa aaacagacag aagtcctttg gggtcaggt atcgtcgtgt ccccagaagc   21720
gcacgcgtat gcagtttagg gtcagcagca tgtgaaggat gttaaggctg tccgagagac   21780
acgccagcgt gcatctctca aagtagtgtt tgtaacggaa tttgttgtag atgcgcgacc   21840
cccgccccag cgacgtgtcg catgccgacg cgtcacagcg ccccttgaac cggcgacaca   21900
gcaggtttgt gacctgggag aactgcgcgg gccactggcc gcaggaactg accacgtgat   21960
taaggagcat gggcgtaaag acgggctccg agcgcgcccc ggagccgtcc atgtaaatca   22020
gtagctcccc cttgcggagg gtgcgcaccc gtcccaggga ctggtacacg gacaccatgt   22080
ccggtccgta gttcatgggt tttacgtagg cgaacatgcc atcaaagtgc aggggatcga   22140
agctgaggcc cacggttacg accgtcgtgt atataaccac gcggtattgg ccccacgtgg   22200
tcacgtcccc gaggggggtg agcgagtgaa gcaacagcac gcggtccgta aactgacggc   22260
agaaccgggc cacgatctcc gcgaaggaga ccgtcgacga aaaaatgcag atgttatcgc   22320
ccccgccaag gcgcgcttcc agctccccaa agaacgtggc cccccgggcg tccggagagg   22380
cgtccggaga cgggccgctc ggcggcccgg gcgggcgcag ggcagcctgc aggagctcgg   22440
tccccagacg cgggagaaac aggcaccggc gcgccgaaaa cccgggcatg gcgtactcgc   22500
cgaccaccac atgcacgttt ttttcgcccc ggagaccgca caggaagtcc accaactgcg   22560
cgttggcggt tgcgtccatg gcgatgatcc gaggacaggt gcgcagcagg cgtagcatta   22620
acgcatccac gcggcccagt tgctgcatcg ttggcgaata gagctggccc agcgtcgaca   22680
taacctcgtc cagaacgagg acgtcgtagt tgttcagaag gttggggccc acgcgatgaa   22740
ggctttccac ctggacgata agtcggtgga aggggcggtc gttcataatg taattggtgg   22800
atgagaagta ggtgacaaag tcgaccaggc ctgactcagc gaaccgcgtc gccagggtct   22860
```

-continued

```
gggtaaaact ccgacgacag gagacgacga gcacactcgt gtccggagag tggatcgctt    22920
cccgcagcca gcggatcagc gcggtagttt ttcccgaccc cattggcgcg cggaccacag    22980
tcacgcacct ggccgtcggg gcgctcgcgt tggggaaggt gacgggtccg tgctgctgcc    23040
gctcgatcgt tgttttcggg tgaacccggg gcacccattc ggccaaatcc cccccgtaca    23100
acatccgcgc tagcgatacg ctcgacgtgt actgttcgca ctcgtcgtcc ccaatgggac    23160 gccccggcccc cagaggatct cccgactccg cgcccccccac gaaaggcatg accggggcgc    23220
ggacggcgtg gtgggtctgg tgtgtgcagg tggcgacgtt tgtggtctct gcggtctgcg    23280 tcacgggggct cctcgtcctg gcctctgtgt tccgggcacg gtttccctgc ttttacgcca    23340
cggcgagctc ttatgccggg gtgaactcca cggccgaggt gcgcggggggt gtagccgtgc    23400 ccctcaggtt ggacacgcag agccttgtgg gcacttatgt aatcacggcc gtgttgttgt    23460
tggccgcggc cgtgtatgcc gtggtcggcg ccgtgacctc ccgctacgac cgcgccctgg    23520
acgcgggccg ccgtctggct gcggcccgca tggccatgcc gcacgccacg ctgatcgccg    23580
gaaacgtctg ctcttggttg ctgcagatca ccgtcctgtt gctggcccat cgcaccagcc    23640
agctggccca cctggtttac gtcctgcact ttgcgtgtct ggtgtatttt gcggcccatt    23700
tttgcaccag ggggggtcctg agcgggacgt atctgcgtca ggtgcacggc ctgatggagc    23760 cggcccccgac tcatcatcgc gtcgttggcc cggctcgagc cgtgctgaca aacgccttgc    23820
tgttgggcgt cttcctgtgc acggccgacg ccgcggtatc cctgaatacc atcgccgcgt    23880
tcaactttaa tttttcggcc ccgggcatgc tcatatgcct gaccgtgctg ttcgcccttc    23940
tcgtcgtatc gctgttgttg gtggtcgagg gggtgttgtg tcactacgtg cgcgtgttgg    24000 tgggcccccca cctggggggc gtggccgcca cgggcatcgt cggcctggca tgcgagcact    24060
attacaccaa cggctactac gttgtggaga cgcagtggcc ggggggcccag acgggagtcc    24120 gcgtcgccct cgccctggtc gccgcctttg ccctcggcat ggccgtgctc cgctgcaccc    24180
gcgcctatct gtatcacagg cggcaccaca ccaaatttttt tatgcgcatg cgcgacacgc    24240
gacaccgcgc acattccgcc ctcaagcgcg tacgcagttc catgcgcgga tcgcgagacg    24300
gccgccacag gcccgcaccc ggcagcccgc ccgggattcc cgaatatgcg gaagacccct    24360
acgcgatctc atacggcggc cagctcgacc ggtacggaga ttccgacggg gagccgattt    24420
acgacgaggt ggcggacgac caaaccgacg tattgtacgc caagatacaa caccccgcggc    24480 acctgcccga cgacgagccc atctatgaca ccgttgggggg gtacgacccc gagcccgccg    24540 aggacccccgt gtacagcacc gtccgccgtt ggtagctgtt tggttccgtt ttaataaacc    24600
gtttgtgttt aacccgaccg tggtgtatgt ctggtgtgtg gcgtccgatc ccgttactat    24660
caccgttccc cccaaacccc ggcgattgtg ggttttttta aaaacgacac gcgtgcgacc    24720
gtatacagaa cattgttgtt ttttattcgc tatcggacat gggggggtgga aactgggtgg    24780 cggggcaggc gcctccgggg gttcgccggt gagtgtggcg cgaggggggga tccgacgaac    24840 gcaggcgctg tctccccggg gcccgcgtaa ccccgcgcat atccgggggc acgtagaaat    24900
taccttcctc ttcggactcg atatccacga cgtcaaagtc gtgggcggtc agcgagacga    24960
cctccccgtc gtcggtgatg aggacgttgt ttcggcagca gcaggccggg gtcccggaga    25020
acgagaggcc catagctcgg cgagcgtgtc gtcgaacgcc aggcggctgc ttcgctgtat    25080
ggccttatag atctccggat cgatgcggac gggggtaatg atcagggcga tcggaacggc    25140
ctggttcggg agaatggacg ccttgctggg tcctgcggcc ccgagagccc cggcgccgtc    25200
ctccaggcgg aacgttacgc cctcctccgc gctagtgcgg tgcctgccga taaacgtcac    25260
```

-continued

```
cagatgcggg tggggggggc agtcgggaa gtggctgtcg agcacgtagc cctgcaccaa   25320
gatctgctta aagttcgggt gacgggggtt cgcgaagacg ggctcgcggc gtaccagatc   25380
cccggagctc caggacacgg gggagatggt gtggcgtccg aggtcggggg cgccaaacag   25440
aagcacctcc gagacaacgc cgctatttaa ctccaccaag gcccgatccg cggcggagca   25500
ccgccttttt tcgcccgagg cgtgggcctc tgaccaggcc tggtcttgcg tgacgagagc   25560
ctcctccggg ccggggacgc gcccgggcgc gaagtatcgc acgctgggct tcgggatcga   25620
ccggataaat gcccggaacg cctccgggga ccggtgtgcc atcaagtcct cgtacgcgga   25680
ggccgtgggg tcgctggggt ccatgggggtc gaaagcgtac ttggcccggc atttgacctc   25740
gtaaaaggcc aggggggtct tggggactgg ggccaagtag ccgtgaatgt cccgaggaca   25800
gacgagaata tccagggacg ccccgaccat ccccgtgtga ccgtccatga ggaccccaca   25860
cgtatgcacg ttctcttcgg cgaggtcgcc gggttcgtgg aagataaagc gccgcgtgtc   25920
ggcgccggcc tcgccgccgt cgtccgcgcg gcccacgcag tagcgaaaca gcaggcttcg   25980
ggccgtcggc tcgttcaccc gcccgaacat caccgccgaa gactgtacat ccggccgcag   26040
gctggcgttg tgcttcagcc actggggcga gaaacacgga ccctgggggc cccagcggag   26100
ggtggatgcg gtcgtgaggc cccgccggag cagggcccat agctggcagt cggcctggtt   26160
ttgcgtggcc gcctcgtaaa accccatgag gggccggggc gccacggcgt ccgcggcggc   26220
cgggggcccg cggcgcgtca ggcgccatag gtgccggccg agtccgcggt ccaccatacc   26280
cgcctcctcg aggaccacgg ccagggaaca cagataatcc aggcgggccc agaggggacc   26340
gatggccaga ggggcgcgga cgccgcgcag caacccgcgc aggtggcgct cgaacgtctc   26400
ggctagtata tgggagggca gcgcgttggg gatcaccgac gccgaccaca tagagtcaag   26460
gtccggggag tcgggatcgg cgtccgggtc gcgggcgtgg gtgcccccag gagatagcgg   26520
aatgtctggg gtcggaggcc ctgaggcgtc agaaagtgcc ggcgacgcgg cccgggggctt   26580 ttcgtctgcg gtgtcggtgg cgtgctgatc acgtgggggg ttaacgggcg aatgggagct   26640
cgggtccaca gctgacgtcg tctggggtgg ggggggcagg ggacggaagg tggttgttag   26700
cggaagactg ttagggcggg ggcgcttggg ggggctgtcg gggccacgag gggtgtcctc   26760
ggccagggcc caggaacgct tagtcacggt gcgtcccggc ggacatgctg ggcctcccgt   26820
ggactccatt tccgagacga cgtgggggga gcggtggttg agcgcgccgc cgggtgaacg   26880
ctgattctca cgacagcgcg tgccgcgcgc acgggttggt gtgacacagg cgggacacca   26940
gcaccaggag aggcttaagc tcgggaggca gcgccaccga cgacagtatc gccttgtgtg   27000
tgtgctggta atttatacac cgatccgtaa acgcgcgccg aatcttggga ttgcggaggt   27060
ggcgccggat gccctctggg acgtcatacg ccaggccgtg ggtgttggtc tcggccgagt   27120
tgacaaacag ggctgggtgc agcacgcggc gataggcgag cagggccagg gcgaagtcca   27180
gcgacagctg gttgttgaaa tactggtaac cgggaaaccg ggtcacgggt acgcccaggc   27240
tcggggcgac gtacacgcta accaccaact ccagcagcgt ctggccaagg gcgtacaggt   27300
caaccgctaa cccgacgtcg tgcttcaggc ggtggttggt aaattcggcc cgttcgttgt   27360
taaggtattt caccaacagc tccgggggct ggttataccc gtgacccacc agggtgtgaa   27420
agttggctgt ggttagggcg gtgggcatgc caaacatccg gggggacttg aggtccggct   27480
cctggaggca aaactgcccc cgggcgatcg tggagttgga gttgagggtg acgaggctaa   27540
agtcggcgag gacggcccgc cggagcgaga cggcgtccga ccgcagcatg acgaggatgt   27600
```

```
tggcgcactt gatatccagg tggctgatcc cgcaggtggt gtttaaaaac acaacggcgc   27660
gggccagctc cgtgaagcac tggtggaggg ccgtcgagac cgaggggttt gttgtgcgca   27720
gggacgccag ttggccgata tacttaccga ggtccatgtc gtacgcgggg aacactatct   27780
gtcgttgttg cagcgagaac ccgaggggcg cgatgaagcc gcggatgttg tgggtgcggc   27840
cggcgcgtag agcgcactcc ccgaccaaca gggtcgcgat gagctcaacg gcaaaccact   27900
ccttttcctt tatggtctta acggcaagct tatgttcgcg aatcagttgg acgtcgccgt   27960
atcccccaga cccccgaag cttcgggccc cggggatctc gagggtcgtg tagtgtaggg   28020
cggggttgat ggcgaacacg gggctgcata gcttgcggat gcgcgtgagg gtaaggatgt   28080 gcgagggga cgagggggt gcggttaacg ccgcctggga tctgcgcagg ggcgggcggt   28140
tcagtttggc cgccgtaccg ggcgtctcgg gggacgcgcg gcgatgagac gagcggctca   28200
ttcgccatcg ggatagtccc gcgcgaagcc gctcgcggag gccggatcgg tggcgggacc   28260
cgtgggagga gcgggagccg gcggcgtcct ggagagaggg gccgctgggg cgcccggagg   28320
ccccgtgtgg gttggagtgt atgtaggatg cgagccaatc cttgaaggac tgttggcgtg   28380
caccttgggg gctgaggtta gctgccacat gaccagcagg tcgctgtctg cgggactcat   28440
ccatccttcg gccaggtcgc cgtcttccca cagagaagcg ttggtcgctg cttcctcgag   28500
ttgctcctcc tggtccgcaa gacgatcgtc cacggcgtcc aggcgctcac caagcgccgg   28560
atcgaggtac cgtcggtgtg cggttagaaa gtcacgacgc gccgcttgct cctccacgcg   28620
aattttaaca caggtcgcgc gctgtcgcat catctctaag cgcgcgcggg actttagccg   28680
cgcctccaat tccaagtggg ccgcctttgc agccataaag gcgccaacaa accgaggatc   28740
ttgggtgctg acgccctccc ggtgcagctg caggtctg tccttgtaaa tctcggctcg   28800
gaggtgcgtc tcggccaggc gtcggcgcag ggccgcgtgg gcggcatctc ggtccattcc   28860
gccaccctgc gggcgacccg gggggtgctc tgatagtctc gcgtgcccaa ggcccgtgat   28920
cggggtactt cgccgccgcg acccgccacc cggtgtgcgc gatgtttggt cagcagctgg   28980
cgtccgacgt ccagcagtac ctggagcgcc tcgagaaaca gaggcaactt aaggtgggcg   29040
cggacgaggc gtcggcgggc ctcacaatgg gcggcgatgc cctacgagtg cccttttag   29100 atttcgcgac cgcgaccccc aagcgccacc agaccgtggt cccgggcgtc gggacgctcc   29160
acgactgctg cgagcactcg ccgctcttct cggccgtggc gcggcggctg ctgtttaata   29220
gcctggtgcc ggcgcaacta aaggggcgtg atttcggggg cgaccacacg gccaagctgg   29280
aattcctggc ccccgagttg gtacgggcgg tggcgcgact gcggtttaag gagtgcgcgc   29340
cggcggacgt ggtgcctcag cgtaacgcct actatagcgt tctgaacacg tttcaggccc   29400
tccaccgctc cgaagccttt cgccagctgg tgcactttgt gcgggacttt gcccagctgc   29460
ttaaaacctc cttccgggcc tccagcctca cggagaccac gggcccccca aaaaaacggg   29520
ccaaggtgga cgtggccacc cacggccgga cgtacggcac gctggagctg ttccaaaaaa   29580
tgatccttat gcacgccacc tactttctgg ccgccgtgct cctcgggggac cacgcggagc   29640 aggtcaacac gttcctgcgt ctcgtgtttg agatccccct gtttagcgac gcggccgtgc   29700
gccacttccg ccagcgcgcc accgtgtttc tcgtcccccg cgccacggc aagacctggt   29760 ttctagtgcc cctcatcgcg ctgtcgctgg cctccttcg ggggatcaag atcggctaca   29820
cggcgcacat ccgcaaggcg accgagccgg tgtttgagga gatcgacgcc tgcctgcggg   29880
gctggttcgg ttcggcccga gtggaccacg ttaaagggga aaccatctcc ttctcgtttc   29940 cggacggggtc gcgcagtacc atcgtgtttg cctccagcca caacacaaac gtaagtcctc   30000
```

-continued

```
ttttctttcg catggctctc ccaaggggcc ccgggtcgac ccgacccaca cccacccacc   30060
cacccacata cacacacaac cagacgcggg aggaaagtct gccccgtggg cactgatttt   30120
tattcgggat cgcttgagga ggcccgggca acggcccggg caacggtggg gcaactcgta   30180
gcaaataggc gactgatgta cgaagagaag acacacaggc gccacccggc gctggtcggg   30240
gggatgttgt ccgcgccgca ccgtcccccg acgacctctt gcagacggtc cgtgatgcaa   30300
ggacggcggg gggcctgcag cagggtgacc gtatccacgg gatggccaaa gagaagcgga   30360
cacaggctag catccccctg gaccgccagg gtacactggg ccatcttggc ccacagacac   30420
ggggcgacgc agggacagga ctccgttacg acggaggaga gccacagtgc gttggcggaa   30480
tcgatgtggg gcggcggggc gcaggactcg cagccccccg ggtggttggt gatcctggcc   30540
aggagccatc ccagatggcg ggccctgctt cccggtggac agagcgaccc caggtcgctg   30600
tccatggccc agcagtagat ctggccgctg gggaggtgcc accaggcccc cgggcccaag   30660
gcgcaacacg cgcccggctc cgggggggtc ttcgcgggga ccagatacgc gccatccagc   30720
tcgccgacca ctggctcctc cgcgagctgt tcggtggttg ggtcgggggt ttcctccggg   30780
ggggtggccg cccgtatgcg ggcgaacgtg agggtgcaca ggagcggggt cagggggtgc   30840
gtcacgctcc ggaggtggac gatcgcgcag tagcggcgct cgcggttaaa gaaaaagagg   30900
gcaaagaagg tgttcggggg caaccgcagc gccttggggc gcgtcagata cagaaaaatc   30960
tcgcagaaga gggcgcgccc ggggtctggg ttaggaaggg ccacctgaca cagaggctcg   31020
gtgaggaccg ttagacaccg aaagatcttg agccgctcgt ccgccgaac gacgcgccac   31080 acaaagacgg agttgacaat gcgcgcgata gagtcgacgt ccgtccccag gtcgtcgact   31140
ctgtcgcgcg tgccgcgagc tccggcccgg gaatccggcc ggggcaaggt ccccggggga   31200
ccaggcggcg ccaggggccg ccggggtccc agctgcgcca tgccgggggc ggggggaggg   31260
caaaccccag aggcggggc caacggccgcg gggaggagtg ggtgggcgag gtggccgggg   31320
gaaggcgccc gctagcgaga acggccgttc ccggacgaca ccttgcgaca aaacctaagg   31380
acagcggccc gcgcgacggg gtccgagagg ctaaggtagg ccgcgatgtt aatggtgaac   31440
gcaaagccgc cgggaaagac aactatgcca cagaggcggc gattaaaccc caggcagagg   31500
taggcgtagc tttccccggg caggtattgc tcgcagaccc tgcgtggggc tgtggagggg   31560
acggcctcca tgaagcgaca tttactctgc tcgcgtttac tgacgtcacc atccatcgcc   31620
acggcgattg gacgattgtt aagccgcagc gtgtctccgc ttgtgctgta gtagtcaaaa   31680
acgtaatggc cgtcggagtc ggcaaagcgg gccgggaggc cgtcgccgag cgggacgacc   31740
cgccgccccc gaccgccccg tcccccagg tgtgccagga cggccagggc atacgcggtg   31800 tgaaaaagg cgtcggggc ggtcccctcg acggcgcgca tcaggttctc gaggagaatg   31860
gggaagcgcc tggtcacctc ccccagccac gcgcgttggt cggggccaaa gtcatagcgc   31920
aggcgctgtg agattcgagg gccgccctga agcgcgccc ggatggcctg gcccaggggc   31980
cggaggcacg ccagatgtat gcgcgcagta aaggcgacct cggcggcgat gtcaaagggc   32040
ggcaggacgg ggcgcgggtg gcgcagggc acctcgagcg cgggaaagcg gagcagcagc   32100
tccgcctgcc cagcgggaga cagctggtgg gggcgcacga cgcgttctgc ggcgcaggcc   32160
tcggtcaggg ccgtggccag cgccgaggac agcagcggag ggcgggcgcg tcgcccgccc   32220
cacgccacgg agttctcgta ggagacgacg acgaagcgct gcttggttcc gtagtggtgg   32280
cgcaggacca cggagataga acgacggctc cacagccagt ccggccggtc gccgccggcc   32340
```

-continued

```
agggcttccc atccgcgatc caaccactcg accagcgacc gcggctttgc ggtaccaggg    32400
gtcagggtta gaacgtcgtt caggatgtcc tcgccccggg gcccgtgggg cactggggcc    32460
acaaagcggc ccccgcctgg gggctccaga cccgccaaca ccgcatctgc gtcagccgcc    32520
cccatggcgc ccccgctgac ggcctggtga accaggcgc cctggcggag ccccgatgca     32580
acgccacagg ccgcacgccc ggtccgagcg cggaccgggt ggcggcgggt gacgtcctgc    32640
actgcccgct gaaccaacgc gaggatctcc tcgttctcct gcgcgatgga cacgtcctgg    32700
gccgcggtcg tgtcgccgcc gggggccgtc agctgctcct ccggggagat ggggggggtcg   32760 gacgccccga cgatgggcgg gtctgcgggc gcccccgcgt ggggccggc caagggctgc     32820 ggacgcgggg acgcgctttc ccccagaccc atggacaggt gggccgcagc ctccttcgcg    32880
gccggcgggg cggcggcgcc aagcagagcg acgtagcggc acaaatgccg acagacgcgc    32940
atgatgcgcg tgctgtcggc cgcgtagcgc gtgttggggg ggacgagctc gtcgtaacta    33000
aacagaatca cgcgggcaca gctcgccccc gagccccacg caaggcgcag cgccgccacg    33060
gcgtacgggt catagacgcc ctgtgcgtca cacaccacgg gcaaggagac gaacaacccc    33120
ccggcgctgg acgcacgcgg aaggaggcca gggtgtgccg gcacgacggg ggccagaagc    33180
tcccccaccg catccgcggg cacgtaggcg gcaaacgccg tgcaccacgg ggtacagtcg    33240
ccggtggcat gagcccgagt ctggatttcg acctggaagt ttgcggccgt cccgagtccg    33300
gggcggccgc gcatcagggc ggccagaggg attcccgcgg ccgccaggca ctcgctggat    33360
atgatgacgt gaaccaaaga cgagggccga cccgggacgt ggccgagatc gtactggacc    33420
tcgttggcca agtgcgcgtt catggttcgg gggtgggtgt gggtgtgtag gcgatgcggg    33480
tcccccgagt ccgcgggaag ggcgcgcggtt tggcgcgcgt atgcgtattc gccaacggag   33540
gcgtgcgtgc ttatgcgcgg cgcgtttctt ctgtctccag ggaatccgag gccaggactt    33600
taacctgctc tttgtcgacg aggccaactt tattcgcccg gatgcggtcc agacgattat    33660
gggctttctc aaccaggcca actgcaagat tatcttcgtg tcgtccacca acaccgggaa    33720
ggccagtacg agcttttttgt acaacctccg cggggccgcc gacgagcttc tcaacgtggt    33780
gacctatata tgcgatgatc acatgccgcg ggtggtgacg cacacaaacg ccacggcctg    33840
ttcttgttat atcctcaaca agcccgtttt catcacgatg gacggggcgg ttcgccggac    33900
cgccgatttg tttctggccg attccttcat gcaggagatc atcggggggcc aggccaggga   33960 gaccggcgac gaccggcccg ttctgaccaa gtctgcgggg gagcggtttc tgttgtaccg    34020
cccctcgacc accaccaaca gcggcctcat ggccccgat ttgtacgtgt acgtggatcc     34080
cgcgttcacg gccaacaccc gagcctccgg gaccggcgtc gctgtcgtcg ggcggtaccg    34140
cgacgattat atcatcttcg ccctggagca cttttttctc cgcgcgctca cgggctcggc    34200
ccccgccgac atcgcccgct gcgtcgtcca cagtctgacg caggtcctgg ccctgcatcc    34260
cggggcgttt cgcggcgtcc gggtggcggt cgagggaaat agcagccagg actcggccgt    34320
cgccatcgcc acgcacgtgc acacagagat gcaccgccta ctggcctcgg aggggggccga   34380 cgcgggctcg ggccccgagc ttctcttcta ccactgcgag cctcccggga gcgcggtgct    34440
gtaccccttt ttcctgctca acaaacagaa gacgcccgcc tttgaacact ttattaaaaa    34500
gtttaactcc gggggcgtca tggcctccca ggagatcgtt tccgcgacgg tgcgcctgca    34560
gaccgacccg gtcgagtatc tgctcgagca gctgaataac ctcaccgaaa ccgtctcccc    34620
caacacggac gtccgtacgt attccggaaa acggaacggc gcctcggatg accttatggt    34680
cgccgtcatt atggccatct accttgcggc ccaggccgga cctccgcaca cattcgctcc    34740
```

```
catcacacgc gtttcgtgag cgcccaataa acacacccag gtatgctacg cacgaccacg    34800
gtgtcgcctg ttaaggggg gggaagggg tgttggcggg aagcgtggga acacgggga      34860 ttctctcacg accggcacca gtaccacccc cctgtgaaca cagaaacccc aacccaaatc    34920
ccataaacat acgacacaca ggcatatttt ggaatttctt aggttttttat ttatttaggt    34980 atgctggggt ttctccctgg atgcccaccc ccaccccccc ccgtgggtct agccgggcct    35040
tagggatagc gtataacggg ggccatgtct ccggaccgca caacggccgc gccgtcaaag    35100
gtgcacaccc gaaccacggg agccagggcc aaggtgtctc ctagttggcc cgcgtgggtc    35160
agccaggcga cgagcgcctc gtagagcggc agccttcgct ctccatcctg catcagggcc    35220
ggggcttcgg ggtgaatgag ctgggcggcc tcccgcgtga cactctgcat ctgcaggaga    35280
gcgttcacgt acccgtcctg ggcacttagc gcaaagagcc gggggattag cgtaaggatg    35340
atggtggttc cctccgtgat cgagtaaacc atgttaagga ccagcgatcg cagctcggcg    35400
tttacggggc cgagttgttg gacgtccgcc agcagcgaga ggcgactccc gttgtagtac    35460
agcacgttga ggtctggcag ccctccgggg tttctggggc tggggttcag gtcccggatg    35520
cccctggcca cgagccgcgc cacgatttcg cgcgccaggg gcgatggaag cggaacggga    35580
aaccgcaacg tgaggtccag cgaatccagg cgcacgtccg tcgcttggcc ctcgaacacg    35640
ggcgggacga ggctgatggg gtccccgtta cagagatcta cggggaggt gttgcgaagg      35700 ttaacggtgc cggcgtgggt gaggcccacg tccaggggc aggcgacgat tcgcgtggga      35760
agcacccggg tgatgaccgc ggggaagcgc cttcggtacg ccagcaacag ccccaacgtg    35820
tcgggactga cgcctccgga gacgaaggat tcgtgcgcca cgtcggccag cgtcagttgc    35880
cggcggatgg tcggcaggaa taccacccgc ccttcgcagc gctgcagcgc cgccgcatcg    35940
gggcgcgaga tgcccgaggg tatcgcgatg tcagtttcaa agccgtccgc cagcatggcg    36000
ccgatccacg cggcagggag tgcagtggtg gttcgggtgg cgggaggagc gcggtggggg    36060
tcagcggcgt agcagagacg ggcgaccaac ctcgcatagg acggggggtg ggtcttaggg    36120
ggttgggagg cgacagggac cccagagcat gcgcggggag gtctgtcggg cccagacgca    36180
ccgagagcga atccgtccat ggagtcccgg cctgggtttt atggggcccg gccctcggaa    36240
tcgcggcttg tcggcgggga caaagggggc ggggctaggg ggcttgcgga aacagaagac    36300
gtgtgggata aaagaatcgc actacccaa ggaagggcgg ggcggtttat tacagagcca      36360
gtcccttgag cggggatgcg tcatagacga gatactgcgc gaagtgggtc tcccgcgcgt    36420
gggcttcccc gttgcgggcg ctgcggagga gggcggggtc gctggcgcag gtgagcgggt    36480
aggcctcctg aaacaggcca cacgggtcct ccacgagttc gcggcacccc gggggcgct      36540 taaactgtac gtcgctggcg gcggtggccg tggacaccgc cgaacccgtc tccacgatca    36600
ggcgctccag gcagcgatgt ttggcggcga tgtcggccga cgtaaagaac ttaaagcagg    36660
ggctgagcac cggcgaggcc ccgttgaggt ggtaggcccc gttatagagc aggtcccgt      36720 acgaaaatcg ctgcgacgcc cacgggttgg ccgtggccgc gaaggcccgg gacgggtcgc    36780
tctggccgtg gtcgtacatg agggcggtga catccccctc cttgtccccc gcgtaaacgc    36840
ccccggcggc gcgtccccgg gggttgcagg gccggcggaa gtagttgacg tcggtcgaca    36900
cgggggtggc gataaactca cacacggcgt cctggccgtg gtccatccct gcgcgccgcg    36960
gcacctgggc gcaccgaac acggggacgg gctgggccgg ccccaggcgg tttcccgcca      37020
cgaccgcgtt ccgcaggtac acggctgccg cgttgtccag tagaggggga gccccgcggc    37080
```

-continued

```
ccaggtaaaa gttttgggga aggttgccca tgtcggtgac ggggttgcgg acggttgccg    37140
tggccacgac ggcggtgtag cccacgccca ggtccacgtt cccgcgcggc tgggtgagcg    37200
tgaagtttac cccccgcca gtttcatgcc gggccacctg gagctggccc aggaagtacg     37260
cctccgacgc gcgctccgag aacagcacgt tctcagtcac aaagcggtcc tgtcggacga    37320
cggtgaaccc aaacccggga tggaggcccg tcttgagctg atgatgcaag gccacgggac    37380
tgatcttgaa gtaccccgcc atgagcgcgt aggtcagcgc gttctccccg gccgcgctct    37440
cgcggacgtg ctgcacgacg ggctgtcgga tcgacgaaaa gtagttggcc cccagagccg    37500
gggggaccag ggggacctgc cgcgacaggt cgcgcagggc cggggggaaa ttggcgcgt     37560 tcgccacgtg gtcggccccg gcgaacagcg cgtggacggg gaggggtaa aaatagtcgc     37620 cattttggat ggtatggtcc agatgctggg gggccatcag caggattccg gcgtgcaacg    37680
ccccgtcgaa tatgcgcatg ttggtggtgg acgcggtgtt ggcgcccgcg tcgggcgccg    37740
ccgagcagag cagcgccgtt gtgcgttcgg ccatgttgtg ggccagcacc tgcagcgtga    37800
gcatggcggg cccgtccact accacgcgcc cgttgtgaaa catggcgttg accgtgttgg    37860
ccaccagatt ggccgggtgc agggggtgcg cggggtccgt cacggggtcg ctggggcaat    37920
cctcgccggg ggtgatctcc gggaccacca tgttctgcag ggtggcgtat acgcggtcga    37980
agcgaacccc cgcggtgcag cagcggcccc gcgagaaggc gggcaccatc acgtagtagt    38040
aaatcttgtg gtgcacggtc cagtccgccc cccggtgcgg ccggtcgtcc gcggcgtccg    38100
cggctcgggc ctgggtgttg tgcagcagct ggccgtcgtt gcggttgaag tccgcggtcg    38160
ccacgttaca cgccgctgcg tacacggggt cgtggccccc cgcgctaacc cggcagtcgc    38220
gatggcggtc cagggccgcg cgccgcatca gggcgtcgca gtcccacacg aggggtggca    38280
gcagcgccgg gtctcgcatt aggtgattca gttcggcttg cgcctgcccg cccagttccg    38340
ggccggtcag ggtaaagtca tcaaccagct gggccagggc ctcgacgtgc gccaccaggt    38400
cccggtacac ggccatgcac tcctcgggaa ggtctccccc gaggtaggtc acgacgtacg    38460
agaccagcga gtagtcgttc acgaacgccg cgcaccgcgt gttgttccag tagctggtga    38520
tgcactggac cacgagccgg gccagggcgc agaagacgtg ctcgctgccg tgtatggcgg    38580
cctgcagcag gtaaaacacc gccgggtagt tgcggtcttc gaacgccccg cgaacggcgg    38640
cgatggtggc gggggccatg gcgtggcgtc ccaccccag cttccaggccc cgggcgtccc    38700 ggaacgccgc cggacatagc gccaggggca agttgccgtt caccacgcgc caggtggcct    38760
ggatctcccc cgggccggcc gggggaacgt cccccccccgg cagctccacg tcggccaccc    38820
ccacgaagaa gtcgaacgcg gggtgcagct caagagccag gttggcgttg tcgggctgca    38880
taaactgctc cggggtcatc tggccttccg cgacccatcg gacccgcccg tgggccaggc    38940
gctgccccca ggcgttcaaa aacagctgct gcatgtctgc ggcggggccg gccggggccg    39000
ccacgtacgc cccgtacgga ttggcggctt cgacggggtc gcggttaagg cccccgaccg    39060
ccgcgtcaac gttcatcagc gaagggtggc acacggtccc gatcgcgtgt tccagagaca    39120
ggcgcagcac ctggcggtcc ttcccccaaa aaaacagctg gcggggcggg aaggcgcggg    39180
gatccgggtg gccgggggcg gggactaggt ccccggcgtg cgcggcaaac cgttccatga    39240
ccggattgaa caggcccagg ggcaggacga acgtcaggtc catggcgccc accaggggt     39300 agggaacgtt ggtggcggcg tagatgcgct tctccagggc ctccaaaaag atcagcttct    39360
cgccgatgga caccagatcc gcgcgcacgc gcgtcgtctg ggggggcgctc tcgagctcgt    39420 ccagcgtctg ccggttcagg tcgagctgct cctcctgcat ctccagcagg tggcggccca    39480
```

-continued

```
cgtcgtccag acttcgcacg gccttgccca tcacgagcgc cgtgaccagg ttggccccgt   39540
tcaggaccat ctcgccgtac gtcaccggca cgtcggcttc ggtgtcctcc actttcagga   39600
aggactgcag gaggcgctgt ttgatcgggg cggtggtgac gagcaccccg tcgaccggac   39660
gcccgcgcgt gtcggcatgc gtcagacggg gcacggccac ggagggctgc gtggccgtgg   39720
tgaggtccac gagccaggcc tcgacggcct cccggcggtg gcccgccttg cccaggaaaa   39780
agctcgtctc gcagaagctt cgctttagct cggcgaccag ggtcgcccgg gccaccctgg   39840
tggccaggcg gccgttgtcc aggtatcgtt gcatcggcaa caacaaagcc aggggcggcg   39900 cctttccag cagcacgtgc agcatctggt cggccgtgcc gcgctcaaac gccccgagga   39960
cggcctggac gttgcgagcg agctgttgga tggcgcgcaa ctggcgatgc gcgctgatac   40020
ccgtcccgtc cagggcctcc cccgtgagca gggcgatggc ctcggtggcc aggctgaagg   40080
cggcgttcag ggcccggcgg tcgataatct tggtcatgta attgtgtgtg ggttgctcga   40140
tggggtgcgg gccgtcgcgg gcaatcagcg gctggtggac ctcgaactgt acgcgcccct   40200
cgttcatgta ggccagctcc ggaaacttgg tacacacgca cgccaccgac aacccgagct   40260
ccagaaagcg cacgagcgac agggtgttgc aatacgaccc caacagggcg tcgaactcga   40320
cgtcatacag gctgtttgca tcggagcgca cgcgggaaaa aaaatcgaac aggcgtcgat   40380
gcgacgccac ctcgatcgtg ctaaggaggg acccggtcgg caccatggcc gcggcatacc   40440
ggtatcccgg agggtcgcgg ttgggagcgg ccatggggtc gcgtggagat cggctgtctc   40500
tagcgatatt ggcccgggga ggctaagatc caccccaacg cccggccacc cgtgtacgtg   40560
cccgacggcc caaggtccac cgaaagacac gacgggcccg gacccaaaaa ggcggggggat   40620 gctgtgtgag aggccgggtg tcggtcgggg gggaaaggca ccgggagaag gctgcggcct   40680
cgttccagga gaacccagtg tccccaacag acccggggac gtgggatccc aggccttata   40740
tacccccccc gccccacccc cgttagaacg cgacgggtgc attcaagatg gccctggtcc   40800
aaaagcgtgc caggaagaaa ttggcagagg cggcaaagct gtccgccgcc gccacccaca   40860
tcgaggcccc ggccgcgcag gctatcccca gggcccgtgt gcgcagggga tcggtgggcg   40920
gcagcatttg gttggtggcg ataaagtgga aaagcccgtc cggactgaag gtctcgtggg   40980
cggcggcgaa caaggcacac agggccgtgc ctcccaaaaa cacggacatc ccccaaaaca   41040
cgggcgccga caacggcaga cgatccctct tgatgttaac gtacaggagg agcgcccgca   41100
ccgcccacgt aacgtagtag ccgacgatgg cggccaggat acaggccggc gccaccaccc   41160
ttccggtcag cccgtaatac atgcccgctg ccaccatctc caacggcttc aggaccaaaa   41220
acgaccaaag gaacagaatc acgcgctttg aaaagaccgg ctgggtatgg ggcggaagac   41280
gcgagtatgc cgaactgaca aaaaagtcag aggtgccgta cgaggacaat gaaaactgtt   41340
cctccagtgg cagttctccc tcctcccccc caaaggcggc ctcgtcgacc agatctcgat   41400
ccaccagagg aaggtcatcc cgcatggtca tggggtgtgc ggtggaggtg gggagaccga   41460
aaccgcaaag ggtcgcttac gtcagcagga tcccgagatc aaagacaccc gggttcttgc   41520
acaaacacca cccgggttgc atccgcggag gcgagtgttt tgataaggcc gttccgcgcc   41580
ttgatataac ctttgatgtt gaccacaaaa cccggaattt acgcctacgc cccaatgccc   41640
acgcaagatg aggtaggtaa ccccccccc gtgggtgtga cgttgcgttt agttcattgg   41700
aggccaaggg gaaaatgggg tggggaggaa acggaaaacc cagtaggccg tgtttgggaac   41760 acgcccgggg ttgtcctcaa aaggcagggt ccatactacg gaagccgtcg ttgtattcga   41820
```

-continued

```
gacctgcctg tgcgacgcac gtcggggttg cctgtgtccg gttcggcccc accgcgtgcg   41880
gcacgcacga ggacgagtcc gcgtgcttta ttggcgttcc aagcgttgcc ctccagtttc   41940
tgttgtcggt gttcccccat acccacgccc acatccaccg tagggggcct ctgggccgtg   42000
tcacgtcgcc gcccgcgatg gagcttagct acgccaccac catgcactac cgggacgttg   42060
tgttttacgt cacaacggac cgaaaccggg cctactttgt gtgcggggggg tgtgtttatt   42120 ccgtggggcg gccgtgtgcc tcgcagcccg gggagattgc caagtttggt ctggtcgttc   42180
gagggacagg cccagacgac cgcgtggtcg ccaactatgt acgaagcgag ctccgacaac   42240
gcggcctgca ggacgtgcgt cccattgggg aggacgaggt gtttctggac agcgtgtgtc   42300
ttctaaaccc gaacgtgagc tccgagctgg atgtgattaa cacgaacgac gtggaagtgc   42360
tggacgaatg tctggccgag tactgcacct cgctgcgaac cagcccgggt gtgctaatat   42420
ccgggctgcg cgtgcgggcg caggacagaa tcatcgagtt gtttgaacac ccaacgatag   42480
tcaacgtttc ctcgcacttt gtgtataccc cgtccccata cgtgttcgcc ctggcccagg   42540
cgcacctccc ccggctcccg agctcgctgg aggccctggt gagcggcctg tttgacggca   42600
tccccgcccc acgccagcca cttgacgccc acaaccccgcg cacggatgtg gttatcacgg   42660
gccgccgcgc cccacgaccc atcgccgggt cggggggcggg gtcgggggggc gcgggcgcca   42720 agcgggccac cgtcagcgag ttcgtgcaag tcaaacacat tgaccgcgtg ggccccgctg   42780
gcgtttcgcc ggcgcctccg ccaaacaaca ccgactcaag ttccctggtg cccgggggccc   42840 aggattccgc cccgcccggc cccacgctaa gggagctgtg gtgggtgttt tatgccgcag   42900
accgggcgct ggaggagccc cgcgccgact ctggcctcac ccgcgaggag gtacgtgccg   42960
tacgtgggtt ccgggagcag gcgtggaaac tgtttggctc cgcggggggcc ccgcgggcgt   43020 ttatcggggc cgcgttgggc ctgagccccc tccaaaagct agccgtttac tactatatca   43080
tccaccgaga gaggcgcctg tcccccttcc ccgcgctagt ccggctcgta ggccggtaca   43140
cacagcgcca cggcctgtac gtccctcggc ccgacgaccc agtcttggcc gatgccatca   43200
acgggctgtt tcgcgacgcg ctggcggccg gaaccacagc cgagcagctc ctcatgttcg   43260
accttctccc cccaaaggac gtgccggtgg gaagcgacgt gcaggccgac agcaccgctc   43320
tgctgcgctt tatagaatcg caacgtctcg ccgtccccgg gggggtgatc tcccccgagc   43380
acgtcgcgta ccttggtgcg ttcctgagcg tgctgtacgc tggccgcggg cgcatgtccg   43440
cagccacgca caccgcgcgg ctgacagggg tgacctccct ggtgctagcg gtgggtgacg   43500
tggaccgtct ttccgcgttt gaccgcggag cggcgggcgc ggccagccgc acgcgggccg   43560
ccgggtacct ggatgtgctt cttaccgttc gtctcgctcg ctcccaacac ggacagtctg   43620
tgtaacagac cccaataaac gtatgtcgct accacaccct tgtgtgtcaa tggacgcctc   43680
tccggggggg aagggaaaac aaagaggggc tgggggagcg gcaccaccgg ggcctgaaca   43740
aacaaaccac agacacggtt acagtttatt cggtcgggcg gagaaacggc cgaagccacg   43800 cccccttttat tcgcgtctcc aaaaaaacg gacacttgtc cggagaacct ttaggatgcc   43860
agccagggcg gcggtaatca taaccacgcc cagcgcagag gcggccagaa acccgggcgc   43920
aattgcggcc acgggctgcg tgtcaaaggc tagcaaatga atgacggttc cgtttggaaa   43980
tagcaacaag gccgtggacg gcacgtcgct cgaaaacacg cttggggcgc cctccgtcgg   44040
cccggcggcg atttgctgct gtgtgttgtc cgtatccacc agcaacacag acatgacctc   44100
cccggccggg gtgtagcgca taaacacggc ccccacgagc cccaggtcgc gctggttttg   44160
ggtgcgcacc agccgcttgg actcgatatc ccgggtggag ccttcgcatg tcgcggtgag   44220
```

-continued

```
gtaggttagg aacagtgggc gtcggacgtc gacgccggtg agcttgtagc cgatcccccg   44280
gggcagaggg gagtgggtga cgacgtagct ggcgttgtgg gtgatgggta ccaggatccg   44340
tggctcgacg ttggcagact gcccccgca ccgatgtgag gcctcaggga cgaaggcgcg    44400
gatcagggcg ttgtagtgtg cccagcgcgt caggtcgag gcgaggccgt gggtctgctg     44460
ggccaggact tcgaccgggg tctcggatcg ggtggcttga gccagcgcgt ccaggataaa   44520
cacgctctcg tctagatcaa agcgcaggga ggccgcgcat ggcgaaaagt ggtccggaag   44580
ccaaaagagg gttttctggt ggtcggcccg ggccagcgcg gtccggaggt cggcgttggt   44640
cgctgcggcg acgtcggacg tacacagggc cgaggctatc agaaggctcc ggcgggcgcg   44700
ttcccgctgc accgccgagg ggacgcccgc caagaacggc tgccggagga cagccgaggc   44760
gtaaaatagc gcccggtgga cgaccggggt ggtcagcacg cggcccccta gaaactcggc    44820
atacagggcg tcgatgagat gggctgcgct gggcgccact gcgtcgtacg ccgaggggct    44880
atccagcacg aaggccagct gatagcccag cgcgtgtaat gccaagctct gttcgcgctc    44940
cagaatctcg gccaccaggt gctggagccg agcctctagc tgcaggcggg ccgtgggatc   45000
caagactgac acattaaaaa acacagaatc cgcggcacag cccgcggccc cgcgggcggc    45060
caacccggca agcgcgcgcg agtgggccaa aaagcctagc aggtcggaga ggcagaccgc    45120
gccgtttgcg tgggcggcgt tcacgaaagc aaaacccgac gtcgcgagca gccccgttag    45180
gcgccagaag agaggggggac gcgggccctg ctcggcgccc gcgtcccccg agaaaaactc    45240
cgcgtatgcc cgcgacagga actgggcgta gttcgtgccc tcctccgggt agccgcccac    45300
gcggcggagg gcgtccagcg cggagccgtt gtcggcccgc gtcagggacc ctaggacaaa   45360
gacccgatac cggggggccgc ccgggggccc gggaagagcc cccggggggt tttcgtccgc    45420
ggggtccccg acccgatcta gcgtctggcc cgcggggacc accatcactt ccaccggagg   45480
gctgtcgtgc atggatatca cgagccccat gaattcccgc ccgtagcgcg cgcgcaccag   45540
cgcggcatcg cacccgagca ccagctcccc cgtcgtccag atgcccacgg gccacgtcga   45600
ggccgacggg gagaaataca cgtacctacc tggggatctc aacaggcccc gggtggccaa   45660
ccaggtcgtg gacgcgttgt gcaggtgcgt gatgtccagc tccgtcgtcg ggtgccgccg   45720
ggccccaacc ggcggtcggg ggggcggtgt atcacgcggc ccgctcgggt ggctcgccgt   45780
cgccacgttg tctccccgcg ggaacgtcag ggcctcgggg tcaggacggg ccgaaaacgt   45840
tacccaggcc cgggaacgca gcaacacgga ggcggttgga ttgtgcaaga gacccttaag   45900
gggggcgacc gcggggggag gctgggcggt cggctcgacc gtgatggggg cgggcaggct    45960
cgcgttcggg ggccggccga gcaggtaggt cttcgagatg taaagcagct ggccggggtc    46020
ccgcggaaac tcgccgtgg tgaccaatac aaaacaaaag cgctcctcgt accagcgaag     46080
aaggggcaga gatgccgtag tcaggtttag ttcgtccggc ggcgccagaa atccgcgcgg   46140 tggttttgg gggtcggggg tgtttggcag ccacagacgc ccggtgttcg tgtcgcgcca   46200
gtacatgcgg tccatgccca ggccatccaa aaaccatggg tctgtctgct cagtccagtc    46260
gtggacctga ccccacgcaa cgcccaaaag aataacccc acgaaccata aaccattccc     46320
catgggggac cccgtcccta acccacgggg cccgtggcta tggcagggct tgccgccccg   46380
acgttggctg cgagccctgg gccttcaccc gaacttgggg gttggggtgg ggaaaaggaa   46440
gaaacgcgcg cgtattggcc ccaatggggt ctcggtgggg tatcgacaga gtgccagccc    46500
tgggaccgaa ccccgcgttt atgaacaaac gacccaacac ccgtgcgttt tattctgtct    46560
```

-continued

```
ttttatttcc gtcatagcgc gggttccttc cggtattgtc tccttccgtg tttcagttag   46620
cctcccccat ctcccgggca aacgtgcgcg ccaggtcgca gatcgtcggt atggagcctg   46680
gggtggtgac gtgggtctgg accatcccgg aggtaagttg cagcagggcg tcccggcagc   46740
cggcgggcga ttggtcgtaa tccaggataa agacgtgcat gggacggagg cgtttggcca   46800
agacgtccaa ggcccaggca aacacgttat acaggtcgcc gttgggggcc agcaactcgg   46860
gggcccgaaa cagggtaaat aacgtgtccc cgatatgggg tcgtgggccc gcgttgctct   46920
ggggctcggc accctggggc ggcacggccg tccccgaaag ctgtccccaa tcctcccgcc   46980
acgacccgcc gccctgcaga taccgcaccg tattggcaag cagcccgtaa acgcggcgaa   47040
tcgcggccaa catagccagg tcaagccgct cgccggggcg ctggcgtttg gccaggcggt   47100
cgatgtgtct gtcctccgga agggccccca acacgatgtt tgtgccgggc aaggtcggcg   47160
ggatgagggc cacgaacgcc agcacggcct gggggtcat gctgcccata aggtatcgcg   47220
cggccgggta gcacaggagg gcggcgatgg gatggcggtc gaagatgagg gtgagggccg   47280
ggggcggggc atgtgagctc ccagcctccc ccccgatatg aggagccaga acggcgtcgg   47340
tcacggcata aggcatgccc attgttatct gggcgcttgt cattaccacc gccgcgtccc   47400
cggccgatat ctcaccctgg tcgaggcggt gttgtgtggt gtagatgttc gcgattgtct   47460
cggaagcccc cagcacctgc cagtaagtca tcggctcggg tacgtagacg atatcgtcgc   47520
gcgaacccag ggccaccagc agttgcgtgg tggtggtttt ccccatcccg tgaggaccgt   47580
ctatataaac ccgcagtagc gtgggcattt tctgctccag gcggacttcc gtggcttctt   47640
gctgccggcg agggcgcaac gccgtacgtc ggttgctatg gccgcgagaa cgcgcagcct   47700
ggtcgaacgc agacgcgtgt tgatggcagg ggtacgaagc catacgcgct tctacaaggc   47760
gcttgccaaa gaggtgcggg agtttcacgc caccaagatc tgcggcacgc tgttgacgct   47820
gttaagcggg tcgctgcagg gtcgctcggt gttcgaggcc acacgcgtca ccttaatatg   47880
cgaagtggac ctgggaccgc gccgccccga ctgcatctgc gtgttcgaat tcgccaatga   47940
caagacgctg ggcggggttt gtgtcatcat agaactaaag acatgcaaat atatttcttc   48000
cggggacacc gccagcaaac gcgagcaacg ggccacgggg atgaagcagc tgcgccactc   48060
cctgaagctc ctgcagtccc tcgcgcctcc gggtgacaag atagtgtacc tgtgccccgt   48120
cctggtgttt gtcgcccaac ggacgctccg cgtcagccgc gtgacccggc tcgtcccgca   48180
gaaggtctcc ggtaatatca ccgcagtcgt gcggatgctc cagagcctgt ccacgtatac   48240
ggtccccatg gagcctagga cccagcgagc ccgtcgccgc cgcggcggcg ctgcccgggg   48300
gtctgcgagc agaccgaaaa ggtcacactc tggggcgcgc gacccgcccg agccagcggc   48360
ccgccaggta ccaccgccg accaaacccc cgcctccacg gagggcgggg gggtgcttaa   48420
gaggatcgcg gcgctcttct gcgtgcccgt ggccaccaag accaaacccc gagctgcctc   48480
cgaatgagag tgtttcgttc cttcccctc ccccgcgtc agacaaaccc taaccaccgc   48540
ttaagcggcc cccgcgaggt ccgaagactc atttggatcc ggcgggagcc acctgacaac   48600
agccccgggg tttccccacg ccagacgccg gtccgctgtg ccatcgctcc ccttcatccc   48660 accccatct tgtccccaaa taaaacaagg tctggtagtt aggacaacga ccgcagttct   48720
cgtgtgttat tgtcgctctc cgcctctcgc agatggaccc gtattgccca tttgacgctc   48780
tggacgtctg ggaacacagg cgcttcatag tcgccgattc ccgaaacttc atcacccccg   48840
agttcccccg ggactttttgg atgtcgcccg tctttaacct ccccggggag acggcggcgg   48900
agcaggtggt cgtcctgcag gcccagcgca cagcggctgc cgctgccctg gagaacgccg   48960
```

-continued

```
ccatgcaggc ggccgagctc cccgtcgata tcgagcgccg gttacgcccg atcgaacgga   49020
acgtgcacga gatcgcaggc gccctggagg cgctggagac ggcggcggcc gccgccgaag   49080
aggcggatgc cgcgcgcggg gatgagccgg cgggtggggg cgacggggog gcgccccgg    49140 gtctggccgt cgcggagatg gaggtccaga tcgtgcgcaa cgacccgccg ctacgatacg   49200
acaccaacct ccccgtggat ctgctacata tggtgtacgc gggccgcggg gcgaccggct   49260
cgtcgggggt ggtgttcggg acctggtacc gcactatcca ggaccgcacc atcacggact   49320 ttccccctgac caccogcagt gccgactttc gggacggccg gatgtccaag accttcatga   49380
cggcgctggt cctgtccctg cagtcgtgcg gccggctgta tgtgggccag cgccactatt   49440
ccgccttcga gtgcgccgtg ttgtgtctct acctgctgta ccgaaacacg cacggggccg   49500
ccgacgatag cgaccgcgct ccggtcacgt tcggggatct gctgggccgg ctgccccgct   49560
acctggcgtg cctggccgcg gtgatcggga ccgagggcgg ccggccacag taccgctacc   49620
gcgacgacaa gctcccccaag acgcagttcg cggccggcgg gggccgctac gaacacggag   49680
cgctggcgtc gcacatcgtg atcgccacgc tgatgcacca cggggtgctc ccggcggccc   49740 cggggggacgt cccccgggac gcgagcaccc acgttaaccc cgacggcgtg cgcaccacg    49800 acgacataaa ccgcgccgcc gccgcgttcc tcagccgggg ccacaaccta ttcctgtggg   49860
aggaccagac tctgctgcgg gcaaccgcga acaccataac ggccctgggc gttatccagc   49920
ggctcctcgc gaacggcaac gtgtacgcgg accgcctcaa caaccgcctg cagctgggca   49980
tgctgatccc cggagccgtc ccttcggagg ccatcgcccg tggggcctcc gggtccgact   50040 cggggggccat caagagcgga gacaacaatc tggaggcgct atgtgccaat tacgtgcttc   50100
cgctgtaccg ggccgacccg gcggtcgagc tgacccagct gtttcccggc ctggccgccc   50160
tgtgtcttga cgcccaggcg gggcggccgg tcgggtcgac gcggcgggtg gtggatatgt   50220
catcgggggc ccgccaggcg gcgctggtgc gcctcaccgc cctggaactc atcaaccgca   50280
cccgcacaaa ccccacccc gtgggggagg ttatccacgc ccacgacgcc ctggcgatcc    50340
aatacgaaca ggggcttggc ctgctggcgc agcaggcacg cattggcttg ggctccaaca   50400
ccaagcgttt ctccgcgttc aacgttagca gcgactacga catgttgtac tttttatgtc   50460
tggggttcat tccacagtac ctgtcggcgg tttagtgggt ggtgggcgag ggggagggg    50520 gcattaggga gaaagaacaa gagcctccgt tgggtttct ttgtgcctgt actcaaaagg     50580
tcataccccg taaacggcgg gctccagtcc cggcccggcg gttggcgtga acgcaacggc   50640
gggagctggg ttagcgttta gtttagcatt cgctctcgcc tttccgcccg cccccgaccg   50700
ttgagccttt tttttttttcg tccaccaaag tctctgtggg tgcgcgcatg gcagccgatg   50760
ccccgggaga ccgatggag gagccctgc cagacagggc cgtgcccatt tacgtggctg       50820 ggttttggc cctgtatgac agcggggact cgggcgagtt ggcattggat ccggatacgg     50880
tgcgggcggc cctgcctccg gataacccac tcccgattaa cgtggaccac cgcgctggct   50940
gcgaggtggg gcgggtgctg gccgtggtcg acgaccccg cgggccgttt tttgtgggac     51000
tgatcgcctg cgtgcaactg gagcgcgtcc tcgagacggc cgccagcgct gcgattttcg   51060
agcgccgcgg gccgccgctc tcccggggagg agcgcctgtt gtacctgatc accaactacc   51120
tgccctcggt ctccctggcc acaaaacgcc tggggggcga ggcgcacccc gatcgcacgc    51180
tgttcgcgca cgtagcgctg tgcgcgatcg ggcggcgccct tggcactatc gtcacctacg   51240
acaccggtct cgacgccgcc atcgcgccct ttcgccacct gtcgccggcg tctcgcgagg   51300
```

-continued

```
gggcgcggcg actggccgcc gaggccgagc tcgcgctatc cggacgcacc tgggcgcccg   51360
gcgtggaggc gctgacccac acgctgcttt ccaccgccgt taacaacatg atgctgcggg   51420
accgctggag cctggtggcc gagcggcggc ggcaggccgg gatcgccgga cacacctacc   51480
tccaggcgag cgaaaaattc aaaatgtggg gggcggagcc tgtttccgcg ccggcgcgcg   51540
ggtataagaa cggggccccg gagtccacgg acataccgcc cggctcgatc gctgccgcgc   51600
cgcagggtga ccggtgccca atcgtccgtc agcgcgggt cgcctcgccc ccggtactgc   51660
cccccatgaa ccccgttcca acatcgggca ccccggcccc cgcgccgccc ggcgacggga   51720
gctacctgtg gatcccggcc tcccattaca accagctcgt cgccggccac gccgcgcccc   51780
aaccccagcc gcattccgcg tttggtttcc cggctgcggc gggggccgtg gcctatgggc   51840
ctcacggcgc gggtctttcc cagcattacc ctccccacgt cgcccatcag tatcccgggg   51900
tgctgttctc gggacccagc ccactcgagg cgcagatagc cgcgttggtg ggggccatag   51960
ccgcggaccg ccaggcgggc ggtcagccgg ccgcgggaga ccctgggtc cgggggtcgg   52020 gaaagcgtcg ccggtacgag gcggggccgt cggagtccta ctgcgaccag gacgaaccgg   52080
acgcggacta cccgtactac cccgggggagg ctcgaggcgg gccgcgcggg gtcgactctc   52140
ggcgcgcggc ccgccagtct cccgggacca acgagaccat cacggcgctg atgggggcgg   52200
tgacgtctct gcagcaggaa ctggcgcaca tgcgggctcg gaccagcgcc ccctatggaa   52260
tgtacacgcc ggtggcgcac tatcgccctc aggtggggga gccggaacca acaacgaccc   52320
acccggccct ttgtcccccg gaggccgtgt atcgcccccc accacacagc gcccctacg   52380 gtcctcccca gggtccggcg tcccatgccc ccactccccc gtatgcccca gctgcctgcc   52440
cgccaggccc gccaccgccc ccatgtcctt ccacccagac gcgcgccct ctaccgacgg   52500 agcccgcgtt cccccccgcc gccaccggat cccaaccgga ggcatccaac gcggaggccg   52560
gggcccttgt caacgccagc agcgcagcac acgtggacgt tgacacggcc cgcgccgccg   52620
atttgttcgt ctctcagatg atggggggccc gctgattcgc cccggtcttt ggtaccatgg   52680
gatgtcttac tgtatatctt tttaaataaa ccaggtaata ccaaataaga cccattggtg   52740
tatgttcttt ttttattggg aggggcgggt aggcgggtag ctttacaatg caaaagcctt   52800
tgacgtggag gaaggcgtgg gggggaggaa atcggcactg accaaggggg tccgtttttgt   52860 cacgggaaag gaaagaggaa acaggccgcg gacacccggg ggagtttatg tgttcctttt   52920
tctttcttcc cacacacaca caaaaggcgt accaaacaaa aaaaccaaaa gatgcgcatg   52980
cggtttaaca cccgtggttt ttatttacaa caaacccccc gtcacaggtc gtcctcgtcg   53040
gcgtcaccgt ctttgttggg aacttgggtg tagttggtgt tgcggcgctt gcgcatgacc   53100
atgtcggtga ccttggcgct gagcagcgcg ctcgtgccct tcttcttggc cttgtgttcc   53160
gtgcgctcca tggccgacac cagggccatg taccgtatca tctccctggc ctcggctagc   53220
ttggcctcgt caaagtcgcc gccctcctcg ccctccccgg acgcgtccgg gttggtgggg   53280
ttcttgagct ccttggtggt tagagggtac agggccttca tggggttgct ctgcagccgc   53340
atgacgtaac gaaaggcgaa gaaggccgcc gccaggccgg ccaggaccaa cagacccacg   53400
gccagcgccc caaagggggtt ggacatgaag aggacacgc ccgacacggc cgataccacg   53460
ccgcccacga tgcccatcac caccttgccg accgcgcgcc ccaggtcgcc catcccctcg   53520
aagaacgcgc ccaggcccgc gaacatggcg gcgttggcgt cggcgtggat gaccgtgtcg   53580
atgtcggcga agcgcaggtc gtgcagctgg ttgcggcgct ggacctccgt gtagtccagc   53640
aggccgctgt ccttgatctc gtggcgggtg tacacctcca gggggacaaa ctcgtgatcc   53700
```

```
tccagcatgg tgatgttgag gtcgatgaag gtgctgacgg tggtgatgtc ggcgcggctc   53760
agctggtggg agtacgcgta ctcctcgaag tacacgtagc ccccaccgaa ggtgaagtag   53820
cgccggtgtc ccacggtgca cggctcgatc gcatcgcgcg tcagccgcag ctcgttgttc   53880
tcccccagct gcccctcgac caacgggccc tggtcttcgt accgaaagct gaccaggggg   53940
cggctgtagc aggccccggg ccgcgagctg atgcgcatcg agttttggac gatcacgttg   54000
tccgcggcga ccggcacgca cgtggagacg gccatcacgt cgccgagcat ccgcgcgctc   54060
acccgccggc ccacggtgac cgaggcgatg gcgttggggt tcagcttgcg ggcctcgttc   54120
cacagggtca gctcgtgatt ctgtagctcg caccacgcga tggcaacgcg gcccaacata   54180
tcgttgacat ggcgctgtat gtggttgtac gtaaactgca gccgggcgaa ctcgatggag   54240
gaggtggtct tgatgcgctc cacggacgcg ttggcgctgg ccccgggcgg cggggggcgtg  54300 gggtttgggg gcttgcggct ctgctctcgg aggtgttccc gcacgtacag ctccgcgagc   54360
gtgttgctga gaaggggctg gtacgcgatc agaaagcccc cattggccag gtagtactgc   54420
ggctggccca ccttgatgtg cgtcgcgttg tacctgcggg cgaagatgcg gtccatggcg   54480
tcgcgggcgt ccttgccgat gcagtccccc aggtccacgc gcgagagcgg gtactcggtc   54540
aggttggtgg tgaaggtggt ggatatggcg tcggaggaga atcggaagga gccgccgtac   54600
tcggagcgca gcatctcgtc cacttcctgc cacttggtca tggtgcagac cgacgggcgc   54660
tttggcaccc agtcccaggc cacggtgaac ttgggggtcg tgagcaggtt ccgggtggtc   54720
ggcgccgtgg cccgggcctt ggtggtgagg tcgcgcgcgt agaagccgtc gacctgcttg   54780
aagcggtcgg cggcgtagct ggtgtgttcg gtgtgcgacc cctcccggta gccgtaaaac   54840
ggggacatgt acacaaagtc gccagtcgcc agcacaaact cgtcgtacgg gtacaccgag   54900
cgcgcgtcca cctcctcgac gatgcagttt accgtcgtcc cgtaccggtg gaacgcctcc   54960
acccgcgagg ggttgtactt gaggtcggtg gtgtgccagc cccggctcgt gcgggtcgcg   55020
gcgttggccg gtttcagctc catgtcggtc tcgtggtcgt cccggtgaaa cgcggtggtc   55080
tccaggttgt tgcgcacgta cttggccgtg gaccgacaga ccccccttggc gttgatcttg   55140 tcgatcacct cctcgaaggg gacggggggcg cggtcctcaa agatccccat aaactgggag   55200
tagcggtggc cgaaccacac ctgcgaaacg gtgacgtctt tgtagtacat ggtggccttg   55260
aacttgtacg gggcgatgtt ctccttgaag accaccgcga tgccctccgt gtagttctga   55320
ccctcgggcc gggtcgggca gcggcgcggc tgctcgaact gcaccaccgt ggcgcccgtg   55380
gggggtgggc acacgtaaaa gtttgcatcg gtgttctccg ccttgatgtc ccgcaggtgc   55440
tcgcgcaggg tggcgtggcc cgcggcgacg gtcgcgttgt cgccggcggg gcgtggtggc   55500
gttgggtttt tcggtttttt gttcttcttc ggtttcgggt ccccgttgg ggcggcgcca   55560 agggcgggcg gcgccggagt ggcagggccc ccgttcgccg cctgggtcgc ggccgcgacc   55620
ccaggcgtgc cgggggaact cggagccgcc gacgccacca ggacccccag cgtcaacccc   55680
aagagcgccc atacgacgaa ccaccggcgc ccccacgagg gggcgccctg gtgcatggcg   55740
ggactacggg ggcccgtcgt gcccccgtc aggtagcctg ggggcgaggt gctggaggac   55800
cgagtagagg atcgagaaaa cgtcgcggtc gtagaccacg accgaccggg ggccgataca   55860
gccgtcgggg gcgctctcga cgatggccac cagcggacag tcggagtcgt acgtgagata   55920
tacgccgggc gggtaacggt aacgaccttc ggaggtcggg cggctgcagt ccgggcggcg   55980
caactcgagc tccccgcacc ggtagaccga ggcaaagagt gtggtggcga taatcagctc   56040
```

-continued

```
gcgaatatat cgccaggcgg cgcgctgagt gggcgttatt ccggaaatgc cgtcaaaaca   56100
gtaaaacctc tgaaattcgc tgacggccca atcagcaccc gagcccccg cccccatgat     56160 gaaccgggcg agctcctcct tcaggtgcgg caggagcccc acgttctcga cgctgtaata    56220
cagcgcggtg ttgggggct gggcgaagct gtgggtggag tgatcaaaga ggggcccgtt     56280
gacgagctcg aagaagcgat gggtgatgct ggggagcagg gccgggtcca cctggtgtcg    56340
caggagagac gctcgcatga accggtgcgc gtcgaacacg cccggcgccg agcggttgtc    56400
gatgaccgtg cccgcgcccg ccgtcagggc gcagaagcgc gcgcgcgccg caaagccgtt    56460
ggcgaccgcg cgcaacgtcg cgggcagcac ctcgccgtgg acgctgaccc gcagcatctt    56520
ctcgagctcc ccgcgctgct cgcggacgca gcgccccagg ctggccaacg accgcttcgt    56580
caggcggtcc gcgtacagcc gccgtcgctc ccgtacgtcc gcggccgctt gcgtggcgat    56640
gtccccccac gtctcgggcc cctgcccccc gggcccgcgg cgacggtctt cgtcctcgcc    56700
cccgcccccg ggagctccca accccgtgc cccttcctct acggcgacac ggtccccgtc     56760
gtcgtcgggg cccgcgccgc ccttgggcgc gtccgccgcg ccccccgccc ccatgcgcgc    56820
cagcacgcga cgcagcgcct cctcgtcgca ctgttcgggg ctgacgaggc gccgcaagag    56880
cggcgtcgtc aggtggtggt cgtagcacgc gcggatgagc gcctcgatct gatcgtcggg    56940
tgacgtggcc tgaccgccga ttattagggc gtccaccata tccagcgccg ccaggtggct    57000
cccgaacgcg cgatcgaaat gctccgcccg ccgcccgaac agcgccagtt ccacggccac    57060
cgcggcggtc tcctgctgca actcgcgccg cgccagcgcg gtcaggttgc tggcaaacgc    57120
gtccatggtg gtctggccgg cgcggtcgcc ggacgcgagc cagaatcgca attcgctgat    57180
ggcgtacagg ccgggcgtgg tggcctgaaa cacgtcgtgc gcctccagca gggcgtcggc    57240 ctccttgcg accgagtcgt tctcgggcga cgggtggggc tgcccgtcgc cccccgcggt     57300
ccgggccagc gcatggtcca acacggagag cgcccgcgcg cggtcggcgt ccgacagccc    57360
ggcggcgtgg ggcaggtacc gccgcagctc gttggcgtcc agccgcacct gcgcctgctg    57420
ggtgacgtgg ttacagatac ggtccgccag gcggcgggcg atcgtcgccc cctggttcgc    57480
cgtcacacac agttcctcga aacagaccgc gcaggggtgg gacgggtcgc taagctccgg    57540
ggggacgata aggcccgacc ccaccgcccc caccataaac tcccgaacgc gctccagcgc    57600
ggcggtggcg ccgcgcgagg gggtgatgag gtggcagtag tttagctgct ttagaaagtt    57660
ctcgacgtcg tgcaggaaac acagctccat atggacggtc ccgccatacg tatccagcct    57720
gacccgttgg tgatacggac agggtcgggc caggcccatg gtctcggtga aaaacgccgc    57780
gacgtctccc gcggtcgcga acgtctccag gctgcccagg agccgctcgc cctcgcgcca    57840
cgcgtactct agcagcaact ccagggtgac cgacagcggg gtgagaaagg ccccggcctg    57900
ggcctccagg cccggcctca gacgacgccg cagcgcccgc acctgaagcg cgttcagctt    57960 cagttgggg agcttccccc gtccgatgtg ggggtcgcac cgccggagca gctctatctg     58020
aaacacatag gtctgcacct gcccgagcag ggctaacaac ttttgacggg ccacggtggg    58080
ctcggacacc ggggcggcca tctcgcggcg ccgatctgta ccgcggccgg agtatgcggt    58140
ggaccgaggc ggtccgtacg ctacccggtg tctggctgag ccccgggtc cccctcttcg     58200 gggcggcctc ccgcgggccc gccgaccggc aagccgggag tcggcggcgc gtgcgtttct    58260
gttctattcc cagacaccgc ggagaggaat cacggcccgc ccagagatat agacacggaa    58320
cacaaacaag cacggatgtc gtagcaataa tttattttac acacattccc cgcccgccc     58380 taggttcccc caccccccaa cccctcacag catatccaac gtcaggtctc ccttttttgtc    58440
```

-continued

```
ggggggcccc tccccaaacg ggtcatcccc gtggaacgcc cgtttgcggc cggcaaatgc 58500
cggtcccggg gccccggggc cgccgaacgg cgtcgcgttg tcgtcctcgc agccaaaatc 58560
cccaaagtta aacacctccc cggcgttgcc gagttggctg actagggcct cggcctcgtg 58620
cgccacctcc agggccgcgt ccgtcgacca ctcgccgttg ccgcgctcca gggcacgcgc 58680
ggtcagctcc atcatctcct cgcttaggta ctcgtcctcc aggagcgcca gccagtcctc 58740
gatctgcagc tgctgggtgc ggggccccag gcttttcacg gtcgccacga acacgctact 58800
ggcgacggcc gccccgccct cggagataat gccccggagc tgctcgcaca gcgagctttc 58860
gtgcgctccg ccgccgaggt tcgaggccgc gcacacaaac ccggcccggg gacaggccag 58920
gacgaacttg cgggtgcggt caaaaataag gagcgggcac gcgtttttgc cgcccatcag 58980
gctggcccag ttcccggcct gaaacacacg gtcgttgccg gccatgccgt agtatttgct 59040
gatgctcaac cccaacacga ccatggggcg cgccgccatg acgggccgca gcaggttgca 59100
gctggcgaac atggacgtcc acgcgcccgg atgcgcgtcc acggcgtcca tcagcgcgcg 59160
ggccccggcc tccaggcccg ccccgccctg cgcggaccac gcggccgccg cctgcacgct 59220
ggggggacgg cgggaccccg cgatgatggc cgtgagggtg ttgatgaagt atgtcgagtg 59280
atcgcagtac cgcagaatct ggtttgccat gtagtacatc gccagctcgc tcacgttgtt 59340 ggggccagg ttaataaagt ttatcgcgcc gtagtccagg gaaaactttt taatgaacgc 59400
gatggtctcg atgtcctcgc gcgacaggag ccgggcggga agctggttgc gttggagggc 59460
cgtccagaac cactgcgggt tcggctggtt ggaccccggg ggcttgccgt tggggaagat 59520
ggccgcgtgg aactgcttca gcagaaagcc cagcggtccg aggaggatgt ccacgcgctt 59580
gtcgggcttc tggtaggcgc tctggaggct ggcgacccgc gccttggcgg cctcggacgc 59640
gttggcgctc gcgcccgcga acaacacgcg gctcttgacg cgcagctcct tgggaaaccc 59700
cagggtcacg cgggcaacgt cgccctcgaa gctgctctcg gcggggggcc tctggccggc 59760
cgttaggctg ggggcgcaga tagccgcccc ctccgagagc gcgaccgtca gcgttttggc 59820
cgacagaaac ccgttgttaa acatgtccat cacgcgccgc cgcagcaccg gttggaattg 59880
attgcgaaag ttgcgcccct cgaccgactg cccggcgaac accccgtggc actggctcag 59940
ggccaggtcc tgatacacgg cgaggttgga tcgccgcccg agaagctgaa gcaggggggca 60000 tggcccgcac gcgtacgggt ccagcgtcag ggacatggcg tggttggcct cgcccagacc 60060
gtcgcgaaac ttgaagttcc tcccctccac caggttgcgc atcagctgct ccacctcgcg 60120
gtccacgacc tgcctgacgt tgttcaccac cgtatgcagg gcctcgcggt tggtgatgat 60180
ggtctccagc cgccccatgg ccgtggggac cgcctggtcc acgtactgca gggtctcgag 60240
ttcggccatg acgcgctcgg tcgccgcgcg gtacgtctcc tgcatgatgg tccgggcggt 60300
ctcggatccg tccgcgcgct tcagggccga gaaggcggcg tagtttccca gcacgtcgca 60360
gtcgctgtac atgctgttca tggtcccgaa gacgccgatg gctccgcggg cggcgctggc 60420
gaacttggga tggcgcgccc ggaggcgcat gagcgtcgtg tgtacgcagg cgtggcgcgt 60480
gtcgaaggtg cacaggttgc agggcacgtc ggtctggttg gagtccgcga cgtatcgaaa 60540
cacgtccatc tcctggcgcc cgacgatcac gccgccgtcg cagcgctcca ggtaaaacag 60600
catcttggcc agcagcgccg gggaaaaccc acacagcatg gccaggtgct cgccggcaaa 60660
ttcctgggtt ccgccgacga ggggcgcggt gggccgaccc tcgaacccgg gcaccacgtg 60720
tccctcgcgg tccacctgtg ggttggccgc cacgtgggtc ccgggcacga ggaagaagcg 60780
```

-continued

```
gtaaaaggag ggtttgctgt ggtcctttgg gtccgccgga ccggcgtcgt ccacctcggt   60840
gagatggagg gccgagttgg tgctaaatac catggccccc acgagtcccg cggcgcgcgc   60900
caggtacgcc ccgacggcgt tggcgcgggc cgcggccgtg tcctggccct cgcacagcgg   60960
ccacgcggag atgtcggtgg gcggctcgtc gaagacggcc atcgacacga tagactcgag   61020
ggccagggcg gcgtctccgg ccatgacgga ggccaggcgc tgttcgaacc cgcccgccgg   61080
gcccttgccg ccgccgtcgc gcccaccccg cggggtctta ccctggctgg cttcgaaggc   61140
cgtgaacgta atgtcggcgg ggagggcggc gccctcgtgg ttttcgtcaa acgccaggtg   61200
ggcggccgcg cgggccacgg cgtccacgtt tcggcatcgc agtgccacgg cggcgggtcc   61260
cacgaccgcc tcgaacagga ggcggttgag ggggcggtta aaaaacggaa gcgggtaggt   61320
aaaattctcc ccgatcgatc ggtggttggc gttgaacggc tcggcgatga cccggctaaa   61380
atccggcatg aacagctgca acggatacac gggtatgcgg tgcacctccg ccccgcctat   61440
ggttaccttg tccgagcctc ccaggtgcag aaaggtgttg ttgatgcaca cggcctcctt   61500
gaagccctcg gtaacgacca gatacaggag ggcgcggtcc gggtccaggc cgaggcgctc   61560
acacagcgcc tcccccgtcg tctcgtgttt gaggtcgccg ggccgggggg tgtagtccga   61620
aaagccaaaa tggcggcgtg cccgctcgca gagtcgcgtc aggtttgggg cctgggtgct   61680
ggggtccagg tgccggccgc cgtgaaagac gtacacggac gagctgtagt gcgatggcgt   61740
cagtttcagg gacaccgcgg taccccgag ccccgtcgtg cgagaaccca cgaccacggc   61800
tacgttggcc tcaaagccgc tctccacggt caggcccacg accaggggcg ccacggcgac   61860
gtcggcatcg ccgctgcgcg ccgacagtaa cgccagaagc tcgatgcctt cggacggaca   61920
cgcgcgagcg tacacgtatc ccaggggccc ggggggggacc ttgatggtgg ttgccgtctt   61980
gggctttgtc tccatgtcct cctggcaatc ggtccgcaaa cggaggtaat cccggcacga   62040
cgacggacgc ccgacgaggt atgtctcccg agcgtcaaaa tccggggggg ggggcggcga   62100
cggtcaaggg gagggtggga daccgggggtt ggggaatgaa tccctaccct tcacagacaa   62160
cccccgggta accacggggt gccgatgaac cccggcggct ggcaacgcgg ggtccctgcg   62220
agaggcacag atgcttacgg tcaggtgctc cgggccgggt gcgtctgata tgcggttggt   62280
atatgtacac tttacctggg ggcgtgccgg accgccccag cccctccac acccgcgcg    62340 tcatcagccg gtgggcgtgg ccgctattat aaaaaaagtg agaacgcgaa gcgttcgcac   62400
tttgtcctaa taatatatat attattagga caaagtgcga acgcttcgcg ttctcacttt   62460
ttttataata gcggccacgc ccaccggcta cgtcacgctc ctgtcggccg ccggcggtcc   62520
ataagcccgg ccggccgggc cgacgcgaat aaaccgggcc gccggccggg gcgccgcgca   62580
gcagctcgcc gcccggatcc gccagacaaa caaggccctt gcacatgccg gcccgggcga   62640
gcctgggggt ccggtaattt tgccatccca cccaagcggc ttttggggtt tttcctcttc   62700 cccctcccc acatccccc tctttagggg ttcgggtggg aacaaccgcg atgttttccg     62760
gtggcggcgg cccgctgtcc cccggaggaa agtcggcggc cagggcggcg tccgggtttt   62820
ttgcgcccgc cggccctcgc ggagccggcc ggggaccccc gccttgtttg aggcaaaact   62880
tttacaaccc ctacctcgcc ccagtcggga cgcaacagaa gccgaccggg ccaacccagc   62940
gccatacgta ctatagcgaa tgcgatgaat ttcgattcat cgccccgcgg gtgctggacg   63000
aggatgcccc cccggagaag cgcgccgggg tgcacgacgg tcacctcaag cgcgcccca    63060 aggtgtactg cggggggggac gagcgcgacg tcctccgcgt cgggtcgggc ggcttctggc   63120
cgcggcgctc gcgcctgtgg ggcggcgtgg accacgcccc ggcgggggttc aaccccaccg   63180
```

-continued

```
tcaccgtctt tcacgtgtac gacatcctgg agaacgtgga gcacgcgtac ggcatgcgcg    63240
cggcccagtt ccacgcgcgg tttatggacg ccatcacacc gacggggacc gtcatcacgc    63300
tcctgggcct gactccggaa ggccaccggg tggccgttca cgtttacggc acgcggcagt    63360 actttacat gaacaaggag gaggttgaca ggcacctaca atgccgcgcc ccacgagatc    63420
tctgcgagcg catggccgcg gccctgcgcg agtccccggg cgcgtcgttc cgcggcatct    63480
ccgcggacca cttcgaggcg gaggtggtgg agcgcaccga cgtgtactac tacgagacgc    63540
gccccgctct gttttaccgc gtctacgtcc gaagcgggcg cgtgctgtcg tacctgtgcg    63600
acaacttctg cccggccatc aagaagtacg agggtggggt cgacgccacc acccggttca    63660
tcctggacaa ccccgggttc gtcaccttcg gctggtaccg tctcaaaccg ggccggaaca    63720
acacgctagc ccagccgcgg gccccgatgg ccttcgggac atccagcgac gtcgagttta    63780
actgtacggc ggacaacctg gccatcgagg ggggcatgag cgacctaccg gcatacaagc    63840
tcatgtgctt cgatatcgaa tgcaaggcgg ggggggagga cgagctggcc tttccggtgg    63900
ccgggcaccc ggaggacctg gttattcaga tatcctgtct gctctacgac ctgtccacca    63960
ccgccctgga gcacgtcctc ctgttttcgc tcggttcctg cgacctcccc gaatcccacc    64020
tgaacgagct ggcggccagg ggcctgccca cgcccgtggt tctggaattc gacagcgaat    64080
tcgagatgct gttggccttc atgacccttg tgaaacagta cggccccgag ttcgtgaccg    64140
ggtacaacat catcaacttc gactggccct tcttgctggc caagctgacg gacatttaca    64200 aggtcccccct ggacgggtac ggccgcatga acggccgggg cgtgtttcgc gtgtgggaca    64260
taggccagag ccacttccag aagcgcagca agataaaggt gaacggcatg gtgaacatcg    64320
acatgtacgg gatcataacc gacaagatca agctctcgag ctacaagctc aacgccgtgg    64380
ccgaagccgt cctgaaggac aagaagaagg acctgagcta tcgcgacatc cccgcctact    64440
acgccaccgg gcccgcgcaa cgcggggtga tcggcgagta ctgcatacag gattccctgc    64500
tggtgggcca gctgtttttt aagttttttgc cccatctgga gctctcggcc gtcgcgcgct    64560
tggcgggtat taacatcacc cgcaccatct acgacggcca gcagatccgc gtctttacgt    64620
gcctgctgcg cctggccgac cagaagggct ttattctgcc ggacacccag gggcgattta    64680
ggggcgccgg ggggggaggcg cccaagcgtc cggccgcagc ccgggaggac gaggagcggc    64740
cagaggagga gggggaggac gaggacgaac gcgaggaggg cggggggcgag cgggagccgg    64800 agggcgcgcg ggagaccgcc ggccggcacg tggggtacca gggggccagg gtccttgacc    64860
ccacttccgg gtttcacgtg aaccccgtgg tggtgttcga ctttgccagc ctgtaccccca    64920 gcatcatcca ggcccacaac ctgtgcttca gcacgctctc cctgagggcc gacgcagtgg    64980
cgcacctgga ggcgggcaag gactacctgg agatcgaggt ggggggggcga cggctgttct    65040 tcgtcaaggc tcacgtgcga gagagcctcc tcagcatcct cctgcgggac tggctcgcca    65100
tgcgaaagca gatccgctcg cggattcccc agagcagccc cgaggaggcc gtgctcctgg    65160
acaagcagca ggccgccatc aaggtcgtgt gtaactcggt gtacgggttc acgggagtgc    65220
agcacggact cctgcccgtgc ctgcacgttg ccgcgacggt gacgaccatc ggccgcgaga    65280
tgctgctcgc gacccgcgag tacgtccacg cgcgctgggc ggccttcgaa cagctcctgg    65340
ccgatttccc ggaggcggcc gacatgcgcg cccccgggcc ctattccatg cgcatcatct    65400
acggggacac ggactccata tttgtgctgt gccgcgcgcct cacggccgcc gggctgacgg    65460
ccatgggcga caagatggcg agccacatct cgcgcgcgct gtttctgccc cccatcaaac    65520
```

```
tcgagtgcga aaagacgttc accaagctgc tgctgatcgc caagaaaaag tacatcggcg      65580
tcatctacgg gggtaagatg ctcatcaagg gcgtggatct ggtgcgcaaa aacaactgcg      65640
cgtttatcaa ccgcacctcc agggccctgg tcgacctgct gttttacgac gataccgtat      65700
ccggagcggc cgccgcgtta gccgagcgcc ccgcagagga gtggctggcg cgacccctgc      65760
ccgagggact gcaggcgttc ggggccgtcc tcgtagacgc ccatcggcgc atcaccgacc      65820
cggagaggga catccaggac tttgtcctca ccgccgaact gagcagacac ccgcgcgcgt      65880
acaccaacaa gcgcctggcc cacctgacgg tgtattacaa gctcatggcc cgccgcgcgc      65940
aggtcccgtc catcaaggac cggatcccgt acgtgatcgt ggcccagacc cgcgaggtag      66000
aggagacggt cgcgcggctg gccgccctcc gcgagctaga cgccgccgcc ccaggggacg      66060
agcccgcccc ccccgcggcc ctgccctccc cggccaagcg ccccccgggag acgccgtcgc      66120 atgccgaccc cccgggaggc gcgtccaagc cccgcaagct gctggtgtcc gagctggccg      66180
aggatcccgc atacgccatt gcccacggcg tcgccctgaa cacggactat tacttctccc      66240
acctgttggg ggcggcgtgc gtgacattca aggccctgtt tgggaataac gccaagatca      66300
ccgagagtct gttaaaaagg tttattcccg aagtgtggca ccccccggac gacgtggccg      66360
cgcggctccg ggccgcaggg ttcggggcgg tgggtgccgg cgctacggcg gaggaaactc      66420
gtcgaatgtt gcatagagcc tttgatactc tagcatgagc cccccgtcga agctgatgtc      66480
cctcatttta caataaatgt ctgcggccga cacggtcgga atctccgcgt ccgtgggttt      66540
ctctgcgttg cgccggacca cgagcacaaa cgtgctctgc cacacgtggg cgacgaaccg      66600
gtaccccggg cacgcggtga gcatccggtc tatgagccgg tagtgcaggt gggcggacgt      66660
gccgggaaag atgacgtaca gcatgtggcc cccgtaagtg gggtccgggt aaaacaacag      66720
ccgcgggtcg cacgccccgc ctccgcgcag gatcgtgtgg acgaaaaaaa gctcgggttg      66780
gccaagaatc ccggccaaga ggtcctggag gggggcgttg tggcggtcgg ccaacacgac      66840
caaggaggcc aggaaggcgc gatgctcgaa tatcgtgttg atctgctgca cgaaggccag      66900
gattagggcc tcgcggctgg tggcggcgaa ccgcccgtct cccgcgttgc acgcgggaca      66960
gcaacccccg atgcctaggt agtagcccat cccggagagg gtcaggcagt tgtcggccac      67020
ggtctggtcc agacagaagg gcagcgacac gggagtggtc ttcaccaggg gcaccgagaa      67080
cgagcgcacg atggcgatct cctcggaggg cgtctgggcg agggcggcga aaaggccccg      67140
atagcgctgg cgctcgtgta aacacagctc ctgtttgcgg gcgtgaggcg gcaggctctt      67200
ccgggaggcc cgacgcacca cgcccagagt cccgccggcc gcagaggagc acgaccgccg      67260
gcgctccttg ccgtgatagg gcccgggccg ggagccgcgg cgatgggggt cggtatcata      67320
cataggtaca cagggtgtgc tccagggaca ggagcgagat cgagtggcgt ctaagcagcg      67380
cgcccgcctc acggacaaat gtggcgagcg cggtgggctt tggtacaaat acctgatacg      67440
tcttgaaggt gtagatgagg gcacgcaacg ctatgcagac acgcccctcg aactcgttcc      67500
cgcaggccag cttggccttg tggagcagca gctcgtcggg atgggtggcg gggggatggc      67560
cgaacagaac ccaggggtca acctccatct ccgtgatggc gcacatgggg tcacagaaca      67620
tgtgcttaaa gatggcctcg gccccgcgcg cccgcagcag gctcacaaac cggccccgt        67680 ccccgggctg cgtctcgggg tccgcctcga gctggtcgac gacgggtacg atacagtcga      67740
agaggctcgt gttgttttcc gagtagcgga ccacggaggc ccggagtctg cgcagggcca      67800
gccagtaagc ccgcaccagt aacaggttac acagcaggca ttctccgccg gtgcgcccgc      67860
gcccccggcc gtgtttcagc acggtggcca tcagagggcc caggtcgagg tcgggctggg      67920
```

```
catcgggttc ggtaaactgc gcaaagcgcg gagccacgtc gcgcgtgcgt gccccgcgat   67980
gcgcttccca ggactggcgg accgtggcgc gacgggcctc cgcggcagcg cgcagctggg   68040
gccccgactc ccagacggcg ggggtgccgg cgaggagcag caggaccaga tccgcgtacg   68100
cccacgtatc cggcgactcc tccggctcgc ggtccccggc gaccgtctcg aattccccgt   68160
tgcgagcggc ggcgcgcgta cagcagctgt ccccgccccc gcgccgaccc tccgtgcagt   68220
ccaggagacg ggcgcaatcc ttccagttca tcagcgcggt ggtgagcgac ggctgcgtgc   68280
cggatcccgc cgccgacccc gcccctcct cgcccccgga ggccaaggtt ccgatgaggg    68340
cccgggtggc agactgcgcc aggaacgagt agttggagta ctgcaccttg gcggctcccg   68400
gggagggcga gggcttgggt tgcttctggg catgccgccc gggcaccccg ccgtcggtac   68460
ggaagcagca gtggagaaaa aagtgccggt ggatgtcgtt tatggtgagg gcaaagcgtg   68520
cgaaggagcc gaccagggtc gccttcttgg tgcgcagaaa gtggcggtcc atgacgtaca   68580
caaactcgaa cgcggccacg aagatgctag cggcgcagtg gggcgccccc aggcatttgg   68640
cacagagaaa cgcgtaatcg gccacccact ggggcgagag gcggtaggtt tgcttgtaca   68700
gctcgatggt gcggcagacc agacagggcc ggtccagcgc gaaggtgtcg atggccgccg   68760
cggaaaaggg cccggtgtcc aaaagcccct ccccacaggg atccgggggc gggttgcggg   68820
gtcctccgcg cccgcccgaa ccccctccgt cgcccgcccc cccgcgggcc cttgaggggg   68880
cggtgaccac gtcggcggcg acgtcctcgt cgagcgtacc gacgggcggc acacctatca   68940
cgtgactggc cgccaggagc tcggcgcaga gagcctcgtt aagagccagg aggctgggat   69000
cgaaggccac atacgcgcgc tcgaacgccc ccgccttcca gctgctgccg ggggactctt   69060
cgcacaccgc gacgctcgcc aggaccccgg ggggcgaagt tgccatggct gggcgggagg   69120
ggcgcacgcg ccagcgaact ttacgggaca caatccccga ctgcgcgctg cggtcccaga   69180
ccctggagag tctagacgcg cgctacgtct cgcgagacgg cgcgcatgac gcggccgtct   69240
ggttcgagga tatgaccccc gccgagctgg aggttgtctt cccgactacg gacgccaagc   69300
tgaactacct gtcgcggacg cagcggctgg cctccctcct gacgtacgcc gggcctataa   69360
aagcgcccga cgacgccgcc gccccgcaga ccccggacac cgcgtgtgtg cacggcgagc   69420
tgctcgcccg caagcgggaa agattcgcgg cggtcattaa ccggttcctg gacctgcacc   69480
agattctgcg gggctgacgc gcgcgctgtt gggcgggacg gttcgcgaac cctttggtgg   69540
gtttacgcgg gcacgcacgc tcccatcgcg ggcgccatgg cgggactggg caagccctac   69600 cccgccacc caggtgacgc cttcgagggt ctcgttcagc gaattcggct tatcgtccca    69660
tctacgttgc ggggcgggga cggggaggcg ggcccctact ctccctccag cctcccctcc   69720
aggtgcgcct ttcagtttca tggccatgac gggtccgacg agtcgtttcc catcgagtat   69780
gtactgcggc ttatgaacga ctgggccgag gtcccgtgca acccttacct gcgcatacag   69840
aacaccggcg tgtcggtgct gtttcagggg tttttttcatc gcccacacaa cgcccccggg   69900
ggcgcgatta cgccagagcg gaccaatgtg atcctgggct ccaccgagac gacggggctg   69960
tccctcggcg acctggacac catcaagggg cggctcggcc tggatgcccg gccgatgatg   70020
gccagcatgt ggatcagctg ctttgtgcgc atgccccgcg tgcagctcgc gtttcggttc   70080
atgggccccg aagatgccgg acggacgaga cggatcctgt gccgcgccgc cgagcaggct   70140
attacccgtc gccgccgaac ccggcggtcc cgggaggcgt acggggccga ggccgggctg   70200
ggggtggctg gaacgggttt ccgggccagg ggggacggtt ttggcccgct ccccttgtta   70260
```

```
acccaagggc cctcccgccc gtggcaccag gccctgcggg gtcttaagca cctacggatt   70320 ggccccccccg cgctcgtttt ggcggcggga ctcgtcctgg gggccgctat ttggtgggtg   70380
gttggtgctg gcgcgcgcct ataaaaaagg acgcaccgcc gccctaatcg ccagtgcgtt   70440
ccggacgcct tcgcccaca cagccctccc gtccgacacc cccatatcgc ttcccgacct   70500
ccggtcccga tggccgtccc gcaatttcac cgccccagca ccgttaccac cgatagcgtc   70560
cgggcgcttg gcatgcgcgg gctcgtcttg gccaccaata actctcagtt tatcatggat   70620
aacaaccacc cgcacccca gggcacccaa ggggccgtgc gggagtttct ccgcggtcag   70680
gcggcggcgc tgacggacct tggtctggcc cacgcaaaca acacgtttac cccgcagcct   70740
atgttcgcgg gcgacgcccc ggccgcctgg ttgcggcccg cgtttggcct gcggcgcacc   70800
tattcaccgt ttgtcgttcg agaaccttcg acgcccggga ccccgtgagg cccgggagt   70860 tccttctggg gtgtttta caataaaaga ccacaccaac gcacgagcct tgcgtttaat   70920
gtcgtgttta ttcaagggag tgggataggg ttcgacggtt cgaaacttaa cacacaaaat   70980
aatcgagcgc gtctagccca gtaacatgcg cacgtgatgt aggctggtca gcacggcgtc   71040
gctgtgatga agcagcgccc ggcgggtccg ctgtaactgc tgttgtaggc ggtaacaggc   71100
gcggatcagc accgccaggg cgctacgacc ggtgcgttgc acgtagcgtc gcgacagaac   71160
tgcgtttgcc gatacgggcg gggggccgaa ttgtaagcgc gtcacctctt gggagtcatc   71220
ggcggataac gcactgaatg gttcgttggt tatggggag tgtggttccc gagggagtgg   71280
gtcgagcgcc tcggcctcgg aatccgagag gaacaacgag gtggtgtcgg agtcttcgtc   71340
gtcagagaca tacagggtct gaagcagcga cacgggcggg ggggtagcgt caatgtgtag   71400
cgcgagggag gatgcccacg aagacacccc agacaaggag ctgcccgtgc gtggatttgt   71460
ggacgacgcg gaagccggga cggatgggcg gttttgcggt gcccggaacc gaaccgccgg   71520
atactccccg ggtgctacat gcccgttttg gggctggggt tggggctggg gctggggttg   71580
gggttggggc tggggttggg gctggggttg gggctggggt tggggttggg gttggggctg   71640
gggttggggt tggggctggg gctggggctg gggctggggc tggggctggg gctggggctg   71700
gggctggggc tggggctggg gctggggctg gggctgggggt tggggctggg gttggggctg   71760
gggcgcggac aggcggttga cggtcaaatg ccccgggggg cgcgcagatg tggtgggcgt   71820
ggccaccggc tgccgtgtag tggggcgcg ggaaaccggg cctccggcg taacaccgcc   71880 ctccagcgtc aagtatgtgg ggggcgggcc tgacgtcggg ggcgggtga cgggttggac   71940 cgcgggaggc ggggggagagg gacctgcggg agaggatgag gtcggctcgg ccgggttgcg   72000
gcctaaaaca gggggccgtgg ggtcggcggg gtcccagggt gaagggaggg attcccgcga   72060
ttcggacagc gacgcgacag cggggcgcgt aaggcgccgc tgcggcccgc ctacgggaac   72120
cctggggggg gttggcgcgg gacccgaggt tagcggggggg cggcggtttt cgcccccggg   72180
caaaaccgtg ccggttgcga ccggggggcgg aacgggatcg ataggagag cgggagaagc   72240 ctggccggcg aactggggac cgagcgggag gggcacacca gacaccaaag cgtggagcgc   72300
tggctctggg ggtttgggag gggccggggg gcgcgcgaaa tcggtaaccg gggcgaccgt   72360 gtcgggggagg gcaggcggcc gccaaccctg ggtggtcgcg gaagcctggg tggcgcgcgc   72420
cagggagcgt gcccggcggt gtcggcgcgc gcgcgacccg gacgaagaag cggcagaagc   72480
gcgggaggag gcggggggggc gggggggcggt ggcatcgggg ggcgccgggg aactttgggg   72540
ggacggcaag cgccggaagt cgtcgcgggg gcccacgggc gccggccgcg tgctttcggc   72600
cgggacgccc ggtcgtgctt cgcgagccgt gactgccggc ccaggggggcc gcggtgcaca   72660
```

-continued

```
ctgggacgtg gggacggact gatcggcggt gggcgaaagg gggtccgggg caaggagggg   72720
cgcggggccg ccggagtcgt cagacgcgag ctcctccagg ccgtgaatcc atgcccacat   72780 gcgaggggg  acgggctcgc cgggggtggc gtcggtgaat agcgtggggg ccaggcttcc   72840
gggccccaac gagccctccg tcccaacaag gtccgccggg ccggggggtcg ggttcgggac   72900 cgagggctc  tggtcgtcgg gggcgcgctg gtacaccgga tgccccggga atagctcccc   72960
cgacaggagg gaggcgtcga acggccgccc gaggatagct cgcgcgagga aggggtcctc   73020
gtcggtggcg ctggcggcga ggacgtcctc gccgcccgcc acaaacggga gctcctcggt   73080
ggcctcgctg ccaacaaacc gcacgtcggg ggggccgggg gggtccgggt tttcccacaa   73140
caccgcgacc ggggtcatgg agatgtccac gagcaccaga cacggcgggc cccgggcgag   73200
gggccgctcg gcgatgagcg cggacaggcg cgggagctgt gccgccagac acgcgttttc   73260
aatcgggttc aggtcggcgt gcaggaggcg gacggcccac gtctcgatgt cggacgacac   73320
ggcatcgcgc aaggcggcgt ccggcccgcg agcgcgtgag tcaaacagcg tgagacacag   73380
ctccagctcc gactcgcggg aaaaggccgt ggtgttgcgg agcgccacga cgacgggcgc   73440
gcccaggagc actgccgcca gcaccaggtc catggccgta acgcgcgccg cggggggtgcg   73500 gtgggtggcg gcggccggca cggcgacgtg ctggcccgtg ggccggtaga gggcgttggg   73560
gggagcgggg ggtgacgcct cgcgcccccc cgagggggctc agcgtctgcc cagattccag   73620
acgcgcggtc agaagggcgt cgaaactgtc atactctgtg tagtcgtccg gaaacatgca   73680
ggtccaaaga gcggccagag cggtgcttgg gagacacatg cgcccgagga cgctcaccgc   73740
cgccagcgcc tgggcgggac tcagctttcc cagcgcggcg ccgcgctcgg ttcccagctc   73800
ggggaccgag cgccagggcg ccaggggggtc ggtttcggac aacttgccgc ggcgccagtc   73860
tgccagccgc gtgccgaaca tgaggccccg ggtcggaggg cctccggtcg aaaacactgg   73920
cagcacgcgg atgcgggcgt ctggatgcgg ggtcaggcgc tgcacgaata gcatggaatc   73980
tgctgcgttc tgaaacgcac gggggagggt gagatgcatg tactcgtgtt ggcggaccag   74040
atccaggcgc caaaaggtgt aaatgtgttc cggggagctg gccaccagcg ccaccagcac   74100
gtcgttctcg ttaaaggaaa cgcggtgcct agtggagctg tggggcccga gcggcggtcc   74160
cggggccgcc gcgtcacccc cccattccag ctgggcccag cgacacccaa actcgcgcgt   74220
gagagtggtc gcgacgaggg cgacgtagag ctcggccgcc gcatccatcg aggccccca    74280 tctcgcctgg cggtggcgca caaagcgtcc gaagagctga aagttggcgg cctgggcgtc   74340
gctgagggcc agctgaagcc ggttgatgac ggtgatgacg tacatggccg tgacggtcga   74400
ggccgactcc agggtgtccg tcggaagcgg ggggcgaatg catgccgcct cgggacacat   74460
cagcagcgcg ccgagcttgt cggtcacggc cgggaagcag agcgcgtact gcagtggcgt   74520
tccatccggg accaaaaagc tgggggcgaa cggccgatcc agcgtactgg tggcctcgcg   74580
cagcaccagg ggcccagggc ctccgctcac tcgcaggtac gcctcgcccc ggcggcgcag   74640
catctgcggg tcggcctctt ggccgggtgg ggcggacgcc cgggcgcggg cgtctagggc   74700
gcgaagatcc acgagcaggg gcgcgggcgc ggcggccgcg cccgcgcccg tctggcctgt   74760
ggccttggcg tacgcgctat ataagcccat gcggcgttgg atgagctccc gcgcgccccg   74820
gaactcctcc accgcccatg gggccaggtc cccggccacc gcgtcgaatt ccgccaacag   74880 gcccccccagg gtgtcaaagt tcatctccca ggccacccct ggcaccacct cgtcccgcag   74940 ccggggcgctc aggtcggcgt gttgggccac gcgccccccg agctcctcca cggccccggc   75000
```

-continued

```
ccgctcggcg ctcttggcgc ccaggacgcc ctggtacttg gcgggaaggc gctcgtagtc   75060
ccgctgggct cgcagccccg acacagtgtt ggtggtgtcc tgcagggcgc gaagctgctc   75120
gcatgccgcg cgaaatccct cgggcgattt ccaggccccc ccgcgaacgc ggccgaagcg   75180
accccatacc tcgtcccact ccgcctcggc ctcctcgaga gacctccgca gggcctcgac   75240
gcggcgacgg gtgtcgaaga gcgcctgcag gcgcgcgccc tgtcgcgtca ggaggcccgg   75300
gccgtcgccg ctggccgcgt ttagcgggtg cgtctcaaag gtacgctggg catgttccaa   75360
ccaggcgacc gcctgcacgt cgagctcgcg cgccttctcc gtctggtcca acagaatttc   75420
gacctgatcc gcgatctcct ccgccgagcg cgcctggtcc agcgtcttgg ccacggtcgc   75480
cgggacggcg accaccttca gcagggtctt cagattggcc agaccctcgg cctcgagctg   75540
ggccccgcgc tcgcgcgcgg ccagcacctc ccgcagcccc gccgtgaccc gctcggtggc   75600
ttcggcgcgc tgctgtttgg cgcgcaccac ggcgtccttg gtatcggcca ggtcctgtcg   75660
ggtcacgaat gcgacgtagt cggcgtacgc cgtgtccttc acggggctct ggtccacgcg   75720
ctccagcgcc gccacgcacg ccaccagcgc gtcctcgctc gggcagggca gggtgacccc   75780
tgcccggaca agctcggcgg ccgccgccgg gtcgttgcgc accgcggata tctcctccgc   75840
ggcggcggcc aggtccagcg ccacgcttcc gatcgcgcgc cgcgcgtcgg cccggagggc   75900
gtccaggcga tcgcggatat ccacgtactc ggcgtagccc ttttgaaaaa acggcacgta   75960
ctggcgcagg gccggcacgc cccccaagtc ttccgacagg tgtaggacgg cctcgtggta   76020
gtcgataaac ccgtcgttcg cctgggcccg ctccagcagc cccccgcca gccgcagaag    76080 ccgcgccagg ggctcggtgt ccacccgaaa catgtcggcg tacgtgtcgg ccgcggcccc   76140
gaaggccgcg ctccagtcga tgcggtgaat ggctgcgagc gggggggagca tggggtggcg   76200 ctggttctcg ggggtgtatg ggttaaacgc aagggccgtc tccagggcaa gggtcaccgc   76260
cttggcgttg gttcccagcg cctgttcggc ccgctttcgg aagtcccggg ggttgtagcc   76320
gtgcgtgccc gccagcgcct gcaggcgacg gagctcgacc acgtcaaact cggcaccgct   76380
ttccacgcgg tccagcacgg cctccacgtc ggcggcccag cgctcgtggc tactgcgggc   76440
gcgctgggcc gccatcttct ctctcaggtc ggcgatggcg gcctcaagtt cgtcggcgcg   76500
gcgtcgcgtg gcgccgatga cctttcccag ctcctgcagg gcgcgcccgc tgggggagtg   76560
gtccccggcc gtcccttcgg cgtgcaacag gcccccgaac ctgccctcgt ggcccgcgag   76620
gctttcccgc gcgccggtgg tcgcgcgcgt cgcggcctgg atcagggagg catgctctcc   76680
ctccggttgg ttggcggccc ggcgcacctg gacgacaagg tcggctgccg ccgaccctaa   76740
ggtcgtgagc tgggcgatgg cccccgcgc gtccagggcc aaccgagtcg ccttgacgta    76800
tcccgcggcc ctgtcggcca tggccgctag gaaggccagg ggggaggccg ggtcgctggc   76860
ggccgcgccc agggccgtca ccgcgtcgac caggacgcgg tgcgcccgca cggccgcatc   76920
caccgtcgac gcggggtctg ccgtcgcgac ggcggcgctg ccggcgttga tggcgttcga   76980
gacggcgtgg gctatgatcg gggcgtgatc ggcgaagaac tgcaagagaa acggagtctc   77040
tggggcgtcg gcgaacaggt tcttcagcac caccacgaag ctgggatgca agccagacag   77100
agccgtcgcc gtgtccggag tcgggtgctc caggcatct cggtactgcc ccagcagccc    77160
ccacatgtcc gcccgcagcg ccgccgtaac ctcagggggc gcccccgaa cggcctcggg    77220 gaggtccgac cagcccgccg gcagggaggc ccgcagggtc gccaggacgg ccggacaggc   77280
ctttagcccc acaaagtcag ggagggggcg caggacccc tggagtttgt gcaagaactt    77340
ctcccgggcg tcgcgggcca ccttcgcccg ctcccgcgct ccctcgagca ttgcctccag   77400
```

-continued

```
ggagcgcgcg cgctcccgca aacgggcacg cgcatcgggg gcgagctctg ccgtcagctt   77460
ggcggcatcc atggcccgcg cctgccgcag cgcttcctcg gccatgcgcg tggcctctgg   77520
cgacagcccg ccgtcgtcgg ggtagggcga cgcgccgggc gcaggaacaa aggccgcgtc   77580
gctgtccagc tgctggccca gggccgcatc tagggcgtcg aagcgccgca gctcggccag   77640
acccgagctg cggcgcgcct gctggtcgtt aatgtcgcgg atgctgcgcg ccagctcgtc   77700
cagcggcttg cgttctatca gcccttggtt ggcggcgtcc gtcaggacgg agagccaggc   77760
cgccaggtcc tcgggggcgt ccagcgtctg gccccgctgg atcagatccc gcaacaggat   77820
ggccgtgggg ctggtcgcga tcgggggcgg ggcgggaatg gcggcgcgct gcgcgatgtc   77880
ccgcgtgtgc tggtcgaaga caggcaggga ctcgagcagc tggaccacgg gcacgacggc   77940
ggccgaagcc acgtgaaacc ggcggtcgtt gttgtcgctg gcctgtagag ccttggcgct   78000
gtatacggcc ccccggtaaa agtactcctt aaccgcgccc tcgatcgccc gacgggcctg   78060
ggtccgcacc tcctccagcc gaacctgaac ggcctcgggg cccagggggg gtgggcgcgg   78120
agccccctgc ggggccgccc cggccggggc gggcattacg ccgaggggcc cggcgtgctg   78180
tgagaccgcg tcgaccccgc gagcgagggc gtcgagggcc tcgcgcatct ggcgatcctc   78240
cgcctccacc ctaatctctt cgccacgggc aaatttggcc agagcctgga ctctatacag   78300
aagcggttct gggtgcgtcg gggtggcggg ggcaaaaagg gtgtccgggt gggcctgcga   78360
gcgctccaga agccactcgc cgaggcgtgt atacagattg gccggcgggg ccgcgcgaag   78420
ctgcagctcc aggtccgcga gttccccgta aaaggcgtcc gtctcccgaa tgacatccct   78480
agccacaagg atcagcttcg ccagcgccag gcgaccgatc agagagtttt cgtccagcac   78540
gtgctggacg aggggcagat gggcggccac gtcggccagg ctcaggcgcg tggaggccag   78600
aaagtccccc acggccgttt tccggggcag catgctcagg gtaaactcca gcagggcggc   78660
ggccgggccg gccacccccgg cctgggtgtg cgtccgggcc ccgttctcga tgagaaaggc   78720
gaggacgcgt tcaaagaaaa aaataacaca gagctccagc agccccggag aagccggata   78780
cggcgaccgt aaggcgctga tggtgagccg cgaacacgcg gcgacctcgc gggccagggt   78840
ggcggagcac gcggtgaact taaccgccgt ggcggccacg tttgggtggg cctcgaacag   78900
ctgggcgagg tctgcgcccg ggggctcggg tgagcggcga gtcttcagcg cctcgagggc   78960
ctgtgaggac gccggaacca tgggcccgtc gtcctcgccc gcctcggcga ccggcggccc   79020
ggccgggtcg gggggtgccg aggcgaggac aggctccgga acggaggcgg ggaccgcggc   79080
cccgacgggg gttttgcctt tggggggtgga tttcttcttg gttttggcag ggggggccga   79140
gcgtttcgtt ttctcccccg aagtcaggtc ttcgacgctg gaaggcggag tccaggtggg   79200
tcggcggcgc ttgggaaggc cggccgagta gcgtgcccgg tgccgaccaa ccgggacgac   79260
gcccatctcc aggacccgca tgtcgtcgtc atcttcttcg gccgcctctg cggcgggggt   79320 cttggggggcg gagggaggcg gtggtgggat cgcggagggt gggtcggcgg aggggggatc   79380
cgtgggtggg gtacccttta gggccaccgc ccatacatcg tcgggcgccc gattcgggcg   79440
cttggcctct ggttttgccg acggaccggc cgtcccccgg gatgtctcgg aggccctgtc   79500
gtcgcgacgg gcccgggtcg gtggcggcga ctggcggct gtgggcgggt gtggccccgg   79560 ccccctccc ccctcccggg ggccacgcc gacgcagggc tcccccaggc ccgcgatctc   79620
gccccgcagg gggtgcgtga tggccacgcg ccgttcgctg aacgcttcgt cctgcatgta   79680
agtctcgctg gccccgtaaa gatgcagagc cgcggccgtc aagtccgcag gagccgcggg   79740
```

-continued

```
ttccgggccc dacggcacga aaaacaccat ggctcccgcc caccgtacgt ccgggcgatc    79800
gcgggtgtaa tacgtcaggt atggatacat gtcccccgcc cgcactttgg cgatgaacgc    79860
gggggtgccc tccggaaggc catgcgggtc aaaaaggtat gcggtgtcgc cgtccctgaa    79920
cagccccatc cctagggggc caatggttag gagcgtgtac gacaggggg gcagggccca    79980 cgggccggcg aagaacgtgt gtgcggggca ttgtgtctcc agcaggcctg ccgcgggctc    80040
cccgaagaag cccacctcgc cgtatacgcg cgagaagaca cagcgcagtc cgccgcgcgc    80100
ccctgggtac tcgaggaagt tggggagctc gacgatcgaa cacatgcgcg gcggcccagg    80160
gcccgcagtc gcgcgcgtcc actcgccccc ctcgaccaaa catccctcga tggcctccgc    80220
ggacagaacg tcgcgagggc ccacatcaaa tatgaggctg agaaaggaca gcgacgagcg    80280
catgcacgat accgaccccc ccggctccag gtcgggcgcg aactggttcc gagcaccggt    80340
gaccacgatg tcgcgatccc ccccgcgttc catcgtggag tgcggtgggg tgcccgcgat    80400
catatgtgcc ctgcgggcca gagacccggc ctgtttatgg accggacccc cggggttagt    80460
gttgtttccg ccacccacgc ccccgtacca tggccccggt tccctgatt aggctacgag    80520 tcgcggtgat cgcttcccaa aaaccgagct gcgtttgtct gtcttggtct tcccccccc    80580 cagcccgcac accataacac cgagaacaac acacggggg gggcggaaca taataaagct    80640
ttattggtaa ctagttaacg gcaagtccgt gggtggcgcg acggtgtcct ccgggatcat    80700
ctcgtcgtcc tcgacggggg tgttggaatg aggcgcctcc tcgcggtcca cctggcgtgg    80760
gccgtgccca taggcctccg gcttctgtgc gtccatgggc gtaggcgcgg ggagactgtt    80820
tccggcgtcg cggacctcca ggtccctggg agcctccggt ccggctaacg gacgaaacgc    80880
ggaagcgcga aacacgccgt cggtgacccg caggagctcg ttcatcagta accaatccat    80940
actcagcgta acgccagcc cctggcgaga cagatccacg gagtccggaa ccgcggtcgt    81000
ctggcccagg gggccgaggc tgtagtcccc ccaggcccct aggtcgcgac ggctcgtaag    81060 cacgacgcg tcgccgcgg ggctttgcgg ggggcgtcc tcgggcgcat gcgccattac    81120
ctctcggatg gccgcggcgc gctggtcggc cgagctgacc aagggcgcca cgaccacggc    81180
gcgctccgtc tgcaggccct tccacgtgtc gtggagttcc tggacaaact cggccacggg    81240
ctcgggtccc gcggccgcgc gcgcggcttg atagcaggcc gacagacgcc gccagcgcgc    81300
tagaaactga cccatgaaac aaaacccggg gacctggtct cccgacagca gcttcgacgc    81360
ccgggcgtga atgccggaca cgacggacag aaacccgtga atttcgcgcc ggaccacggc    81420
cagcacgttg tcctcgtgcg acacctgggc cgccagctcg tcgcacaccc ccaggtcgcg    81480
cgtggtttcg gtgatgacgg aacgcaggct cgcgagggac gcgaccagcg cgcgcttggc    81540
gtcgtgatac atgctgcagt actgactcac cgcgtccccc atggcctcgg ggggccaggg    81600
ccccaggcgg tcgggcgtgt ccccgaccac cgcatacagg cggcgcccgt cgctctcgaa    81660
ccgacactcg aaaaaggcgg agagcgtgcg catgtgcagc cgcagcagca cgatggcgtc    81720
ctccagttgg cgaatcaggg ggtcggcgcg ctcggcgagg tcctgcagca cccccgggc    81780 agccagggcg tacatgctaa tcaacaggag gctggtgccc acctcggggg gcggggggg    81840 ctgcagttgg accaggggcc gcagctgctc gacggcaccc ctggagatca cgtacagctc    81900
ccggagcagc tgctctatgt tgtcggccat ctgcatagtg gggccgaggc cgccccgggc    81960
ggccggttcg aggagagtga tcagcgcgcc cagtttggtg cgatggccct cgaccgtggg    82020
gagatagccc agcccaaagt cccgggccca ggccaacaca cgcagggcga actcgaccgg    82080
gcggggaagg taggccgcgc tacacgtggc cctcagcgcg tccccaacca ccagggccag    82140
```

```
aacgtagggg acgaagcccg ggtcggcgag gacgttgggg tgaatgccct cgagggcggg    82200
gaagcggatc tgggtcgccg cggccaggtg gacagagggg gcatggctgg gctgcccgac    82260
ggggagaagc gcggacagcg gcgtggccgg ggtggtgggg gtgatgtccc agtgggtctg    82320
accatacacg tcgatccaga tgagcgccgt ctcgcggaga aggctgggtt gaccggaact    82380
aaagcggcgc tcggccgtct caaactcccc cacgagcgcc cgccgcaggc tcgccagatg    82440
ttccgtcggc acggccggcc ccatgatacg cgccagcgtc tggctcagaa cgcccccga    82500 caggccgacc gcctcacaga gccgcccgtg cgtgtgctcg ctggcgccct ggacccgcct    82560
gaaagttttt acgtagttgg catagtaccc gtattcccgc gccagaccaa acacgttcga    82620
ccccgcgagg gcaatgcacc caaagagctg ctggacttcg ccgagtccgt ggccggcggg    82680
cgtccgcgcg gggacgcccg ccgccagaaa cccctccagg gccgaaaggt agtgcgtgca    82740
gtgcgagggc gtgaacccag cgtcgatcag ggtgttgatc accacggagg gcgaattggt    82800
attctggatc aacgtccacg tctgctgcag cagagccagc agccgctgct gggcgccggc    82860
ggagggctgc tccccgagct gcagcaggct ggagacggca ggctggaaga ctgccagtgc    82920
cgacgaactc aggaacggca cgtcgggatc aaacacggcc acgtccgtcc gcacgcgcgc    82980
cattagcgtc cccgggggcg cacaggccga gcgcgggctg acgcggctga gggccgtcga    83040
cacgcgcacc tcctcgcggc tgcgaaccat cttgttggcc tccagtggcg gaatcattat    83100
ggccgggtcg atctcccgca cggtgtgctg aaactgcgcc aacaggggcg gcgggaccac    83160
agccccccgc tcgggggtcg tcaggtactc gtccaccagg gccaacgtaa agagggcccg    83220
tgtgagggga gtgagggtcg cgtcgtctat gcgctggagg tgcgccgaga acagcgtcac    83280
ccgattactc accagggcca agaaccggag gccctcttgc acgaacgggg cggggaagag    83340
caggctgtac gccggggtgg taaggttcgc gctgggctgc cccaacggga ccggcgccag    83400
cttgagcgac gtctccccaa gggcctcgat ggaggtccgc gggctcatgg ccaagcagct    83460
cttggtgacg gtttgccagc ggtctatcca ctccacggcg cactggcgga cgcggaccgg    83520
ccccagggcc gccgcggtgc gcaggccggc ggactccagc gcatgggacg tgtcggagcc    83580
ggtgaccgcg aggatggtgt ccttgatgac ctccatctcc cggaaggcct ggtcgggggc    83640
ctcggggaga gccaccacca agcggtgtac gagcaacccg gggaggttct cggccaagag    83700
cgccgtctcc ggaagcccgt gggcccggtg gagcgcgcac aggtgttcca gcagcggccg    83760
ccagcatgcc cgcgcgtctg ccggggcgat ggccgttccc gacaacagaa acgccgccat    83820
ggcggcgcgc agcttggccg tggccagaaa cgccgggtcg tccgccccgt ttgccgtctc    83880
ggccgtgggg gttggcggtt ggcgaaggcc ggctaggctc gccaataggc gctgcatagg    83940
tccgtccgag ggcggaccgg cgggtgaggt cgtgacgacg ggggcctcgg acgggagacc    84000
gcggtctgcc atgacgcccg gctcgcgtgg gtgggggaca gcgtagacca acgacgagac    84060
cgggcgggaa tgactgtcgt gcgctgtagg gagcggcgaa ttatcgatcc cccgcggccc    84120
tccaggaacc ccgcaggcgt tgcgagtacc ccgcgtcttc gcggggtgtt atacggccac    84180
ttaagtcccg gcatcccgtt cgcggaccca ggcccggggg attgtccgga tgtgcgggca    84240
gcccggacgg cgtgggttgc ggactttcgg cggggcggcc caaatggccc tttaaacgtg    84300
tgtatacgga cgcgccgggc cagtcggcca acacaaccca ccggaggcgg tagccgcgtt    84360
tggctgtggg gtgggtggtt ccgccttgcg tgagtgtcct ttcgaccccc cccctccccc    84420
gggtcttgct aggtcgcgat ctgtggtcgc aatgaagacc aatccgctac ccgcaacccc    84480
```

-continued

```
ttccgtgtgg ggcgggagta ccgtggaact ccccccaccc acacgcgata ccgcggggca  84540
gggcctgctt cggcgcgtcc tgcgcccccc gatctctcgc cgcgacggcc cagtgctccc  84600 caggggggtcg ggaccccgga gggcggccag cacgctgtgg ttgcttggcc tggacggcac  84660
agacgcgccc cctggggcgc tgacccccaa cgacgatacc gaacaggccc tggacaagat  84720
cctgcggggc accatgcgcg ggggggcggc cctgatcggc tccccgcgcc atcatctaac  84780
ccgccaagtg atcctgacgg atctgtgcca acccaacgcg gatcgtgccg ggacgctgct  84840
tctggcgctg cggcacccg ccgacctgcc tcacctggcc caccagcgcg ccccgccagg  84900
ccggcagacc gagcggctgg gcgaggcctg gggccagctg atggaggcga ccgccctggg  84960
gtcggggcga gccgagagcg ggtgcacgcg cgcgggcctc gtgtcgttta acttcctggt  85020
ggcggcgtgt gccgcctcgt acgacgcgcg cgacgccgcc gatgcggtac gggcccacgt  85080
cacggccaac taccgcggga cgcgggtggg ggcgcgcctg gatcgttttt ccgagtgtct  85140
gcgcgccatg gttcacacgc acgtcttccc ccacgaggtc atgcggtttt tcgggggggct  85200 ggtgtcgtgg gtcacccagg acgagctagc gagcgtcacc gccgtgtgcg ccgggcccca  85260
ggaggcggcg cacaccggcc acccgggccg gccccgctcg gccgtgatcc tcccggcgtg  85320
tgcgttcgtg gacctggacg ccgagctggg gctggggggc ccgggcgcgg cgtttctgta  85380
cctggtattc acttaccgcc agcgccggga ccaggagctg tgttgtgtgt acgtgatcaa  85440
gagccagctc ccccccgcgcg ggttggagcc ggccctggag cggctgtttg ggcgcctccg  85500
gatcaccaac acgattcacg gcaccgagga catgacgccc ccggccccaa accgaaaccc  85560
cgacttcccc ctcgcgggcc tggccgccaa tccccaaacc ccgcgttgct ctgctggcca  85620
ggtcacgaac ccccagttcg ccgacaggct gtaccgctgg cagccggacc tgcgggggcg  85680
ccccaccgca cgcacctgta cgtacgccgc ctttgcagag ctcggcatga tgcccgagga  85740
tagtccccgc tgcctgcacc gcaccgagcg ctttggggcg gtcagcgtcc ccgttgtcat  85800
cctggaaggc gtggtgtggc gccccggcga gtggcgggcc tgcgcgtgag cgtagcaaac  85860
gccccgccca cacaacgctc cgcccccaac cccttccccg ctgtcactcg ttgttcgttg  85920
acccggacgt ccgccaaata aagccactga aacccgaaac gcgagtgttg taacgtcctt  85980
tgggcgggag gaagccacaa aatgcaaatg ggatacatgg aaggaacaca cccccgtgac  86040
tcaggacatc ggcgtgtcct tttgggtttc actgaaactg gcccgcgccc cacccctgcg  86100
cgatgtggat aaaaagccag cgcgggtggt ttagggtacc acaggtgggt gctttggaaa  86160
cttgtcggtc gccgtgctcc tgtgagcttg cgtccctccc cggtttcctt tgcgctcccg  86220
ccttccggac ctgctctcgc ctatcttctt tggctctcgg tgcgattcgt caggcagtgg  86280
ccttgtcgaa tctcgacccc accactcgcc ggacccgccg acgtccctc tcgagcccgc  86340 cgaaacccgc cgcgtctgtt gaaatggcca gccgccccgc cgcatcctct cccgtcgaag  86400
cgcgggcccc ggttggggga caggaggccg gcggccccag cgcagccacc caggggggagg  86460 ccgccggggc ccctctcgcc cgcggccacc acgtgtactg ccagcgagtc aatggcgtga  86520
tggtgctttc cgacaagacg cccgggtccg cgtcctaccg catcagcgat agcaactttg  86580
tccaatgtgg ttccaactgc accatgatca tagacggaga cgtggtgcgc gggcgccccc  86640
aggacccggg ggccgcggca tccccccgctc ccttcgttgc ggtgacaaac atcggagccg  86700
gcagcgacgg cgggaccgcc gtcgtggcat tcggggggaac cccacgtcgc tcggcgggga  86760
cgtctaccgg tacccagacg accgacgtcc ccaccgaggc ccttggggggc cccctcctc  86820 ctccccgctt caccctgggt ggcggctgtt gttcctgtcg cgacacacgg cgccgctctg  86880
```

```
cggtattcgg gggggagggg ccatagccaa tccatgaccc tgtatgtcac ggagaaggcg   86940
gacgggaccc tcccagcctc caccctggtc cgccttctgg tccacgcata taagcgcgga   87000
ctaaaaacag ggatgtacta ctgcaaggtt cgcaaggcga ccaacagcgg ggtctttggc   87060
ggcgacgaca acattgtctg cacgagctgc gcgctgtgac cgacaaaccc cctccgcgcc   87120
aggcccgccg ccactgtcgt cgccgtccca cgcgctcccc cgctgccatg gattccgcgg   87180
ccccagccct ctcccccgct ctgacggccc atacgggcca gagcgcgccg gcggacctgg   87240
cgatccagat tccaaagtgc cccgacccccg agaggtactt ctacacctcc cagtgtcccg   87300
acattaacca cctgcgctcc ctcagcatcc ttaaccgctg gctggaaacc gagcttgttt   87360
tcgtggggga cgaggaggac gtctccaagc tttccgaggg cgagctcagc ttttaccgct   87420
tcctcttcgc tttcctgtcg gccgccgacg acctggttac ggaaaacctg ggcggcctct   87480
ccggcctgtt tgagcagaag gacattctcc actactacgt ggagcaggaa tgcatcgaag   87540
tcgtacactc gcgcgtgtac aacatcatcc agctggtgct tttttcacaac aacgaccagg   87600 cgcgccgcga gtacgtggcc ggcaccatca accacccggc catccgcgcc aaggtggact   87660
ggctggaagc gcgggtgcgg gaatgcgcct ccgttccgga aaagttcatc ctcatgatcc   87720
tcatcgaggg catcttttttt gccgcctcgt ttgccgccat cgcctacctt cgcaccaaca   87780
accttctgcg ggtcacctgc cagtcaaacg acctcatcag ccgggacgag gccgtgcaca   87840
cgacggcctc gtgttacatc tacaacaact acctcggcgg gcacgccaag cccccgcccg   87900
accgcgtgta cgggctgttc cgccaggcgg tcgagatcga gatcggattt atccgatccc   87960
aggcgccgac ggacagccat atcctgagcc cggcggcgct ggcggccatc gaaaactacg   88020
tgcgattcag cgcggatcgc ctgttggggc ttatccacat gaagccactg ttttccgccc   88080 cacccccccga cgccagcttt ccgctgagcc tcatgtccac cgacaaacac accaattttt   88140
tcgagtgtcg cagcacctcc tacgccgggg cggtcgtcaa cgatctgtga gggtcgcggc   88200
gcgcttctac ccgtgtttgc ccataataaa cctctgaacc aaactttggg tctcattgtg   88260
attcttgtca gggacgcggg ggtgggagag ataaaaggc ggcgcaaaaa gcagtaacca   88320
ggtccgtcca gattctgagg gcataggata ccataatttt attggtgggt cgtttgttcg   88380
gggacaagcg cgctcgtctg acgtttgggc tactcgtccc agaatttggc caggacgtcc   88440
ttgtagaacg cgggtgggggg ggcctgggtc cgcagctgct ccagaaacct gtcggcgata   88500
tcaggggccg tgatatgccg ggtcacaata gatcgcgcca ggttttcgtc gcggatgtcc   88560
tggtagatag gcaggcgttt cagaagagtc cacggccccc gctccttggg gccgataagc   88620
gatatgacgt acttaatgta gcggtgttcc accagctcgg tgatggtcat gggatcgggg   88680
agccagtcca gggactctgg ggcgtcgtgg atgacgtggc gtcgccggct ggccacataa   88740
ctgcggtgct cttccagcag ctgcgcgttc gggacctgga cgagctcggg cggggtgagt   88800
atctccgagg aggacgacct ggggccgggg tggcccccgg taacgtcccg gggatccagg   88860
gggaggtcct cgtcgtcttc gtatccgccg gcgatctgtt gggttagaat ttcggtccac   88920
gagacgcgca tctcggtgcc gccggcggcc ggcggcaaag ggggcctggt ttccgtggag   88980
cgcgagctgg tgtgttcccg gcggatggcc cgccgggtct gagagcgact cggggggggtc   89040 cagtgacatt cgcgcagcac atcctccacg gaggcgtagg tgttattggg atggaggtcg   89100
gtgtggcagc ggacaaagag ggccaggaac tgggggtagc tcatcttaaa gtactttagt   89160
atatcgcgac agttgatcgt gggaatgtag caggcgctaa tatccaacac aatatcacag   89220
```

-continued

```
cccatcaaca ggaggtcagt gtctgtggtg tacacgtacg cgaccgtgtt ggtgtgatag   89280
aggttggcgc aggcatcgtc cgcctccagc tgacccgagt taatgtaggc gtaccccagg   89340 gccccggagaa cgcgaataca gaacagatgc gccagacgca gggccggctt cgagggcgcg   89400
gcggacggca gcgcggctcc ggacccggcc gtcccccggg tccccgaggc cagagaggtg   89460
ccgcgccggc gcatgttgga aaaggcagag ctgggtctgg agtcggtgat gggggaaggc   89520
ggtggagagg cgtccacgtc actggcctcc tcgtccgtcc ggcattgggc cgtcgtgcgg   89580
gccaggatgg ccttggctcc aaacacaacc ggctccatac aattgacccc gcgatcggta   89640
acgaagatgg ggaaaaggga cttttgggta aacacctta ataagcgaca gaggcagtgt   89700
agcgtaatgg cctcgcggtc gtaactgggg tatcggcgct gatatttgac caccaacgtg   89760
tacatgacgt tccacaggtc cacggcgatg ggggtgaagt acccggccgg ggccccaagg   89820
ccctggcgct tgaccagatg gtgtgtgtgg gcaaacttca tcatcccgaa caaacccatg   89880
tcaggtcgat tgtaactgcg gatcggccta actaaggcgt ggttggtgcg acggtccggg   89940
acacccgagc ctgtctctct gtgtatggtg acccagacaa caacaccgac acaagaggac   90000
aataatccgt taggggacgc tctttataat ttcgatggcc caactccacg cggattggtg   90060
cagcaccctg catgcgccgg tgtgggccaa acttcccccc gctcattgcc tcttccaaaa   90120
gggtgtggcc taacgagctg gggggcgtatt taatcaggct agcgcggcgg gcctgccgta   90180
gtttctggct cggtgagcga cggtccggtt gcttgggtcc cctggctgcc agcaaaaccc   90240
caccctcgca gcggcatacg cccccctccgc gtcccgcacc cgagaccccg gcccggctgc   90300
cctcaccacc gaagcccacc tcgtcactgt ggggtgttcc cagcccgcat tgggatgacg   90360
gattcccctg gcggtgtggc ccccgcctcc cccgtggagg acgcgtcgga cgcgtccctc   90420
gggcagccgg aggaggggggc gccctgccag gtggtcctgc agggcgccga acttaatgga   90480
atcctacagg cgtttgcccc gctgcgcacg agccttctgg actcgcttct ggttatgggc   90540
gaccggggca tccttatcca taacacgatc tttggggagc aggtgttcct gccccctggaa   90600 cactcgcaat tcagtcggta tcgctggcgc ggacccacgg cggcgttcct gtctctcgtg   90660
gaccagaagc gctccctcct gagcgtgttt cgcgccaacc agtacccgga cctacgtcgg   90720
gtggagttgg cgatcacggg ccaggccccg tttcgcacgc tggttcagcg catatggacg   90780
acgacgtccg acggcgaggc cgttgagcta gccagcgaga cgctgatgaa gcgcgaactg   90840
acgagctttg tggtgctggt tccccaggga acccccgacg ttcagttgcg cctgacgagg   90900
ccgcagctca ccaaggtcct taacgcgacc ggggccgata gtgccacgcc caccacgttc   90960
gagctcgggg ttaacggcaa attttccgtg ttcaccacga gtacctgcgt cacatttgct   91020 gccccgcgagg agggcgtgtc gtccagcacc agcacccagg tccagatcct gtccaacgcg   91080
ctcaccaagg cgggccaggc ggccgccaac gccaagacgg tgtacgggga aaatacccat   91140
cgcaccttct ctgtggtcgt cgacgattgc agcatgcggg cggtgctccg gcgactgcag   91200
gtcgccgggg gcaccctcaa gttcttcctc acgaccccccg tccccagtct gtgcgtcacc   91260
gccaccggtc ccaacgcggt atcggcggta tttctcctga aaccccagaa gatttgcctg   91320
gactggctgg gtcatagcca ggggtctcct tcagccggga gctcggcctc ccgggcctct   91380
gggagcgagc caacagacag ccaggactcc gcgtcggacg cggtcagcca cggcgatccg   91440
gaagacctcg atggcgctgc ccgggcggga gaggcggggg cctcgcacgc ctgtccgatg   91500
ccgtcgtcga ccacgcgggt cactcccacg accaagcggg ggcgctcggg gggcgaggat   91560
gcgcgcgcgg acacggccct aaagaaacct aagacggggt cgcccaccgc acccccgccc   91620
```

-continued

```
acagatccag tcccctgga cacggaggac gactccgatg cggcggacgg gacggcggcc   91680
cgtcccgccg ctccagacgc ccggagcgga agccgttacg cgtgttactt tcgcgacctc   91740
ccgaccggag aagcaagccc cggcgccttc tccgccttcc gggggggccc ccaaaccccg   91800
tatggttttg gattcccctg acgggcgggg gccttggcgg ccgcccaact ctcgcaccat   91860
cccgggttaa tgtaaataaa cttggtattg cccaacactc tcccgcgtgt cgcgtgtggt   91920
tcatgtgtgt gcctggcgtc ccccaccctc gggttcgtgt atttcctttc cctgtcctta   91980
taaaagccgt atgtggggcg ctgacggaac caccccgcgt gccatcacgg ccaaggcgcg   92040
ggatgctccg caacgacagc caccgggccg cgtccccgga ggacggccag ggacgggtcg   92100
acgacggacg gccacacctc gcgtgcgtgg gggccctggc gcggggggttc atgcatatct   92160 ggcttcaggc cgccacgctg ggttttgcgg gatcggtcgt tatgtcgcgc gggccgtacg   92220
cgaatgccgc gtctggggcg ttcgccgtcg ggtgcgccgt gctgggcttt atgcgcgcac   92280
cccctcccct cgcgcggccc accgcgcgga tatacgcctg gctcaaactg gcggccggtg   92340
gagcggccct tgttctgtgg agtctcgggg agcccggaac gcagccgggg gccccgggcc   92400
cggccaccca gtgcctggcg ctgggcgccg cctatgcggc gctcctggtg ctcgccgatg   92460
acgtctatcc gctctttctc ctcgccccgg ggccctgtt cgtcggcacc ctggggatgg   92520
tcgtcggcgg gctgacgatc ggaggcagcg cgcgctactg gtggatcggt gggcccgccg   92580
cggccgcctt ggccgcggcg gtgttggcgg gcccggggggc gaccaccgcc agggactgct   92640
tctccagggc gtgccccgac caccgccgcg tctgcgtcat cgtcgcaggc gagtctgttt   92700
cccgccgccc cccggaggac ccagagcgac ccggggaccc cgggccaccg tccccccga   92760 caccccaacg atcccagggg ccgccggccg atgaggtcgc accggccggg gtagcgcggc   92820
ccgaaaacgt ctgggtgccc gtggtcacct ttctgggggc gggcgcgctc gccgtcaaga   92880
cggtgcgaga acatgcccgg gaaacgccgg gcccgggcct gccgctgtgg ccccaggtgt   92940
ttctcggagg ccatgtggcg gtggccctga cggagctgtg tcaggcgctt atgccctggg   93000
accttacgga cccgctgctg tttgttcacg ccggactgca ggtcatcaac ctcgggttgg   93060
tgtttcggtt ttccgaggtt gtcgtgtatg cggcgctagg gggtgccgtg tggatttcgt   93120
tggcgcaggt gctggggctc cggcgtcgcc tgcacaggaa ggaccccggg gacggggccc   93180
ggttggcggc gacgcttcgg ggcctcttct tctccgtgta cgcgctgggg tttggggtgg   93240
gggcgctgct gtgccctccg gggtcaacgg gcgggtggtc gggcgattga tatatttttc   93300
aataaaaggc attagtcccg aagaccgccg gtgtgtgatg atttcgccat aacacccaaa   93360
ccccggatgg ggcccgggta taaattccgg aaggggacac gggctaccct cactaccgag   93420
ggcgcttggt cgggaggccg catcgaacgc acaccccccat ccggtggtcc gtgtggaggt   93480
cgtttttcag tgcccggtct cgctttgccg ggaacgctag ccgatccctc gcgaggggga   93540
ggcgtcgggc atggccccgg ggcgggtggg ccttgccgtg gtcctgtgga gcctgttgtg   93600
gctcggggcg ggggtggccg ggggctcgga aactgcctcc accgggccca cgatcaccgc   93660
gggagcggtg acgaacgcga gcgaggcccc cacatcgggg tccccgggt cagccgccag   93720 cccggaagtc acccccacat cgaccccaaa ccccaacaat gtcacacaaa acaaaaccac   93780
ccccaccgag ccggccagcc ccccaacaac ccccaagccc acctccacgc ccaaaagccc   93840
ccccacgtcc acccccgacc ccaaacccaa gaacaacacc accccccgcca agtcgggccg   93900 ccccactaaa cccccggggc ccgtgtggtg cgaccgccgc gacccattgg cccggtacgg   93960
```

-continued

```
ctcgcgggtg cagatccgat gccggtttcg gaattccacc cgcatggagt tccgcctcca   94020
gatatggcgt tactccatgg gtccgtcccc cccaatcgct ccggctcccg acctagagga   94080
ggtcctgacg aacatcaccg ccccacccgg gggactcctg gtgtacgaca gcgcccccaa   94140
cctgacggac ccccacgtgc tctgggcgga ggggggccggc ccgggcgccg accctccgtt   94200
gtattctgtc accgggccgc tgccgaccca gcggctgatt atcggcgagg tgacgcccgc   94260
gacccaggga atgtattact tggcctgggg ccggatggac agcccgcacg agtacgggac   94320
gtgggtgcgc gtccgcatgt tccgcccccc gtctctgacc ctccagcccc acgcggtgat   94380
ggagggtcag ccgttcaagg cgacgtgcac ggccgccgcc tactacccgc gtaaccccgt   94440
ggagtttgtc tggttcgagg acgaccgcca ggtgtttaac ccgggccaga tcgacacgca   94500
gacgcacgag cacccgacg ggttcaccac agtctctacc gtgacctccg aggctgtcgg   94560
cggccaggtc cccccgcgga ccttcacctg ccagatgacg tggcaccgcg actccgtgat   94620
gttctcgcga cgcaatgcca ccgggctggc cctggtgctg ccgcggccaa ccatcaccat   94680
ggaatttggg gtccggcatg tggtctgcac ggccggctgc gtccccgagg gcgtgacgtt   94740
tgcctggttc ctgggggacg acccctcacc ggcggctaag tcggccgtta cggcccagga   94800
gtcgtgcgac caccccgggc tggctacggt ccggtccacc ctgcccattt cgtacgacta   94860
cagcgagtac atctgtcggt tgaccggata tccggccggg attcccgttc tagagcacca   94920
cggcagtcac cagcccccac ccagggaccc caccgagcgg caggtgatcg aggcgatcga   94980
gtgggtgggg attggaatcg gggttctcgc ggcggggggtc ctggtcgtaa cggcaatcgt   95040
gtacgtcgtc cgcacatcac agtcgcggca gcgtcatcgg cggtaacgcg agacccccc   95100 gttacctttt taatatctat atagtttggt cccctctat cccgcccacc gctgggcgct   95160
ataaagccgc caccctctct tccctcaggt catccttggt cgatcccgaa cgacacacgg   95220
cgtggagcaa aacgcctccc cctgagccgc tttcctacca acacaacggc atgcctctgc   95280
gggcatcgga acacgcctac cggccctgg gccccgggac acccccatg cgggctcggc   95340 tccccgccgc ggcctgggtt ggcgtcggga ccatcatcgg gggagttgtg atcattgccg   95400
cgttggtcct cgtgccctcg cgggcctcgt gggcactttc cccatgcgac agcggatggc   95460
acgagttcaa cctcgggtgc atatcctggg atccgacccc catggagcac gagcaggcgg   95520
tcggcggctg tagcgccccg gcgacccctga tccccgcgc ggctgccaaa cagctggccg   95580
ccgtcgcacg cgtccagtcg gcaagatcct cgggctactg gtgggtgagc ggagacggca   95640
ttcgggcctg cctgcggctc gtcgacggcg tcggcggtat tgaccagttt tgcgaggagc   95700
ccgcccttcg catatgctac tatccccgca gtcccggggg ctttgttcag tttgtaactt   95760
cgacccgcaa cgcgctgggg ctgccgtgag gcgcgtgtac tgcggtctgt ctcgtctcct   95820
cttctcccct tccctccccc tccgcatccc aggatcacac cggccaacga gggttggggg   95880
ggtccggcac ggacccaaaa taataaacac acaatcacgt gcgataaaaa gaacacgcgg   95940
tcccctgtgg tgtttttggt tatttttatt aaatctcgtc gacaaacagg gggaaagggg   96000
cgtggtctag cgacggcagc acgggcggag gcgttcaccg gctccggcgt ccttcgcgtt   96060
taagcttggt caggagggcg ctcagggcgg cgacgttggt cgggccgtcg ttggtcaggg   96120
cgttggctcg atggcgggcg aggacgggcg aggggctcaa cggcgggggc gggggtccgg   96180
tgcggcccgg gggggaaaat agggcggatc cccccagtc gtacaggga ttttccgcct   96240 caatgtacgg ggaggccggc gctgcattcg ccgtgttcac gcagacgttt tcgtagaccc   96300
gcatccatgg tatttcctcg tagacacgcc ccccgtcctc gctcacggtc tcgtatattg   96360
```

```
actcgtcgtc ctcgtagggg gcgtgccgtt cgcgggccga ggcggcgtgg gtggctttgc   96420
ggcgggcgtc gtcgtcgtcg tcgtcggccg tcagatacgt ggcttccatc tggtcgggtt   96480
ctccctccgg ggcgggtccc cacacccgtg gccgatcgag gctccccaga gacgcgcgcc   96540
ggacaagaag ggggcacgtc gccgccggcg gtcgcctgtc gggtcccgcg acgttacggg   96600
ccgggaggcg cgggggcacc tcccccatgt gcgtgtaata cgtggccggc tgtgcggccg   96660
cagcgggggg ctcggcgacc gggtcgtccg catccggaag cgggggcccc gcgccgtccg   96720
cacggcgcct ccggaaccgc cgggtggacg gcgcgggggt cgagtgtagg cgaggtcggg   96780
ggaggggcgg gggctcgttg tcgcgccgcg cccgctgaat cttttcccga caggtcccac   96840
cccccgcgcg atgcccccc gggccgcggg ccatgtcgtc cggggganggc cccgcggacc   96900 acgtcgtccg gcgagacgcc acgagccgca ggatggactc gtagtggagc gacggcgccc   96960
cgctgcggag cagatccgcg gccagggcgg ccccgaacca agccttgatg ctcaactcca   97020
tccgggccca gctgggggcg gtcatcgtgg ggaacagggg ggcggtggtc cgacagaaac   97080
gctcctggct gtccaccgcg gcccgcagat actcgttgtt caggctgtcg gtggcccaga   97140
cgccgtaccc ggtgagggtc gcgttgatga tatactgggc gtggtgatgg acgatcgaca   97200
gaacctccac cgtggatacc acggtatcca cggtcccgta cgtaccgccg ctccgcttgc   97260
cggtctgcca caggttggct aggcacgtca ggtggcccag gacgtcgctg accgccgccc   97320
tgagcgccat gcactgcatg gagccggtcg tgccgctggg accccggtcc agatggcgcg   97380
cgaacgtttc cgcgggcgcc tccgggctgc cgccgagcgg gaggaaccgg cgattggagg   97440
gactcagccg gtgacatacg tgcttgtccg tcgtccacag catccaggac gcccaccggt   97500
acagcacgga gacgtaggcc aggagctcgt tgagccgcag tgcggtgtcg gtgctggggc   97560
ggcttgggtc cgccgggcgc ataaagaaca tgtactgctg aatccgatgg agggcgtcgc   97620
gcaggccggc cacggtggcg gcgtacttgg ccgccgcggc cccgctcttg aacggggtgc   97680
gcgccagcag ctttggcgcc agggtgggcc gcagcagcac gtgaaggctg gggtcgcagt   97740
cgcccacggg gtcctcgggg acgtccaggc cgctgggcac caccgtctgc aggtacttcc   97800
agtactgcgt gaggatggcg cggctcaact ggccgccggg cagctccacc tcgcccagcg   97860
cctgggtggc ggccgaagcg tagtgccgga tgtactcgta gtgcgggtcg ctggcgagcc   97920
cgtccacgat caaactctcg ggaaccgtgt tgtgttgccg cgcggccaac cggacgctgc   97980
gatcggtgca ggtcagaaac gccggctgcg cgtcgtcgga gcgctgccgc aaggcgccca   98040
cggccgcgct aaggagcccc tccggggtgg ggagcagaca cccgccgaag atgcgccgct   98100
cgggaacgcc cgcgttgtcg ccgcggatca ggttggcagg cgtcaggcac cgcgccagcc   98160
gcagggagct cgcgccgcgc gtccggcgct gcatggtgac gcccgttcgg tcgggacccg   98220
ccggtcggag ttatgccgcg tccagggcca tcggggcgct ttttatcggg aggagcttat   98280
gggcgtggcg ggcctcccag cccggtcgcg cgcctccccg acacgtgcgc ccgcaggggc   98340 gcggcccct cgtctcccat cagcagtttc ctaaactggg acatgatgtc caccacgcgg   98400
acccgcgggc ccaacacgga cccgccgctt acggggcgg gggggaaggg ctccaggtcc   98460
ttgagcagaa aggcggggtc tgccgtcccg gacacggggg cccggggcgc ggaggaggcg   98520
gggcgcagat ccacgtgctc cgcggccgcg cggacgtccg cccagaactt ggcgggggtg   98580
gtgcgcgcgt acagggctg ggtcgctcgg aggacacacg cgtagcgcag gggggtgtac   98640
gtgcccacct cggggggccgt gaatcccccg tcaaacgcgg ccagtgtcac gcacgccacc   98700
```

-continued

```
acggtgtcgg caaagcccag cagccgctgc aggacgagcc cggcggccag aatggcgcgc    98760
gtggtcgcag cgtcgtcccg gcgccggtgc gcgtccccgc acgcccgggc gtactttaag    98820
gtcactgtcg ccagggccgt gtgcagcgcg tacaccgcag cgcccagcac ggcgttgagc    98880
ccgctgttgg cgagcagccg gcgcgctgcg gtgtcgccca gcgcctcgtg ctcggccccc    98940
acgaccgcgg ggcttcccag gggcagggcg cgaaacagct cctcccgcgc cacgtccgca    99000
aaggcggggt ggtgcacgtg cgggtgcagg cgcgccccca cgaccaccga gagccactgg    99060
accgtctgct ccgccatcac cgccaacaca tccagcacgc gccccaggaa ggcggcctcc    99120
cgcgtcaaaa cgcaccggac ggcgtcggga ttgaagcggg cgagcagggc cccggtggcc    99180
aggtacgtca tgcggccggc atagcgggcg gccacgcgac agtcgcggtc cagcagcgcg    99240
cgcaccccgg gccagtacag cagggacccc agcgagctgc gaaacaccgc ggcgtcgggg    99300
ccggattggg gggacactaa cccccccgcg ctcagtaacg gcacggccgc ggccccgacg    99360
ggacgcaacg ccgtgaggct cgcgaactgc cgcctcagct cggcagccct gtcgtccagg    99420
tccgacccgc gcgcctctgc gtgaaggcgc gtcccgcaca cccacccgtt gatggccagc    99480
cgcacgacgg catccgccaa aaagctcatc gcctgggcgg ggctggtttt tgttcgacga    99540
tccgtcaggt caagaatccc atcgcccgtg atataccagg ccaacgcctc gccctgctgc    99600
agggtttggc ggaaaaacac cgcggggttg tcgggggagg cgaagtgcat gaccccacg    99660 cgcgataacc cgaacgcgct atccggacac gggtaaaacc cggccggatg ccccagggct    99720
agggcggagc gcacggactc gtcccacacg gcaacctgag gggccagtcg atccaacggg    99780
aatgccgccc ggagctccgg gccggcacg cgtccctcca gaacctccac cttgggcggg    99840
gaacgggccc cgccgccgtc ctccggcccg acgtcttccg ggtagtcgtc ctcctcgtac    99900
tgcagttcct ctaggaacag cggcgacggc gccaccgcg aaccgccgac ccgccccaaa    99960
atagcccgcg cgtcgacggg acccaggtat cccccctgcc gggcctgcgg aggaccgcgg    100020
ggaacctcat catcatcgtc caggcgaccg cgcaccgact ggctacgggc cgcatcgggc    100080
ccggggcgct gccgggacgc tcggcgatgg gatgagggcg gggcttccga cgcgcgccgt    100140
cgtcgggctc gcgggccttc ccgtcgacgg cgcacgggcg gctcgtcgcc cgccatctcc    100200
tccagagcct ctagctcgct gtcgtcatcc ccgcggaaca ccgcacgcag gtaccccatg    100260
aaccccaccc catcgcccgc tggctcgtcc gccacgggcg aggcgcgggg gcgggtggat    100320
gcgcgcctcc tgcgccccgc gggttcgcga ccgacatgg tggcgataga cgcgggttat    100380
cggatgtccg ctaccccca aaaaagaaaa agacccaca gcgcggatgg aggtcggggt    100440
aggtgccgcc ggaccccctc gcgatgggaa tggacgggag cgacggggcc ggcgcaaaaa    100500
acgcagtatc tcccgcgaag gctacccgcc gccccagccc ccggccaaat gcggaaacgg    100560
tcccgcgctc tcgcctttat acgcgggccg ccctgcgaca caatcacccg tccgtggttt    100620
cgaatctaca cgacaggccc gcagacgcgg ctaacacaca cgccggcaac ccagacccca    100680
gtgggttggt tgcgcggtcc cgtctcctgg ctagttcttt cccccaccac caaataatca    100740
gacgacaacc gcaggttttt gtaatgtatg tgctcgtgtt tattgtggat acgaaccggg    100800
gacgggaggg gaaaacccag acgggggatg cgggtccggt cgcgcccct acccaccgta    100860 ctcgtcaatt ccaagggcat cggtaaacat ctgctcaaac tcgaagtcgg ccatatccag    100920
agcgccgtag ggggcggagt cgtggggggt aaatcccgga cccggggaat ccccgtcccc    100980
caacatgtcc agatcgaaat cgtctagcgc gtcggcatgc gccatcgcca cgtcctcgcc    101040
gtctaagtgg agctcgtccc ccaggctgac atcggtcggg ggggccgtcg acagtctgcg    101100
```

-continued

```
cgtgtgtccc gcggggagaa aggacaggcg cggagccgcc agccccgcct cttcgggggc 101160
gtcgtcgtcc gggagatcga gcaggccctc gatggtagac ccgtaattgt ttttcgtacg 101220
cgcgcggctg tacgcgtgtt cccgcatgac cgcctcggag ggcgaggtcg tgaagctgga 101280
atacgagtcc aacttcgccc gaatcaacac cataaagtac ccagaggcgc gggcctggtt 101340
gccatgcagg gtgggagggg tcgtcaacgg cgccctggc tcctccgtag ccgcgctgcg 101400
caccagcggg aggttaaggt gctcgcgaat gtggtttagc tcccgcagcc ggcgggcctc 101460
gattggcact ccccggacgg tgagcgctcc gttgacgaac atgaagggct ggaacagacc 101520
cgccaactga cgccagctct ccaggtcgca acagaggcag tcaaacaggt cgggccgcat 101580
catctgctcg gcgtacgcgg cccataggat ctcgcgggtc aaaaatagat acaaatgcaa 101640
aaacagaaca cgcgccagac gagcggtctc tcggtagtac ctgtccgcga tcgtggcgcg 101700
cagcatttct cccaggtcgc gatcgcgtcc gcgcatgtgc gcctggcggt gcagctgccg 101760
gacgctggcg cgcaggtacc ggtacagggc cgagcagaag ttggccaaca cggttcgata 101820
gctctcctcc cgcgcccgta gctcggcgtg aagaaacga gagagcgctt cgtagtagag 101880
cccgaggccg tcgcgggtgg ccggaagcgt cgggaaggcc acgtcgccgt gggcgcgaat 101940
gtcgatttgg gcgcgttcgg ggacgtacgc gtcccccat tccaccacat cgctgggcag 102000
cgttgatagg aatttacact cccggtacag gtcggcgttg gtcggtaacg ccgaaaacaa 102060
atcctcgttc caggtatcga gcatggtaca tagcgcgggg cccgcgctaa agcccaagtc 102120
gtcgaggaga cggttaaaga gggcggcggg ggggacgggc atgggcgggg agggcatgag 102180
ctgggcctgg ctcaggcgcc ccgttgcgta cagcggaggg gccgccgggg tgtttttggg 102240 accccccggcc gggcggggg gtggtggcga agcgccgtcc gcgtccatgt cggcaaacag 102300
ctcgtcgacc aagaggtcca ttgggtgggg ttgatacggg aaagacgata tcgggctttt 102360
gatgcgatcg tccccgcccg cccagagagt gtgggacgcc cgacggcgcg ggaagagaaa 102420 aaccccaaa cgcgttagag gaccggacgg accttatggg gggaagtggg cagcgggaac 102480
cccgtccgtt cccgaggaat gacagcccgt ggtcgccacc ccgcatttaa gcaacccgca 102540
cgggccgccc cgtacctcgt gacttccccc cacattggct cctgtcacgt gaaggcaaac 102600
cgagggcggc tgtccaaccc acccccgcc acccagtcac ggtccccgtc ggattgggaa 102660
acaaaggcac gcaacgccaa caccgaatga acccctgttg gtgctttatt gtctgggtac 102720
ggaagttttt cactcgacgg gccgtctggg gcgagaagcg gagcgggctg gggctcgagg 102780
tcgctcggtg gggcgcgacg ccgcagaacg ccctcgagtc gccgtggccg cgtcgacgtc 102840
ctgcaccacg tctggattca ccaactcgtt ggcgcgctga atcaggtttt tgccctcgca 102900
gaccgtcacg cggatggtgg tgatgccaag gagttcgttg aggtcttcgt ctgtgcgcgg 102960
acgcgacatg tcccagagct ggaccgccgc catccgggca tgcatggccg ccaggcgccc 103020
aaccgcggcg cagaagacgc gcttgttaaa gccggccacc cggggggtcc atggcgcgtc 103080
ggggtttggg ggggcggtgc taaagtgcag ctttctggcc agccctgcg cgggtgtctt 103140 ggatcgggtt ggcgccgtcg acgcgggggc gtctgggagt gcggcggatt ctggctgggc 103200
cgatttcctg ccgcgggtgg tctccgccgc cggggccgcg ggggccttag tcgccacccg 103260
ctgggttcgg ggggcccggg gggcggtggt gggtgtgcgt ccggcccctc cggacccagc 103320
gggcggcgga ggcgcccgcg caggccccgg ggcggacaaa accgccccgg aaacgggacg 103380
ccgcgtccgg gggacctccg ggtgttcgtc gtcttcggat gacgagcccc cgtagagggc 103440
```

-continued

```
ataatccgac tcgtcgtact ggacgaaacg gacctcgccc cttgggcgcg cgcgtgtctg 103500
tagggcgcca cggcgggagg tgtcaggcgg actatcggga ctcgccatac atgaagacgg 103560
ggtgtagtac agatcctcgt actcatcgcg cggaacctcc cgcggacccg acttcacgga 103620
gcggcgagag gtcatggttc cacgaacacg ctagggtcgg atgcgcggac aattaggcct 103680
gggttcggac ggcgggggtg gtgcaggtgt ggagaggtcg agcgataggg gcggcccggg 103740
agagaagaga gggtccgcaa aacccactgg ggatgcgtga gtggccctct gtgggcggtg 103800
ggggagagtc ttataggaag tgcatataac cacaacccat gggtctaacc aatccccagg 103860
ggccaagaaa cagacacgcc ccaaacggtc tcggtttccg cgaggaaggg gaagtcctgg 103920
gacaccctcc accccaccc ctcaccccac acagggcggg ttcaggcgtg cccggcagcc 103980
agtagcctct ggcagatctg acagacgtgt gcgataatac acacgcccat cgaggccatg 104040
cctacataaa agggcaccag ggccccgggg gcagacattt ggccagcgtt ttgggtctcg 104100
caccgcgcgc ccccgatccc atcgcgcccg ccctcctcgc cgggcggctc cccgtgcggg 104160
cccgcgtctc ccgccgctaa ggcgacgagc aagacaaaca acaggcccgc ccgacagacc 104220
cttctggggg ggcccatcgt ccctaacagg aagatgagtc agtggggatc cggggcgatc 104280
cttgtccagc cggacagctt gggtcggggg tacgatggcg actggcacac ggccgtcgct 104340
actcgcgggg gcggagtcgt gcaactgaac ctggtcaaca ggcgcgcggt ggctttttatg 104400 ccgaaggtca gcgggggactc cggatgggcc gtcgggcgcg tctctctgga cctgcgaatg 104460
gctatgccgg ctgactttttg tgcgattatt cacgcccccg cgctatccag cccagggcac 104520
cacgtaatac tgggtcttat cgactcgggg taccgcggaa ccgttatggc cgtggtcgta 104580
gcgcctaaaa ggacgcggga atttgccccc gggaccctgc gggtcgacgt gacgttcctg 104640
gacatcctgg cgaccccccc ggccctcacc gagccgattt ccctgcggca gttcccgcaa 104700
ctggcgcccc cccctccaac cggggccggg atacgcgcag atccttggtt ggagggggcg 104760
ctcggggacc caagcgtgac tcctgcccta ccggcgcgac gccgagggcg gtccctcgtc 104820
tatgccggcg agctgacgcc ggttcagacg gaacacgggg acggcgtacg agaagccatc 104880
gccttccttc caaaacgcga ggaggatgcc ggtttcgaca ttgtcgtccg tcgcccggtc 104940
accgtcccgg caaacggcac cacggtcgtg cagccatccc tccgcatgct ccacgcggac 105000
gccgggcccg cggcctgcta tgtgctgggg cggtcgtcgc tcaacgcccg cggcctcctg 105060
gtcgttccta cgcgctggct ccccgggcac gtatgtgcgt ttgttgttta caaccttacg 105120
ggggttcctg tgaccctcga ggccggcgcc aaggtcgccc agctcctggt tgcgggggcg 105180
gacgctcttc cttggatccc cccggacaac tttcacggga ccaaagcgct tcgaaactac 105240
cccaggggtg ttccggactc aaccgccgaa cccaggaacc cgccgctcct ggtgtttacg 105300
aacgagtttg acgcggaggc ccccccgagc gagcgcggga ccggggggttt tggctctacc 105360 ggtatttagc ccatagcttg gggttcgttc cgggcaataa aaaacgtttg tatctcatct 105420
ttcctgtgtg tagttgtttc tgttggatgc ctgtgggtct atcacacccg cccctccatc 105480
ccacaaacac agaacacacg ggttggatga aaacacgcat ttattgaccc aaaacacacg 105540
gagctgctcg agatgggcca gggcgaggtg cggttgggga ggctgtaggt ctgggaacgg 105600
acacgcgggg acacgattcc ggtttggggt ccgggagggc gtcgccgttt cgggcggcag 105660
gcgccagcgt aacctccggg ggcggcgtgt ggggtgcccc caaggagggc gcctcggtca 105720
ccccaagccc ccccgagcgg gttcccccgg caaccccgaa ggcggagagg ccaagggccc 105780
gttcggcgat ggccacatcc tccatgacca cgtcgctctc ggccatgctc cgaatagcct 105840
```

```
gggagacgag cacatccgcg gacttgtcag ccgcccccac ggacatgtac atctgcagga 105900
tggtggccat acacgtgtcc gccaggcgcc gcatcttgtc ctgatgggcc gccacggccc 105960
cgtcgatcgt gggggcctcg agcccggggt ggtggcgcgc cagtcgttct aggttcacca 106020
tgcaggcgtg gtacgtgcgg gccaaggcgc gggccttcac gaggcgtcgg gtgtcgtcca 106080
gggaccccag ggcgtcatcg agcgtgatgg gggcgggaag tagcgcgtta acgaccacca 106140
gggcctcctg cagccgcggc tccgcctccg agggcggaac ggccgcgcgg atcatctcat 106200
attgttcctc ggggcgcgct ccccagccac atatagcccc gagaagagaa gccatcgcgg 106260
gcgggtactg gcccttgggc gcgcggacgc aatggggcag gaagacggga accgcgggga 106320
gaggcgggcg gccgggactc ccgtggaggt gaccgcgctt tatgcgaccg acgggtgcgt 106380
tattacctct tcgatcgccc tcctcacaaa ctctctactg ggggccgagc cggtttatat 106440
attcagctac gacgcataca cgcacgatgg ccgtgccgac gggcccacgg agcaagacag 106500
gttcgaagag agtcgggcgc tctaccaagc gtcgggcggg ctaaatggcg actccttccg 106560
agtaaccttt tgtttattgg ggacggaagt gggtgggacc caccaggccc gcgggcgaac 106620
ccgacccatg ttcgtctgtc gcttcgagcg agcggacgac gtcgccgcgc tacaggacgc 106680
cctggcgcac gggaccccgc tacaaccgga ccacatcgcc gccaccctgg acgcggaggc 106740
cacgttcgcg ctgcatgcga acatgatcct ggctctcacc gtggccgtca acaacgccag 106800
cccccgcacc ggacgcgacg ccgccgcggc gcagtatgat cagggcgcgt ccctacgctc 106860
gctcgtgggg cgcacgtccc tgggacaacg cggccttacc acgctatacg tccaccacga 106920
ggcgcgcgtg ctggccgcgt accgcagggc gtattatgga agcgcgcaga gtcccttctg 106980
gtttcttagc aaattcgggc ctgacgaaaa aagcctggtg ctcaccactc ggtactacct 107040
gcttcaggcc cagcgtctgg ggggcgcggg ggccacgtac gacctgcagg ccatcaagga 107100
catctgcgcc acctacgcga ttccccacgc ccccgcccc gacaccgtca gcgccgcgtc 107160
cctgacctcg tttgccgcca tcacgcggtt ctgttgcacg agccagtacg cccgcggggc 107220
cgcggcggcc gggtttccgc tttacgtgga gcgccgtatt gcggccgacg tccgcgagac 107280
cagtgcgctg gagaagttca taacccacga tcgcagttgc ctgcgcgtgt ccgaccgtga 107340
attcattacg tacatttacc tggcccattt tgagtgtttc agcccccccgc gcctagccac 107400 gcatcttcgg gccgtgacga cccaggaccc caaccccgcg gccaacacgg agcagccctc 107460
gcccctgggc agggaggccg tggaacaatt tttttgccac gtgcgcgccc aactgaatat 107520
cggggagtac gtcaaacaca acgtgacccc ccgggagacc gtcctggatg gcgatacggc 107580
caaggcctac ctgcgcgctc gcacgtacgc gcccgggggcc ctgacgcccg ccccgcgta 107640 ttgcgggggc gtggactccg ccaccaaaat gatggggcgt ttggcggacg ccgaaaagct 107700
cctggtcccc cgcgggtggc ccgcgtttgc gcccgccagt cccggggagg atacggcggg 107760
cggcacgccg cccccacaga cctgcggaat cgtcaagcgc ctcctgagac tggccgccac 107820
ggaacaacag gacaccacgc ccccggcgat cgcggcgctt atccgtaatg cggcggtgca 107880
gactcccctg cccgtctacc ggatatccat ggtccccacg ggacaggcat ttgccgcgct 107940
ggcctgggac gactgggccc gcataacgcg ggacgctcgc ctggccgaag cggtcgtgtc 108000
cgccgaagcg gcggcgcacc ccgaccacgg cgcgctgggc aggcggctca cggatcgcat 108060
ccgcgcccag ggccccgtga tgcccccctgg cggcctggat gccgggggggc agatgtacgt 108120 gaatcgcaac gagatattta acggcgcgct ggcaatcaca aacatcatcc tggatctcga 108180
```

```
catcgccctg aaggagcccg tcccctttcg ccggctccac gaggccctgg gccactttag 108240
gcgcggggct ctggcggcgg ttcagctcct gtttcccgcg gccgcgtgg accccgacgc 108300 atatccctgt tattttttca aaagcgcatg tcggcccggc ccggcgtccg tgggttccgg 108360
cagcggactc ggcaacgacg acgacgggga ctggtttccc tgctacgacg acgcggtga 108420 tgaggagtgg gcggaggacc cgggcgccat ggacacatcc cacgatcccc cggacgacga 108480
ggttgcctac tttgacctgt gccacgaagt cggccccacg gcggaacctc gcgaaacgga 108540
ttcgcccgtg tgttcctgca ccgacaagat cggactgcgg gtgtgcatgc ccgtccccgc 108600
cccgtacgtc gtccacggtt ctctaacgat gcgggggggtg gcacgggtca tccagcaggc 108660
ggtgctgttg gaccgagatt ttgtggaggc catcgggagc tacgtaaaaa acttcctgtt 108720
gatcgatacg ggggtgtacg cccacggcca cagcctgcgt ttgccgtatt ttgccaaaat 108780
cgcccccgac gggcctgcgt gcggaaggct gctgccagtg tttgtgatcc cccccgcctg 108840
caaagacgtt ccggcgtttg tcgccgcgca cgccgacccg cggcgcttcc attttcacgc 108900
cccgcccacc tatctcgctt cccccccggga gatccgtgtc ctgcacagcc tgggtgggga 108960
ctatgtgagc ttctttgaaa ggaaggcgtc ccgcaacgcg ctggaacact ttgggcgacg 109020
cgagaccctg acggaggtcc tgggtcggta caacgtacag ccggatgcgg gggggaccgt 109080
cgaggggttc gcatcggaac tgctggggcg gatagtcgcg tgcatcgaaa cccactttcc 109140
cgaacacgcc ggcgaatatc aggccgtatc cgtccggcgg gccgtcagta aggacgactg 109200
ggtcctccta cagctagtcc ccgttcgcgg taccctgcag caaagcctgt cgtgtctgcg 109260
ctttaagcac ggccgggcga gtcgcgccac ggcgcggaca ttcgtcgcgc tgagcgtcgg 109320
ggccaacaac cgcctgtgcg tgtccttgtg tcagcagtgc tttgccgcca aatgcgacag 109380
caaccgcctg cacacgctgt ttaccattga cgccggcacg ccatgctcgc cgtccgttcc 109440
ctgcagcacc tctcaaccgt cgtcttgata acggcgtacg gcctcgtgct cgtgtggtac 109500
accgtcttcg gtgccagtcc gctgcaccga tgtatttacg cggtacgccc caccggcacc 109560
aacaacgaca ccgccctcgt gtggatgaaa atgaaccaga ccctattgtt tctgggggcc 109620
ccgacgcacc cccccaacgg gggctggcgc aaccacgccc atatctgcta cgccaatctt 109680
atcgcgggta gggtcgtgcc cttccaggtc ccacccgacg ccacgaatcg tcggatcatg 109740
aacgtccacg aggcagttaa ctgtctggag accctatggt acacacgggt gcgtctggtg 109800
gtcgtagggt ggttcctgta tctggcgttc gtcgccctcc accaacgccg atgtatgttt 109860
ggtgtcgtga gtcccgccca caagatggtg gccccggcca cctacctctt gaactacgca 109920
ggccgcatcg tatcgagcgt gttcctgcag taccccctaca cgaaaattac ccgcctgctc 109980
tgcgagctgt cggtccagcg gcaaaacctg gttcagttgt ttgagacgga cccggtcacc 110040
ttcttgtacc accgccccgc catcgggggtc atcgtaggct gcgagttgat gctacgcttt 110100
gtggccgtgg gtctcatcgt cggcaccgct ttcatatccc gggggggcatg tgcgatcaca 110160 taccccctgt ttctgaccat caccacctgg tgttttgtct ccaccatcgg cctgacagag 110220
ctgtattgta ttctgcggcg gggcccggcc cccaagaacg cagacaaggc cgccgccccg 110280
gggcgatcca aggggctgtc gggcgtctgc gggcgctgtt gttccatcat cctgtcgggc 110340
atcgcaatgc gattgtgtta tatcgccgtg gtggccgggg tggtgctcgt ggcgcttcac 110400
tacgagcagg agatccagag cgcgcctgttt gatgtatgac gtcacatcca ggccggcgga 110460
aaccggaacg gcatatgcaa actggaaact gtcctgtctt ggggcccacc cacccgacgc 110520
gtcatatgta aatgaaaatc gttcccccga ggccatgtgt agcctggatc ccaacgaccc 110580
```

```
cgcccatggg tcccaattgg ccgtcccgtt accaagacca acccagccag cgtatccacc 110640
cccgcccggg tccccgcgga agcggaacgg tgtatgtgat atgctaatta aatacatgcc 110700
acgtacttat ggtgtctgat tggtccttgt ctgtgccgga ggtggggcgg gggccccgcc 110760
cggggggcgg aactaggagg ggtttgggag agccggcccc ggcaccacgg gtataaggac 110820
atccaccacc cggccggtgg tggtgtgcag ccgtgttcca accacggtca cgcttcggtg 110880
cctctccccg attcgggccc ggtcgcttgc taccggtgcg ccaccaccag aggccatatc 110940
cgacacccca gccccgacgg cagccgacag cccggtcatg gcgactgaca ttgatatgct 111000
aattgacctc ggcctggacc tctccgacag cgatctggac gaggacccc ccgagccggc 111060 ggagagccgc cgcgacgacc tggaatcgga cagcaacggg gagtgttcct cgtcggacga 111120
ggacatggaa gacccccacg gagaggacgg accggagccg atactcgacg ccgctcgccc 111180
ggcggtccgc ccgtctcgtc cagaagaccc cggcgtaccc agcacccaga cgcctcgtcc 111240
gacggagcgg cagggcccca acgatcctca accagcgccc cacagtgtgt ggtcgcgcct 111300
cggggcccgg cgaccgtctt gctcccccga gcggcacggg ggcaaggtgg cccgcctcca 111360 accccaccg accaaagccc agcctgcccg cggcggacgc cgtgggcgtc gcaggggtcg 111420
gggtcgcggt ggtcccgggg ccgccgatgg tttgtcggac ccccgccggc gtgcccccag 111480
aaccaatcgc aacccggggg gaccccgccc cggggcgggg tggacggacg gccccggcgc 111540
cccccatggc gaggcgtggc gcggaagtga gcagcccgac ccacccggag gcccgcggac 111600
acggagcgtg cgccaagcac cccccccgct aatgacgctg gcgattgccc ccccgcccgc 111660 ggaccccgc gccccggccc cggagcgaaa ggcgcccgcc gccgacacca tcgacgccac 111720
cacgcggttg gtcctgcgct ccatctccga gcgcgcggcg gtcgaccgca tcagcgagag 111780
cttcggccgc agcgcacagg tcatgcacga cccctttggg gggcagccgt ttcccgccgc 111840
gaatagcccc tgggcccgg tgctggcggg ccaaggaggg ccctttgacg ccgagaccag 111900
acgggtctcc tgggaaacct tggtcgccca cggcccgagc ctctatcgca cttttgccgg 111960
caatcctcgg gccgcatcga ccgccaaggc catgcgcgac tgcgtgctgc gccaagaaaa 112020
tttcatcgag gcgctggcct ccgccgacga gacgctggcg tggtgcaaga tgtgcatcca 112080
ccacaacctg ccgctgcgcc cccaggaccc cattatcggg acggccgcgg cggtgctgga 112140
taacctcgcc acgcgcctgc ggcccttct ccagtgctac ctgaaggcgc gaggcctgtg 112200
cggcctggac gaactgtgtt cgcggcggcg tctggcggac attaaggaca ttgcatcctt 112260
cgtgtttgtc attctggcca ggctcgccaa ccgcgtcgag cgtggcgtcg cggagatcga 112320
ctacgcgacc cttggtgtcg gggtcggaga gaagatgcat ttctacctcc ccggggcctg 112380
catggcgggc ctgatcgaaa tcctagacac gcaccgccag gagtgttcga gtcgtgtctg 112440
cgagttgacg gccagtcaca tcgtcgcccc cccgtacgtg cacggcaaat attttttattg 112500 caactccctg tttttaggtac aataaaaaca aacatttca aacaaatcgc cccacgtgtt 112560
gtccttcttt gctcatggcc ggcggggcgt gggtcacggc agatggcggg ggtgggcccg 112620
gcgtacggcc tgggtgggcg gagggaacta acccaacgta taaatccgtc cccgctccaa 112680
ggccggtgtc atagtgccct taggagcttc ccgcccgggc gcatcccccc ttttgcacta 112740
tgacagcgac cccctcacc aacctgttct tacgggcccc ggacataacc cacgtggccc 112800 cccttactg cctcaacgcc acctggcagg ccgaaacggc catgcacacc agcaaaacgg 112860
actccgcttg cgtggccgtg cggagttacc tggtccgcgc ctcctgtgag accagcggca 112920
```

-continued

```
caatccactg ctttttcttt gcggtataca aggacaccca ccatacccct ccgctgatta 112980
ccgagctccg caactttgcg gacctggtta accacccgcc ggtcctacgc gaactggagg 113040
ataagcgcgg ggtgcggctg cggtgtgcgc ggccgtttag cgtcgggacg attaaggacg 113100
tctctgggtc cggcgcgtcc tcggcgggag agtacacgat aaacgggatc gtgtaccact 113160
gccactgtcg gtatccgttc tcaaaaacat gctggatggg ggcctccgcg gccctacagc 113220
acctgcgctc catcagctcc agcggcatgg ccgcccgcgc ggcagagcat cgacgcgtca 113280
agattaaaat taaggcgtga tctccaaccc cccatgaatg tgtgtaaccc cccccaaaaa 113340
aataaagagc cgtaacccaa ccaaaccagg cgtggtgtga gtttgtggac ccaaagccct 113400
cagagacaat gcgacaggcc agtatggacc gtgatacttt tatttattaa ctcacagggg 113460
cgcttaccgc cacaggaata ccagaataat gaccaccaca atcgcgacca ccccaaatac 113520
agatccgtgt cggcagccgc gctccgtgtg gacgatcggg gcgtcctcgg gctcatatag 113580
tcccaggggc cggcgggaag gaggagcagc ggaggccgcc ggcccccgc ccccggcgg 113640 gcccaccccg aacggaattc cattatgcac gaccccgccc cgacgccggc acgccggggg 113700
cccgtggccg cggcccgttg gtcgaacccc cggccccgcc catccgcgcc atctgccatg 113760
gacggggcgc gagggcgggt gggtccgcgc cccgccccgc atggcatctc attaccgccc 113820
gatccggcgg tttccgcttc cgttccgcat gctaacgagg aacgggcagg gggcggggcc 113880
cgggccccga cttcccggtt cggcggtaat gagatacgag ccccgcgcgc ccgttggccg 113940
tccccgggcc cccggtcccg cccgccggac gccgggacca acgggacggc gggcggccct 114000
tgggccgccc gccttgccgc ccccccattg gccggcgggc gggaccgccc caaggggggcg 114060 gggccgccgg gtaaaagaag tgagaacgcg aagcgttcgc acttcgtccc aatatatata 114120
tattattagg gcgaagtgcg agcactggcg ccgtgcccga ctccgcgccg gccccggggg 114180
cggacccggg cggcgggggg cgggtctctc cggcgcacat aaaggcccgg cgcgaccgac 114240
gcccgcagac ggcgccagcc acgaacgacg ggagcggctg cggagcacgc ggaccgggag 114300
cgggagtcgc agagggccgt cggagcggac ggcgtcggca tcgcgacgcc ccggctcggg 114360
atcgggatcg catcggaaag ggacacgcgc acgcgggggg gaaagacccg cccaccccac 114420
ccacgaaaca caggggacgc accccggggg cctccgacga cagaaaccca ccggtccgcc 114480
ttttttgcac gggtaagcac cttgggtggg cagaggaggg gggacgcggg ggcggaggag 114540
gggggacgcg ggggcggagg agggggggacg cggggggcgga ggagggggga cgcggggggcg 114600 gaggaggggg gacgcggggg cggaggaggg ggctcacccg cgttcgtgcc ttcccgcagg 114660
aggaacgccc tcgtcgaggc gaccggcggc gaccgttgcg tggaccgctt cctgctcgtc 114720 ggggggggggg gagccactgt ggtcctccgg gacgttttct ggatggccga catttccccca 114780 ggcgcttttg tgccttgtgt aaaagcgcgg cgtcccgctc tccgatcccc gcccctgggc 114840
acgcgcaagc gcaagcgccc tgcccgcccc ctctcatcgg agtctgaggt cgaatccgag 114900
acagccttgg agtctgaggt cgaatccgag acagcatcgg attcgaccga gtctgggac 114960 caggaggaag cccccgcat cggtggccgt agggcccccc ggaggcttgg ggggcggttt 115020
tttctggaca tgtcggcgga atccaccacg gggacggaaa cggatgcgtc ggtgtcggac 115080
gaccccgacg acacgtccga ctggtcttgt gacgacattc ccccacgacc caagcgggcc 115140
cgggtaaacc tgcggctcac tagctctccc gatcggcggg atggggttat ttttcctaag 115200
atggggcggg tccggtctac ccgggaaacg cagccccggg cccccacccc gtcggcccca 115260
agcccaaatg caatgctccg gcgctcggtg cgccaggccc agaggcggag cagcgcacga 115320
```

-continued

```
tggacccccg acctgggcta catgcgccag tgtatcaatc agctgtttcg ggtcctgcgg 115380
gtcgcccggg accccacgg cagtgccaac cgcctgcgcc acctgatacg cgactgttac 115440
ctgatgggat actgccgagc ccgtctggcc ccgcgcacgt ggtgccgctt gctgcaggtg 115500
tccggcggaa cctggggcat gcacctgcgc aacaccatac gggaggtgga ggctcgattc 115560
gacgccaccg cagaacccgt gtgcaagctt ccttgtttgg aggccagacg gtacggcccg 115620
gagtgtgatc ttagtaatct cgagattcat ctcagcgcga caagcgatga tgaaatctcc 115680
gatgccaccg atctggaggc cgccggttcg gaccacacgc tcgcgtccca gtccgacacg 115740
gaggatgccc cctcccccgt tacgctggaa accccagaac cccgcgggtc cctcgctgtg 115800
cgtctggagg atgagtttgg ggagtttgac tggacccccc aggagggctc ccagccctgg 115860
ctgtctgcgg tcgtggccga taccagctcc gtggaacgcc cgggcccatc cgattctggg 115920
gcgggtcgcg cagcagaaga ccgcaagtgt ctggacggct gccggaaaat gcgcttctcc 115980
accgcctgcc cctatccgtg cagcgacacg tttctccggc cgtgagtccg gtcgccccga 116040
cccccttgta tgtccccaaa ataaaagacc aaaatcaaag cgtttgtccc agcgtcttaa 116100
tggcgggaag ggcggagaga aacagaccac gcgtacatgg ggggtgtttg ggggtttatt 116160
gacatcgggg ctacagggtg gtaaccggat agcagatgtg aggaagtctg ggccgttcgc 116220
cgcgaacggc gatcagaggg tccgtttctt gcggaccacg gcccggtgat gtgggttgct 116280
cgtctaaaat ctcgggcata cccatacacg cacaacacgg acgccgcacc gaatgggacg 116340
tcgtaagggg gtgggaggta gctgggtggg gtttgtgcag agcaatcagg accgcagcc 116400 agcgcataca atcgcgctcc cgtccgttgg tcccgggcag gaccacgccg tactggtatt 116460
cgtaccggct gagcagggtc tccaggggggt ggttgggtgc cgcggggaac ggggtccacg 116520
ccacggtcca ctcgggcaaa aaccgagtcg gcacggccca cggttctccc acccacgcgt 116580
ctggggtctt gatggcgata aatcttaccc cgagccggat ttttttgggcg tattcgagaa 116640 acggcacaca cagatccgcc gcgcctacca cccacaagtg gtagaggcga gggggggctgg 116700 gttggtctcg gtgcaacagt cggaagcacg ccacggcgtc cacgacctcg gtgctctcca 116760
aggggctgtc ctccgcaaac aggcccgtgg tggtgtttgg ggggcagcga caggacctag 116820
tgcgcacgat cgggcgggtg ggtttgggta agtccatcag cggctcggcc aaccgtcgaa 116880
ggttggccgg gcgaacgacg accgggggtac ccagggggttc tgatgccaaa atgcggcact 116940
gcctaagcag gaagctccac agggccgggc ttgcgtcgac ggaagtccgg ggcagggcgt 117000
tgttctggtc aaggagggtc attacgttga cgacaacaac gcccatgttg gtatattaca 117060
ggcccgtgtc cggtttgggg cacttgcaga tttgtaaggc cacgcacggc ggggagacag 117120 gccgacgcg gggctgctct aaaaatttaa gggccctacg gtccacagac ccgccttccc 117180 ggggggggccc ttggagcgac cggcagcgga ggcgtccggg ggaggggagg gttatttacg 117240
ggggggtagg tcagggggtg ggtcgtcaaa ctgccgctcc ttaaaacccc ggggcccgtc 117300
gttcggggtg ctcgttggtt ggcactcacg gtgcggcgaa tggcctgtcg taagttttgt 117360
cgcgtttacg ggggacaggg caggaggaag gaggaggccg tcccgccgga gacaaagccg 117420
tcccgggtgt ttcctcatgg cccctttttat accccagccg aggacgcgtg cctgactcc 117480 ccgcccccgg gacccccaa accttcccac accacaccac ccggcgatgc cgagcgcctg 117540
tgtcatctgc aggagatcct ggcccagatg tacggaaacc aggactaccc catagaggac 117600
gaccccagcg cggatgccgc ggacgatgtc gacgaggacg ccccggacga cgtggcctat 117660
```

-continued

```
ccggaggaat acgcagagga gctttttctg cccggggacg cgaccggtcc ccttatcggg 117720
gccaacgacc acatccctcc cccgcgtggc gcatctcccc ccggtatacg acgacgcagc 117780
cgggatgaga ttggggccac gggatttacc gcagaagagc tggacgccat ggacaggcag 117840
gcggctcgag ccatcagccg cggcggcaag ccccccctcga ccatggccaa gctggtgact 117900
ggcatgggct ttacgatcca cggagcgctc accccaggat cggaggggtg tgtctttgac 117960
agcagccacc cagattaccc ccaacgggta atcgtgaagg cggggtggta cacgagcacg 118020
agccacgagg cgcgactgct gaggcgactg gaccacccgg cgatcctgcc cctcctggac 118080
ctgcatgtcg tctccggggt cacgtgtctg gtcctcccca agtaccaggc cgacctgtat 118140
acctatctga gtaggcgcct gaacccactg ggacgcccgc agatcgcagc ggtctcccgg 118200
cagctcctaa gcgccgttga ctacattcac cgccagggca ttatccaccg cgacattaag 118260
accgaaaata tttttattaa cacccccgag gacatttgcc tgggggactt tggtgccgcg 118320
tgcttcgtgc agggttcccg atcaagcccc ttcccctacg gaatcgccgg aaccatcgac 118380
accaacgccc ccgaggtcct ggccggggat ccgtatacca cgaccgtcga catttggagc 118440
gccggtctgg tgatcttcga gactgccgtc cacaacgcgt ccttgttctc ggcccccgc 118500 ggccccaaaa ggggcccgtg cgacagtcag atcacccgca tcatccgaca ggcccaggtc 118560
cacgttgacg agtttccccc gcatccagaa tcgcgcctca cctcgcgcta ccgctcccgc 118620
gcggccggga acaatcgccc gccttacacc cgaccggcct ggacccgcta ctacaagatg 118680
gacatagacg tcgaatatct ggtttgcaaa gccctcacct tcgacggcgc gcttcgcccc 118740
agcgccgcag agctgctttg tttgccgctg tttcaacaga aatgaccgcc cccgggggggc 118800 ggtgctgttt gcgggttggc acaaaaagac cccgacccgc gtctgtggtg tttttggcat 118860
catgtcgccg ggcgccatgc gtgccgttgt tcccattatc ccattccttt tggttcttgt 118920
cggtgtatcg ggggttccca ccaacgtctc ctccaccacc caaccccaac tccagaccac 118980
cggtcgtccc tcgcatgaag cccccaacat gacccagacc ggcaccaccg actctcccac 119040
cgccatcagc cttaccacgc ccgaccacac accccccatg ccaagtatcg gactggagga 119100
ggaggaggaa gaggaggagg gggccgggga tggcgaacat cttaaggggg gagatggac 119160 ccgtgacacc ctaccccagt ccccgggtcc agccgtcccg ttggccgggg atgacgagaa 119220
ggacaaaccc aaccgtcccg tagtcccacc ccccggtccc aacaactccc ccgcgcgccc 119280
cgagaccagt cgaccgaaga cacccccac cagtatcggg ccgctggcaa ctcgacccac 119340
gacccaactc ccctcaaagg ggcgaccctt ggttccgacg cctcaacata ccccgctgtt 119400
ctcgttcctc actgcctccc ccgccctgga caccctcttc gtcgtcagca ccgtcatcca 119460
caccttatcg tttgtgtgta ttgttgctat ggcgacacac ctgtgtggtg gttggtccag 119520
acgcgggcga cgcacacacc ctagcgtgcg ttacgtgtgc ctgccgcccg aacgcgggta 119580
gggtatgggg cggggatggg gagagcccac acgcggaaag caagaacaat aaaggcggcg 119640
ggatctagtt gatatgcgtc tctgggtgtt tttggggtgt ggtgggcgcg gggcggtcat 119700
tggacggggg tgcagttaaa tacatgcccg ggacccatga agcatgcgcg acttccgggc 119760
ctcggaaccc acccgaaacg gccaacggac gtctgagcca ggcctggcta tccggagaaa 119820
cagcacacga cttggcgttc tgtgtgtcgc gatgtctctg cgcgcagtct ggcatctggg 119880
gcttttggga agcctcgtgg gggctgttct tgccgccacc catctgggac ctgcggccaa 119940
cacaacggac cccttaacgc acgccccagt gtcccctcac cccagccccc tggggggctt 120000
tgccgtcccc ctcgtagtcg gtgggctgtg tgccgtagtc ctgggggcgg cgtgtctgct 120060
```

-continued

```
tgagctcctg cgtcgtacgt gccgcgggtg ggggcgttac catccctaca tggacccagt 120120
tgtcgtataa tttttcccc cccccccttc tccgcatggg tgatgtcggg tccaaactcc 120180
cgacaccacc agctggcatg gtataaatca ccggtgcgcc ccccaaacca tgtccggcag 120240
ggggatgggg ggcgaatgcg gagggcaccc aacaacaccg ggctaaccag gaaatccgtg 120300
gccccggccc ccaacaaaga tcgcggtagc ccggccgtgt gacattatcg tccataccga 120360
ccacaccgac gaatcccta aggggagg gccattttac gaggaggagg ggtataacaa 120420
agtctgtctt taaaaagcag gggttaggga gttgttcggt cataagcttc agtgcgaacg 120480
accaactacc ccgatcatca gttatcctta aggtctcttt tgtgtggtgc gttccggtat 120540
ggggggggct gccgccaggt tggggccgt gattttgttt gtcgtcatag tgggcctcca 120600
tggggtccgc ggcaaatatg ccttggcgga tgcctctctc aagatggccg accccaatcg 120660
ctttcgcggc aaagaccttc cggtcctgga ccagctgacc gaccctccgg gggtccggcg 120720
cgtgtaccac atccaggcgg gcctaccgga cccgttccag ccccccagcc tcccgatcac 120780
ggtttactac gccgtgttgg agcgcgcctg ccgcagcgtg ctcctaaacg caccgtcgga 120840 ggcccccag attgtccgcg gggcctccga agacgtccgg aaacaacccct acaacctgac 120900 catcgcttgg tttcggatgg gaggcaactg tgctatcccc atcacggtca tggagtacac 120960
cgaatgctcc tacaacaagt ctctgggggc ctgtcccatc cgaacgcagc cccgctggaa 121020
ctactatgac agcttcagcg ccgtcagcga ggataacctg gggttcctga tgcacgcccc 121080
cgcgtttgag accgccggca cgtacctgcg gctcgtgaag ataaacgact ggacggagat 121140
tacacagttt atcctggagc accgagccaa gggctcctgt aagtacgccc tcccgctgcg 121200 catcccccg tcagcctgcc tctccccca ggcctaccag caggggtga cggtggacag 121260 catcgggatg ctgcccgct tcatccccga gaaccagcgc accgtcgccg tatacagctt 121320
gaagatcgcc gggtggcacg ggcccaaggc cccatacacg agcaccctgc tgccccggga 121380
gctgtccgag accccaacg ccacgcagcc agaactcgcc ccggaagacc ccgaggattc 121440
ggccctcttg gaggacccg tggggacggt ggcgccgcaa atcccaccaa actggcacat 121500
cccgtcgatc caggacgccg cgacgcctta ccatcccccg gccacccga acaacatggg 121560 cctgatcgcc ggcgcggtgg gcggcagtct cctggcagcc ctggtcattt gcggaattgt 121620
gtactggatg caccgccgca ctcggaaagc cccaaagcgc atacgcctcc cccacatccg 121680
ggaagacgac cagccgtcct cgcaccagcc cttgtttac tagataccccc cccttaatgg 121740 gtgcggggg gtcaggtctg cggggttggg atgggacctt aactccatat aaagcgagtc 121800
tggaaggggg gaaaggcgga cagtcgataa gtcggtagcg ggggacgcgc acctgttccg 121860
cctgtcgcac ccacagcttt ttcgcgaacc gtcccgtttc gggatgccgt gccgccgtt 121920 gcagggcctg gtgctcgtgg gcctctgggt ctgtgccacc agcctggttg tccgtggccc 121980
cacggtcagt ctggtatcaa actcatttgt ggacgccggg gccttggggc ccgacggcgt 122040
agtggaggaa gacctgctta ttctcgggga gcttcgcttt gtgggggacc aggtccccca 122100
caccacctac tacgatgggg tcgtagagct gtggcactac cccatgggac acaaatgccc 122160
acgggtcgtg catgtcgtca cggtgaccgc gtgcccacgt cgccccgccg tggcatttgc 122220
cctgtgtcgc gcgaccgaca gcactcacag ccccgcatat cccaccctgg agctgaatct 122280
ggcccaacag ccgcttttgc gggtccggag ggcgacgcgt gactatgccg gggtgtacgt 122340
gttacgcgta tgggtcgggg acgcaccaaa cgccagcctg tttgtcctgg ggatggccat 122400
```

-continued

```
agccgccgaa ggtactctgg cgtacaacgg ctcggcccat ggctcctgcg acccgaaact 122460
gcttccgtct tcggccccgc gtctggcccc ggcgagcgta taccaacccg cccctaaccc 122520
ggcctccacc ccctcgacca ccacctccac cccctcgacc accatccccg ctccccaagc 122580
atcgaccaca cccttcccca cgggagaccc aaaaccccaa cctcacgggg tcaaccacga 122640
acccccatcg aatgccacgc gagcgacccg cgactcgcga tatgcgctaa cggtgaccca 122700
gataatccag atagccatcc ccgcgtccat tatagccctg gtgtttctgg ggagctgtat 122760
ttgctttata cacagatgtc aacgccgcta ccgacgctcc cgccgcccga tttacagccc 122820
ccagataccc acgggcatct catgcgcggt gaacgaagcg gccatggccc gcctcggagc 122880
cgagctcaaa tcgcatccga gcaccccccc caaatcccgg cgccggtcgt cacgcacgcc 122940
aatgccctcc ctgacggcca tcgccgaaga gtcggagccc gcgggggcgg ctgggcttcc 123000
gacgcccccc gtggacccca cgacatccac cccaacgcct cccctgttgg tataggtcca 123060
cggccactgg ccggggggcac cacataaccg accgcagtca ctgagttggg aataaaccgg 123120
tattatttac ctatatccgt gtatgtccat ttctttcttc cccccccccc ccggaaacca 123180
aagaaggaag caaagaatgg atgggaggag ttcaggaagc cggggagagg gcccgcggcg 123240
catttaaggc gttgttgtgt tgactttggc tcttctggcg ggttggtgcg gtgctgtttg 123300
ttgggctccc attttacccg aagatcggct gctatccccg ggacatggat cgcggggcgg 123360 tggtgggggtt tcttctcggt gtttgtgttg tatcgtgctt ggcgggaacg cccaaaacgt 123420
cctggagacg ggtgagtgtc ggcgaggacg tttcgttgct tccagctccg gggcctacgg 123480
ggcgcggccc gacccagaaa ctactatggg ccgtggaacc cctggatggg tgcggcccct 123540
tacacccgtc gtgggtctcg ctgatgcccc ccaagcaggt gcccgagacg gtcgtggatg 123600
cggcgtgcat gcgcgctccg gtcccgctgg cgatggcgta cgcccccccg gccccatctg 123660
cgaccggggg tctacgaacg gacttcgtgt ggcaggagcg cgcggccgtg gttaaccgga 123720
gtctggttat tcacggggtc cgagagacgg acagcggcct gtataccctg tccgtgggcg 123780
acataaagga cccggctcgc caagtggcct cggtggtcct ggtggtgcaa ccggccccag 123840
ttccgacccc accccccgacc ccagccgatt acgacgagga tgacaatgac gagggcgagg 123900
acgaaagtct cgccggcact cccgccagcg ggaccccccg gctcccgcct cccccccgccc 123960 ccccgaggtc ttggcccagc gcccccgaag tctcacatgt gcgtggggtg accgtgcgta 124020
tggagactcc ggaagctatc ctgttttccc ccggggagac gttcagcacg aacgtctcca 124080
tccatgccat cgcccacgac gaccagacct actccatgga cgtcgtctgg ttgaggttcg 124140
acgtgccgac ctcgtgtgcc gagatgcgaa tatacgaatc gtgtctgtat caccccgcagc 124200 tcccagaatg tctgtccccg gccgacgcgc cgtgcgccgc gagtacgtgg acgtctcgcc 124260
tggccgtccg cagctacgcg gggtgttcca gaacaaaccc cccaccgcgc tgttcggccg 124320
aggctcacat ggagccgtc ccggggctgg cgtggcaggc ggcctccgtc aatctggagt 124380
tccgggacgc gtccccacaa cactccggcc tgtatctgtg tgtggtgtac gtcaacgacc 124440
atattcacgc ctggggccac attaccatca gcaccgcggc gcagtaccgg aacgcggtgg 124500
tggaacagcc cctcccacag cgcggcgcgg atttggccga gcccacccac ccgcacgtcg 124560
gggcccctcc ccacgcgccc ccaacccacg gcgccctgcg gttaggggcg gtgatggggg 124620
ccgccctgct gctgtctgcg ctggggttgt cggtgtgggc gtgtatgacc tgttggcgca 124680
ggcgtgcctg gcgggcggtt aaaagcaggg cctcgggtaa ggggcccacg tacattcgcg 124740
tggccgacag cgagctgtac gcggactgga gctcggacag cgagggagaa cgcgaccagg 124800
```

```
tcccgtggct ggcccccccg gagagacccg actctccctc caccaatgga tccggctttg 124860
agatcttatc accaacggct ccgtctgtat acccccgtag cgacgggcat caatctcgcc 124920
gccagctcac aacctttgga tccggaaggc ccgatcgccg ttactcccag gcctccgatt 124980
cgtccgtctt ctggtaaggc gccccatccc gaggccccac gtcggtcgcc gaactgggcg 125040
accgccggcg aggtggacgt cggagacgag ctaatcgcga tttccgacga acgcggaccc 125100
ccccgacatg accgcccgcc cctcgccacg tcgaccgcgc cctcgccaca cccgcgaccc 125160
ccgggctaca cggccgttgt ctccccgatg gccctccagg ctgtcgacgc cccctccctg 125220
tttgtcgcct ggctggccgc tcggtggctc cggggggctt ccggcctggg ggccgtcctg 125280
tgtgggattg cgtggtatgt gacgtcaatt gcccgaggcg cacaaagggc cggtggtccg 125340
cctagccgca gcaaattaaa aatcgtgagt cacagcgacc gcaacttccc acccggagct 125400
ttcttccggc ctcgatgacg tcccggctct ccgatcccaa ctcctcagcg cgatccgaca 125460
tgtccgtgcc gctttatccc acggcctcgc cagtttcggt cgaagcctac tactcggaaa 125520
gcgaagacga ggcggccaac gacttcctcg tacgcatggg ccgccaacag tcggtattaa 125580
ggcgttgacg cagacgcacc cgctgcgtcg gcatggtgat cgcctgtctc ctcgtggccg 125640
ttctgtcggg cggatttggg gcgctcctga tgtggctgct ccgctaaaag accgcatcga 125700
cacgcgcgtc cttcttgtcg tctctcttcc cccccatcac cccgcaattt gcacccagcc 125760
tttaactaca ttaaattggg ttcgattggc aatgttgtct cccggttgat ttttgggtgg 125820
gtggggagtg ggtgggtggg gagtgggtgg gtggggagtg ggtgggtggg gagtgggtgg 125880
gtggggagtg ggtgggtggg gagtgggtgg gtggggagtg ggtgggtggg gagtgggtgg 125940
gtggggagtg ggtgggtggg gagtggcaag gaagaaacaa gcccgaccac cagacagaaa 126000
atgtaaccat acccaaaccg actctggggg ctgtttgtgg ggtcggaacc ataggatgaa 126060
caaaccaccc cgtacctccc gcacccaagg gtgcgggtgg ctcatcggca tctgtccggt 126120
atgggttgtt ccccacccac tcgcgttcgg acgtcttaga atcatggcgg ttttctatgc 126180
cgacatcggt tttctccccc gcaataagac acgatgcgat aaaatctgtt tgtaaaattt 126240
attaagggta caaattgccc tagcacaggg gtggggttag ggccgggtcc ccacacccaa 126300
acgcaccaaa cagatgcagg cagtgggtcg agtacagccc cgcgtacgaa cacgtcgatg 126360
cgtgtgtcag acagcaccag aaagcacagg ccatcaacag gtcgtgcatg tgtcggtggg 126420
tttggacgcg gggggccatg gtggtgataa agttaatggc cgccgtccgc cagggccaca 126480
ggggcgacgt ctcttggttg gcccggagcc actgggtgtg gaccagccgc gcgtggcggc 126540
ccaacatggc ccctgtagcc gggggcgggg gatcgcgcac gtttgcagcg cacatgcgag 126600
acacctcgac cacggttcga aagaaggccc ggtggtccgc gggcaacatc accaggtgcg 126660
caagcgcccg ggcgtccaga gggtagagcc ctgagtcatc cgaggttggc tcatcgcccg 126720
ggtcttgccg caagtgcgtg tgggttgggc ttccggtggg cgggacgcga accgcggtgt 126780
ggatcccgac gcgggcccga gcgtatgctc catcttgtgg ggagaagggg tctgggctcg 126840
ccaggggggc atacttgccc gggctataca gacccgcgag ccgtacgtgg ttcgcggggg 126900
gtgcgtgggg tccggggctc cctgggagac cggggttgtc gtggatccct ggggtcacgc 126960
ggtaccctgg ggtctctggg agctcgcggt actctgggtt ccctaggttc tcggggtggt 127020
cgcggaaccc ggggctcccg gggaacacgg ggtgtcctgg ggattgttgg cggtcggacg 127080
gcttcagatg gcttcgagat cgtagtgtcc gcaccgactc gtagtagacc cgaatctcca 127140
```

```
cattgccccg ccgcttgatc attatcaccc cgttgcgggg gtccggagat catgcgcggg 127200
tgtcctcgag gtgcgtgaac acctctgggg tgcatgccgg cggacggcac gccttttaag 127260
taaacatctg ggtcgcccgg cccaactggg gccgggggtt gggtctggct catctcgaga 127320
gacacggggg ggaaccaccc tccgcccaga gactcgggtg atggtcgtac ccgggactca 127380
acgggttacc ggattacggg gactgtcggt cacggtcccg ccggttcttc gatgtgccac 127440
acccaaggat gcgttggggg cgatttcggg cagcagcccg ggagagcgca gcaggggacg 127500
ctccgggtcg tgcacggcgg ttctggccgc ctcccggtcc tcacgccccc ttttattgat 127560
ctcatcgcgt acgtcggcgt acgtcctggg cccaacccgc atgttgtcca ggaaggtgtc 127620
cgccatttcc agggcccacg acatgctttt cccccgacg agcaggaagc ggtccacgca 127680
acggtcgccg ccggtcgcct cgacgagggc gttcctcctg cgggaaggca cgaacgcggg 127740
tgagccccct cctccgcccc cgcgtccccc ctcctccgcc cccgcgtccc ccctcctccg 127800
cccccgcgtc cccctcctc cgcccccgcg tcccccctcc tccgccccg cgtcccccct 127860 cctctgccca cccaaggtgc ttacccgtgc aaaaaaggcg gaccggtggg tttctgtcgt 127920
cggaggcccc cggggtgcgt ccctgtgtt tcgtgggtgg ggtgggcggg tctttcccc 127980 ccgcgtccgc gtgtccccttt ccgatgcgat cccgatcccg agccggggcg tcgcgatgcc 128040
gacgccgtcc gctccgacgg ccctctgcga ctcccgctcc cggtccgcgt gctccgcagc 128100
cgctcccgtc gttcgtggct ggcgccgtct gcgggcgtcg gtcgcgccgg gccttttatgt 128160 gcgccggaga gacccgcccc ccgccgcccg ggtccgcccc cggggccggc gcggagtcgg 128220
gcacggcgcc agtgctcgca cttcgcccta ataatatata tatattggga cgaagtgcga 128280
acgcttcgcg ttctcacttc ttttacccgg cggccccgcc cccttggggc ggtcccgccc 128340
gccggccaat gggggggcgg caaggcgggc ggcccaaggg ccgcccgccg tcccgttggt 128400
cccggcgtcc ggcgggcggg accgggggcc cggggacggc caacgggcgc gcggggctcg 128460
tatctcatta ccgccgaacc gggaagtcgg ggcccgggcc ccgcccctg cccgttcctc 128520 gttagcatgc ggaacggaag cggaaaccgc cggatcgggc ggtaatgaga tgccatgcgg 128580
ggcggggcgc ggacccaccc gccctcgcgc cccgtccatg gcagatggcg cggatgggcg 128640
gggccggggg ttcgaccaac gggccgcggc cacgggcccc cggcgtgccg gcgtcggggc 128700
ggggtcgtgc ataatggaat tccgttcggg gtgggcccgc cgggggcgg ggggccggcg 128760 gcctccgctg ctcctccttc ccgccggccc ctgggactat atgagcccga ggacgccccg 128820
atcgtccaca cggagcgcgg ctgccgacac ggatccacga cccgacgcgg gaccgccaga 128880
gacagaccgt cagacgctcg ccgcgccggg acgccgatac gcggacgaag cgcgggaggg 128940
ggatcggccg tccctgtcct ttttccccac ccaagcatcg accggtccgc gctagttccg 129000
cgtcgacggc gggggtcgtc ggggtccgtg ggtctcgccc cctcccccca tcgagagtcc 129060
gtaggtgacc taccgtgcta cgtccgccgt cgcagccgta tccccggagg atcgccccgc 129120
atcggcgatg gcgtcggaga acaagcagcg ccccggctcc ccgggcccca ccgacgggcc 129180
gccgcccacc ccgagcccag accgcgacga gcggggggcc ctcgggtggg gcgcggagac 129240
ggaggagggc ggggacgacc ccgaccacga ccccgaccac ccccacgacc tcgacgacgc 129300
ccggcgggac gggagggccc ccgcggcggg caccgacgcc ggcgaggacg ccggggacgc 129360
cgtctcgtcg cgacagctgg ctctgctggc ctccatggta gaggaggccg tccggacgat 129420
cccgacgccc gaccccgcgg cctcgccgcc ccggacccc gcctttctag ccgacgacga 129480 tgacgggggac gagtacgacg acgcagccga cgccgccggc gaccgggccc cggccgcggg 129540
```

-continued

```
ccgcgaacgg gaggccccgc tacgcggcgc gtatccggac cccacggacc gcctgtcgcc 129600
gcgcccgccg gcccagccgc cgcggagacg tcgtcacggc cggcggcggc catcggcgtc 129660
atcgacctcg tcggactccg ggtcctcgtc ctcgtcgtcc gcatcctctt cgtcctcgtc 129720
gtccgacgag gacgaggacg acgacggcaa cgacgcggcc gaccacgcac gcgaggcgcg 129780
ggccgtcggg cggggtccgt cgagcgcggc gccggaagcc cccgggcgga cgccgccccc 129840
gcccgggcca cccccctct ccgaggccgc gcccaagccc cgggcggcgg cgaggacccc 129900
cgcggcctcc gcgggccgca tcgagcgccg ccgggcccgc gcggcggtgg ccggccgcga 129960
cgccacgggc cgcttcacgg ccgggcagcc ccggcgggtc gagctggacg ccgacgcggc 130020
ctccggcgcc ttctacgcgc gctatcgcga cgggtacgtc agcggggagc cgtggcccgg 130080
cgccgggccc ccgcccccgg ggcgggtgct gtacggcggc ctgggcgaca gccgcccggg 130140
cctctggggg gcgcccgagg cggaggaggc gcgacgccgg ttcgaggcct cgggcgcccc 130200
ggcggccgtg tgggcgcccg agctgggcga cgccgcgcag cagtacgccc tgatcacgcg 130260
gctgctgtac accccggacg cggaggccat ggggtggctc cagaacccgc gcgtggtccc 130320
cggggacgtg gcgctggacc aggcctgctt ccggatctcg ggcgccgcgc gcaacagcag 130380
ctccttcatc accggcagcg tggcgcgggc cgtgcccac ctgggctacg ccatggcggc 130440
cggccgcttc ggctggggcc tggcgcacg ggcggccgcc gtggccatga ccgccgata 130500 cgaccgcgcg cagaagggct tcctgctgac cagcctgcgc cgcgcctacg cgcccctgtt 130560
ggcgcgcgag aacgcggcgc tgacgggggc gcgcgggagc cccggcgccg gcgcagatga 130620 cgaggggtc gccgccgtcg ccgccgccgc accgggcgag cgcgcggtgc ccgccgggta 130680
cggcgccgcg gggatcctcg ccgccctggg gcggctgtcc gccgcgcccg cctcccccgt 130740 gggggcgac gaccccgacg ccgcccgcca cgccgacgcc gacgccgggc gccgcgccca 130800
ggccggccgc gtggccgtcg agtgcctggc cgcctgccgc gggatcctgg aggcgctggc 130860
cgagggcttc gacggcgacc tggcggccgt cccggggctg gccggggccc ggcccgccag 130920 cccccgcgg ccggagggac ccgcgggccc cgcttccccg ccgccgccgc acgccgacgc 130980
gccccgcctg cgcgcgtggc tgcgcgagct gcggttcgtg cgcgacgcgc tggtgctcat 131040
gcgcctgcgc ggggacctgc gcgtggccgg cggcagcgag gccgccgtgg ccgccgtgcg 131100
cgccgtgagc ctggtcgccg gggccctggg ccccgcgctg ccgcgggacc cgcgcctgcc 131160
gagctccgcg ccgccgccg ccgcggacct gctgtttgag aaccagagcc tccgcccct 131220 gctggcggcg gcggccagcg caccggacg cgccgacgcg ctggcggccg ccgccgcctc 131280
cgccgcgccg cgggaggggc gcaagcgcaa gagtcccggc ccggcccggc cgcccggagg 131340
cggcggcccg cgacccccga agacgaagaa gagcggcgcg gacgccccg gctcggacgc 131400 ccgcgccccc ctccccgcgc ccccctccac gccccggggg cccgagccca cccccgccca 131460
gcccgcggcg gcccggggcg ccgcggcgca ggccgcccg cgcccgtgg cgctgtcgcg 131520 ccggcccgcc gagggccccg accccctggg cggctggcgg cggcagcccc gggggcccag 131580
ccacacggcg gcgcccgcgg ccgccgccct ggaggcctac tgctccccgc gcgccgtggc 131640
cgagctcacg gaccacccgc tgttccccgt ccctggcga ccggccctca tgtttgaccc 131700
gcgggccctg gctcgatcg ccgcgcggtg cgccgggccc gccccgccg cccaggccgc 131760 gtgcggcggc gacgacgacg agaaccccca ccccacgggg ccgccgggg gccgcctctt 131820 tggcccctg cgcgcctcgg gcccgctgcg ccgcatggcg gcctggatgc gccagatccc 131880
```

```
cgaccccgag gacgtgcgcg tggtggtgct gtactcgccg ctgccgggcg aggacctggc   131940
cggcggcggg gcctcggggg ggccgccgga gtggtccgcc gagcgcggcg ggctgtcctg   132000
cctgctggcg gccctggcca accggctgtg cgggccggac acggccgcct gggcgggcaa   132060
ctggaccggc gcccccgacg tgtcggcgct gggcgcgcag ggcgtgctgc tgctgtccac   132120
gcgggacctg gccttcgccg gggccgtgga gtttctgggg ctgctcgcca gcgccggcga   132180
ccggcggctc atcgtggtca acaccgtgcg cgcctgcgac tggcccgccg acgggccggc   132240
ggtgtcgcgg cagcacgcct acctggcgtg cgacctgctg cccgccgtgc agtgcgccgt   132300
gcgctggccg gcggcgcggg acctgcgccg cacggtgctg gcctcgggcc gcgtgttcgg   132360
cccgggggtc ttcgcgcgcg tggaggccgc gcacgcgcgc ctgtaccccg acgcgccgcc   132420
gctgcgcctg tgccgcggcg gcaacgtgcg ctaccgcgtg cgcacgcgct tcggcccgga   132480
cacgccggtg cccatgtccc cgcgcgagta ccgccgggcc gtgctgccgg cgctggacgg   132540
ccgggcggcg gcctcgggga ccaccgacgc catggcgccc ggcgcgccgg acttctgcga   132600
ggaggaggcc cactcgcacc gcgcctgcgc gcgctggggc ctgggcgcgc cgctgcggcc   132660
cgtgtacgtg gcgctggggc gcgaggcggt gcgcgccggc ccggcccggt ggcgcgggcc   132720 gcggaggggac ttttgcgccc gcgccctgct ggagcccgac gacgacgccc ccccgctggt   132780
gctgcgcggc gacgacgacg acggcccggg ggccctgccg ccggcgccgc ccgggattcg   132840
ctgggcctcg gccacgggcc gcagcggcac cgtgctggcg gcggcggggg ccgtggaggt   132900 gctggggggcg gaggcgggct tggccacgcc cccgcgacgg gacgttgtgg actgggaagg   132960
cgcctgggac gaagacgacg gcggcgcgtt cgaggggggac ggggtgctgt aacgggccgg   133020
gacggggcgg ggcgcttgtg aaacccgaag acgcaataaa cggcaacgac ctgattaagt   133080
tttgcagtag cgttgtttat tcgaggggcg ggaggggggcg aggggcggga ggggggcgagg   133140 ggcgggaggg ggcgagggggc gggagggggc gaggggcggg aggggggcgag gggcgggagg   133200 gggcgagggg cgggaggggg cgaggggcgg gaggggggcga ggggcgggag ggggcgaggg   133260
gcgggagggg gcgaggggcg ggaggggggcg aggggcggga ggggggcgagg ggcgggaggg   133320 ggcgaggggc gggaggggggc gaggggcggg aggggggcgag gggcgggagg gggcgagggg   133380
cgggaggggg cgaggggcgg gaggggggcga ggggcgggag ggggcgaggg gcggtggtgg   133440
tgcgcgggcg cccccggagg gtttggatct ctgacctgag attggcggca ctgaggtaga   133500
gatgcccgaa cccccccgag ggagcgcggg acgcggctgg ggagggctgg ggctggggag   133560
ggctggggcc ggggagggct ggggccgggg agggctgggg ccggggaggg ctggggccgg   133620
ggagggctgg ggccggggag ggctggggct ggggagggct ggggctgggg aggggcggtg   133680
gtgtgtagca ggagcggtgt gttgcgccgg ggtacgtctg gaggagcggg aggtgcgcgg   133740
tgacgtgtgg atgaggaaca ggagttgttg cgcggtgagt tgtcgctgtg agttgtgttg   133800
ttgggcaggt gtggtggatg acgtgacgtg tgacgtgcgg attgcgccgt gctttgttgg   133860
tgttgtttta cctgtggcag cccgggcccc ccgcgggcgc gcgcgcgcgc aaaaaaggcg   133920
ggcggcggtc cggcggcgt gcgcgcgcgc ggcgggcgtg gggggcgggg ccgcgggagc   133980 ggggggaggag cggggggagga gcggggggag gagcggggggg aggagcgggg ggaggagcgg   134040
ggggaggagc ggggggagga gcggggggag gagcggggggg aggagcgggg ggaggagcgg   134100
ggggaggagc ggggggagga gcggggggag gagcgggggg aggagcgggg ggaggagcgg   134160
ggggaggagc ggggggagga gcggggggag gagcggcaga ccccggaaac gggcccccccc   134220 caaaacacac ccccccgggggg tcgcgcgcgg cccttttaaag gcgggcggcg g           134271
```

```
<210> SEQ ID NO 5
<211> LENGTH: 74
<212> TYPE: DNA
<213> ORGANISM: Artificial Sequence
<220> FEATURE:
<223> OTHER INFORMATION: UL56-rpsL-neo primer

<400> SEQUENCE: 5
acaggaatac cagaataatg accaccacaa tcgcgaccac cccaaataca ggcctggtga      60
tgatggcggg atcg                                                       74

<210> SEQ ID NO 6
<211> LENGTH: 74
<212> TYPE: DNA
<213> ORGANISM: Artificial Sequence
<220> FEATURE:
<223> OTHER INFORMATION: UsIR-rpsL-neo primer

<400> SEQUENCE: 6
cccgaggacg ccccgatcgt ccacacggag cgcggctgcc gacacggatc tcagaagaac      60
tcgtcaagaa ggcg                                                       74

<210> SEQ ID NO 7
<211> LENGTH: 42
<212> TYPE: DNA
<213> ORGANISM: Artificial Sequence
<220> FEATURE:
<223> OTHER INFORMATION: UL55 S primer

<400> SEQUENCE: 7
acgcgtcgac taaaaacaaa acatttcaaa caaatcgccc ca                        42

<210> SEQ ID NO 8
<211> LENGTH: 74
<212> TYPE: DNA
<213> ORGANISM: Artificial Sequence
<220> FEATURE:
<223> OTHER INFORMATION: UsIR-rpsL neo AS primer

<400> SEQUENCE: 8
cccgaggacg ccccgatcgt ccacacggag cgcggctgcc gacacggatc tcagaagaac      60
tcgtcaagaa ggcg                                                       74

<210> SEQ ID NO 9
<211> LENGTH: 28
<212> TYPE: DNA
<213> ORGANISM: Artificial Sequence
<220> FEATURE:
<223> OTHER INFORMATION: rpsL neo S primer

<400> SEQUENCE: 9
cggcatcgcc ctaaaattcg gcgtcctc                                        28

<210> SEQ ID NO 10
<211> LENGTH: 28
<212> TYPE: DNA
<213> ORGANISM: Artificial Sequence
<220> FEATURE:
<223> OTHER INFORMATION: rpsL neo AS primer

<400> SEQUENCE: 10
aagaaccggg cgcccctgcg ctgacagc                                        28
```

-continued

<210> SEQ ID NO 11
<211> LENGTH: 32
<212> TYPE: DNA
<213> ORGANISM: Artificial Sequence
<220> FEATURE:
<223> OTHER INFORMATION: gC S primer

<400> SEQUENCE: 11
cagatccgat gccggtttcg gaattccacc cg                              32

<210> SEQ ID NO 12
<211> LENGTH: 31
<212> TYPE: DNA
<213> ORGANISM: Artificial Sequence
<220> FEATURE:
<223> OTHER INFORMATION: gC AS primer

<400> SEQUENCE: 12
cgggttaaac acctggcggt cgtcctcgaa c                               31

<210> SEQ ID NO 13
<211> LENGTH: 74
<212> TYPE: DNA
<213> ORGANISM: Artificial Sequence
<220> FEATURE:
<223> OTHER INFORMATION: ICP6 R-rpsL-neo S primer

<400> SEQUENCE: 13
gttcctgtcg cgacacacgg cgccgctctg cggtattcgg gggggagggg ggcctggtga    60
tgatggcggg atcg                                                 74

<210> SEQ ID NO 14
<211> LENGTH: 74
<212> TYPE: DNA
<213> ORGANISM: Artificial Sequence
<220> FEATURE:
<223> OTHER INFORMATION: ICP6 R-rpsL-neo AS primer

<400> SEQUENCE: 14
agggtcccgt ccgccttctc cgtgacatac agggtcatgg attggctatg tcagaagaac    60
tcgtcaagaa ggcg                                                 74

<210> SEQ ID NO 15
<211> LENGTH: 98
<212> TYPE: DNA
<213> ORGANISM: Artificial Sequence
<220> FEATURE:
<223> OTHER INFORMATION: dIR S primer

<400> SEQUENCE: 15
acaggaatac cagaataatg accaccacaa tcgcgaccac cccaaataca gatccgtgtc    60
ggcagccgcg ctccgtgtgg acgatcgggg cgtcctcg                       98

<210> SEQ ID NO 16
<211> LENGTH: 98
<212> TYPE: DNA
<213> ORGANISM: Artificial Sequence
<220> FEATURE:
<223> OTHER INFORMATION: dIR AS primer -continued

```
<400> SEQUENCE: 16
cgaggacgcc ccgatcgtcc acacggagcg cggctgccga cacggatctg tatttggggt        60
ggtcgcgatt gtggtggtca ttattctggt attcctgt                                98
```